(12) United States Patent
Kameyama et al.

(10) Patent No.: US 10,100,120 B2
(45) Date of Patent: Oct. 16, 2018

(54) ANTIBODY WHICH SPECIFICALLY BINDS TO HUMAN CRTH2

(71) Applicant: KYOWA HAKKO KIRIN CO., LTD, Tokyo (JP)

(72) Inventors: Naoya Kameyama, Tokyo (JP); Munetoshi Ando, Tokyo (JP); Shinya Ogawa, Tokyo (JP); Kazuki Okada, Tokyo (JP)

(73) Assignee: KYOWA HAKKO KIRIN CO., LTD, Tokyo (JP)

( * ) Notice: Subject to any disclaimer, the term of this patent is extended or adjusted under 35 U.S.C. 154(b) by 0 days.

(21) Appl. No.: 15/932,185

(22) Filed: Feb. 16, 2018

(65) Prior Publication Data
US 2018/0222994 A1 Aug. 9, 2018

Related U.S. Application Data

(60) Division of application No. 15/342,534, filed on Nov. 3, 2016, now Pat. No. 9,938,349, which is a continuation of application No. PCT/JP2016/071027, filed on Jul. 15, 2016.

(30) Foreign Application Priority Data

Jul. 15, 2015 (JP) ................................. 2015-141633

(51) Int. Cl.
*C07K 16/28* (2006.01)
*G01N 33/92* (2006.01)

(52) U.S. Cl.
CPC ......... *C07K 16/2896* (2013.01); *G01N 33/92* (2013.01); *C07K 2317/24* (2013.01); *C07K 2317/34* (2013.01); *C07K 2317/565* (2013.01); *C07K 2317/732* (2013.01); *C07K 2317/76* (2013.01)

(58) Field of Classification Search
CPC ............ C07K 16/2896; C07K 2317/76; C07K 2317/565; C07K 2317/34; C07K 2317/24
See application file for complete search history.

(56) References Cited

U.S. PATENT DOCUMENTS 6,040,426 A 3/2000 Ogawa et al.

FOREIGN PATENT DOCUMENTS

| WO | 97/46677 A1 | 12/1997 |
| WO | 2014/144865 A2 | 9/2014 |

OTHER PUBLICATIONS

Hiroyuki Hirai, et al., "Prostaglandin D2 Selectively Induces Chemotaxis in T Helper Type 2 Cells, Eosinophils, and Basophils via Seven-Transmembrane Receptor CRTH2", The Journal of Experimental Medicine, vol. 193, No. 2, Jan. 15, 2001, pp. 255-261.
Jenny M Mjösberg, et al., "Human IL-25- and IL-33-responsive type 2 innate lymphoid cells are defined by expression of CRTH2 and CD161", Nature Immunology, vol. 12, No. 11, Nov. 2011, pp. 1055-2104.
Lorenzo Cosmi, et al., "CRTH2 is the most reliable marker for the detection of circulating human type 2 Th and type 2 T cytotoxic cells in health and disease", European Journal of Immunology, 2000, 30(10), pp. 2972-2979.
Kok Loon Wong, et al., "Gene expression profiling reveals the defining features of the classical, intermediate, and nonclassical human monocyte subsets", Blood, Aug. 4, 2011, vol. 118, No. 5, pp. e16-e31.
Chaoyu Irvin, et al., "Increased frequency of dual-positive TH2/TH17 cells in bronchoalveolar lavage fluid characterizes a population of patients with severe asthma", Journal of Allergy and Clinical Immunology, vol. 134, No. 5, 2014, pp. 1175-1186.
K. Mutalithas, et al, "CRTH2 expression on T cells in asthma", Clinical and Experimental Immunology, 2010, 161(1), pp. 34-40.
Masahiro Iwasaki, et al., "Association of a New-Type Prostaglandin D2 Receptor CRTH2 with Circulating T Helper 2 Cells in Patients with Atopic Dermatitis", The Journal of Investigative Dermatology, 2002, 119(3), pp. 609-616.
Gerald J. Gleich, et al., "The Eosinophilic Leukocyte: Structure and Function", Advances in Immunology, vol. 39, 1986, pp. 177-253.
C. J. Corrigan, et al., "T cells and eosinophils in the pathogenesis of asthma", Immunology Today, vol. 13, No. 12, 1992, pp. 501-506.
Mark C. Siracusa, et al., "Basophils and allergic inflammation", Journal of Allergy and Clinical Immunology, Oct. 2013, vol. 132, No. 4, pp. 789-801.
Kathleen R. Bartemes, et al., "Enhanced innate type 2 immune response in peripheral blood from patients with asthma", Journal of Allergy and Clinical Immunology, Sep. 2014, vol. 134, No. 3, pp. 671-678.
Kinya Nagata, et al., "Selective Expression of a Novel Surface Molecule by Human Th2 Cells In Vivo", Journal of Immunology, 1999, vol. 162, No. 3, total 10 pages.
"CRTH-2/GPR44 Antibody FAB33381N", Novus Biologicals [online], Jun. 26, 2015 Updated, [retrieved on Oct. 4, 2016], Retrieved from the Internet: <URL:http://www.funakoshi.co.jp/data/datasheet/NOV/FAB33381N.pdf>, full text, total 3 pages.

(Continued)

*Primary Examiner* — Ruixiang Li
(74) *Attorney, Agent, or Firm* — Sughrue Mion, PLLC

(57) ABSTRACT

There is provided an anti-human CRTH2 antibody which has desired activity by recognizing and binding to a specific human CRTH2; the antibody fragment; DNA which encodes the amino acid sequence of the antibody; a vector which comprises the DNA; hybridomas and antibody producing cells which produce the antibody; a method of producing the antibody; a composition which comprises the antibody or the antibody fragment; a treatment method and a diagnostic method of an allergic disease, an autoimmune disease, a disease accompanied by at least one of increase and hyperergasia of eosinophils; a disease accompanied by at least one of increase and hyperergasia of Th2 cells using the antibody or the antibody fragment; and a medicine and a diagnostic agent which comprise the antibody or the antibody fragment.

21 Claims, 17 Drawing Sheets

Specification includes a Sequence Listing.

(56) References Cited

OTHER PUBLICATIONS

"Human CRTH-2 Antibody", R&D Systems, Inc. [online], Mar. 13, 2015, [retrieved on Oct. 4, 2016], Retrieved from the Internet: <URL:http://www.funakoshi.co.jp/data/datasheet/RSD/MAB3338.pdf>, full text, total 1 page.
International Searching Authority, International Search Report for PCT/JP2016/071027 dated Oct. 11, 2106 [PCT/ISA/210].
International Searching Authority, Written Opinion for PCT/JP2016/071027 dated Oct. 11, 2106 [PCT/ISA/237].

[Fig. 1]

```
              1234567890123456789 0123   4567890123456789  012345678901234  5678901
Lym2 VL   DVVLTQTPVSLSVTLGDQASISC   RSSQSLEYSDGYTYLE   WYLQKPGQSPQVLIY   GVSNRFS
LV0       DIVMTQTPLSLPVTPGESASISC                      WYLQKPGQSPQVLIY
LV1       DIVMTQTPLSLPVTLGESASISC                      WYLQKPGQSPQVLIY
LV2a      DIVLTQTPLSLPVTLGESASISC                      WYLQKPGQSPQVLIY
LV2b      DIVMTQTPLSLPVTLGESASISC         CDR L1       WYLQKPGQSPQVLIY   CDR L2
LV2c      DVVLTQTPLSLPVTPGESASISC                      WYLQKPGQSPQVLIY
LV3a      DVVLTQTPLSLPVTPGESASISC                      WYLQKPGQSPQVLIY
LV3b      DVVLTQTPLSLPVTLGESASISC                      WYLQKPGQSPQVLIY
LV4       DVVLTQTPLSLPVTLGESASISC                      WYLQKPGQSPQVLIY 2345678901234567890123456789 0123   456789012   3456789012
Lym2 VL   GVPDRFIGSGSGTDFTLKISRVEPEDLGVYYC   FQATHDPLT   FGSGTKLEIK
LV0       GVPDRFSGSGSGTDFTLKISRVEAEDVGVYYC                FGQGTKLEIK
LV1       GVPDRFSGSGSGTDFTLKISRVEAEDVGVYYC                FGQGTKLEIK
LV2a      GVPDRFSGSGSGTDFTLKISRVEAEDVGVYYC                FGQGTKLEIK
LV2b      GVPDRFSGSGSGTDFTLKISRVEPEDVGVYYC    CDR L3     FGQGTKLEIK
LV2c      GVPDRFSGSGSGTDFTLKISRVEAEDVGVYYC                FGQGTKLEIK
LV3a      GVPDRFSGSGSGTDFTLKISRVEPEDVGVYYC                FGQGTKLEIK
LV3b      GVPDRFSGSGSGTDFTLKISRVEAEDVGVYYC                FGQGTKLEIK
LV4       GVPDRFSGSGSGTDFTLKISRVEPEDVGVYYC                FGQGTKLEIK
```

[Fig.2]

```
              123456789012345678901234567890  12345   67890123456789   0123456789012345 6
Lym2 VH   EVQLVESGGGLVQPGRSMKLSCAASGFTFS    NYYMA   WVRQAPKKGLEWVA   TISYDGSSTYYRDSVKG
HV0       EVQLVESGGGVVQPGRSLRLSCAASGFTFS            WVRQAPGKGLEWVA
HV1       EVQLVESGGGVVQPGRSLRLSCAASGFTFS            WVRQAPGKGLEWVA
HV2a      EVQLVESGGGVVQPGRSLRLSCAASGFTFS    CDR     WVRQAPGKGLEWVA        CDR H2
HV2b      EVQLVESGGGVVQPGRSMRLSCAASGFTFS    H1      WVRQAPGKGLEWVA
HV3       EVQLVESGGGVVQPGRSMRLSCAASGFTFS            WVRQAPGKGLEWVA
HV4       EVQLVESGGGVVQPGRSMRLSCAASGFTFS            WVRQAPGKGLEWVA 7890123456789012345678901234567 8   901234567890 12   34567890123
Lym2 VH   RFTISRDNAKSTLYLQMDSLRSEDTATYYCAR       HHGYYYSGAGYFDY   WGQGVMVTVSS
HV0       RFTISRDNAKNSLYLQMNSLRAEDTAVYYCAR                        WGQGTMVTVSS
HV1       RFTISRDNAKNSLYLQMNSLRAEDTATYYCAR                        WGQGTMVTVSS
HV2a      RFTISRDNAKNSLYLQMNSLRAEDTATYYCAR         CDR H3         WGQGVMVTVSS
HV2b      RFTISRDNAKNSLYLQMNSLRAEDTAVYYCAR                        WGQGVMVTVSS
HV3       RFTISRDNAKNSLYLQMNSLRAEDTATYYCAR                        WGQGVMVTVSS
HV4       RFTISRDNAKSSLYLQMNSLRAEDTATYYCAR                        WGQGVMVTVSS
```

[FIG. 3(A)]
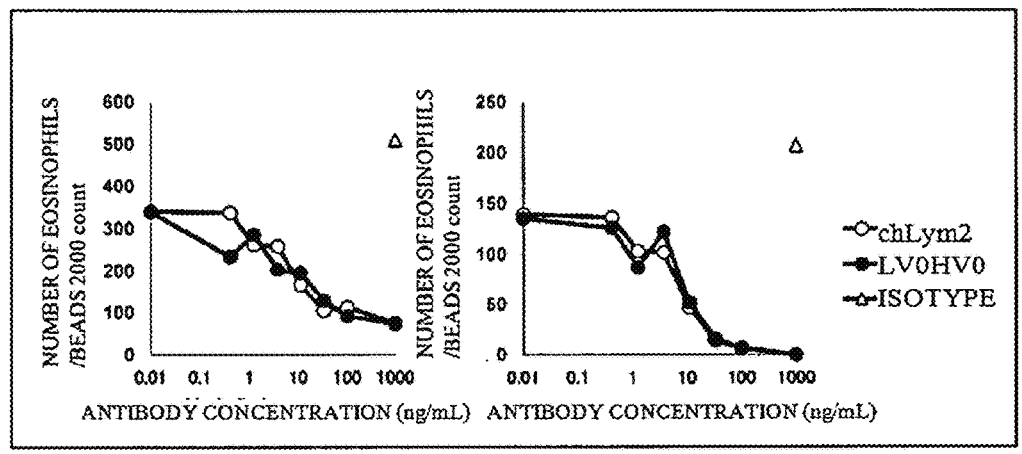
[FIG. 3(B)]
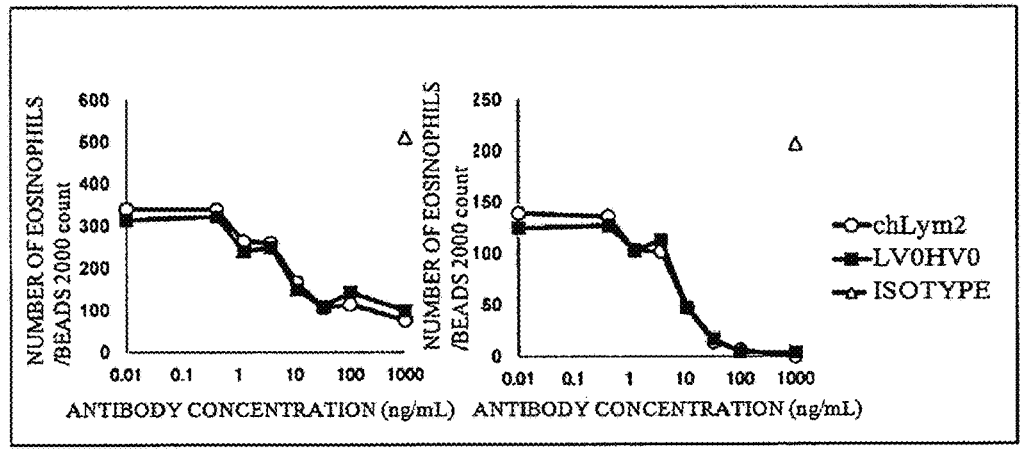
[FIG. 3(C)]
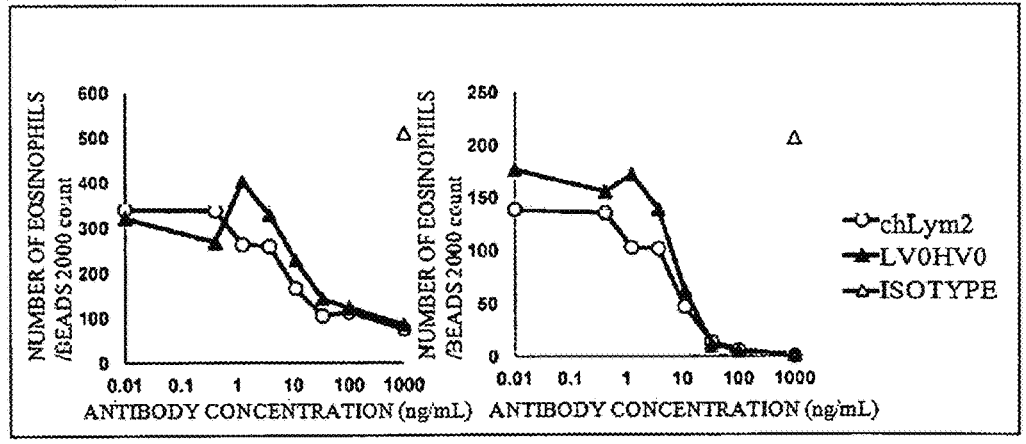

[FIG. 4(A)]
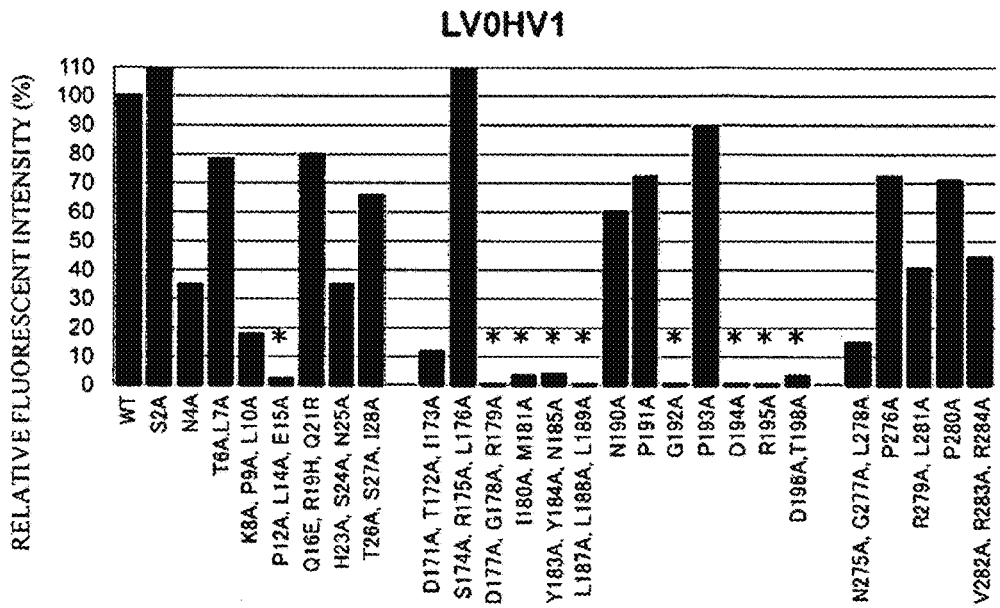
[FIG. 4(B)]
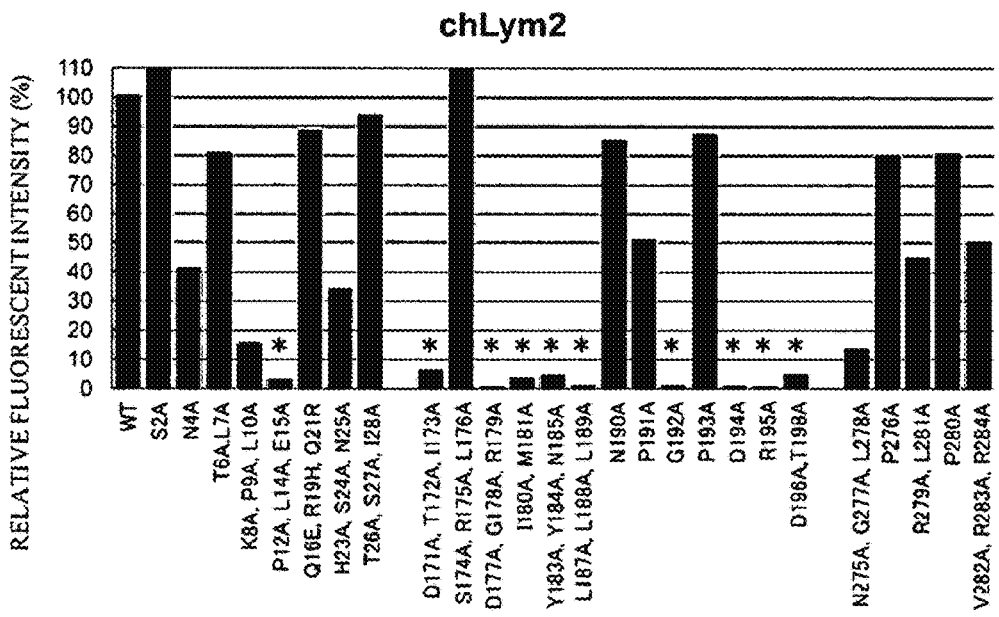

[FIG. 5(A)]
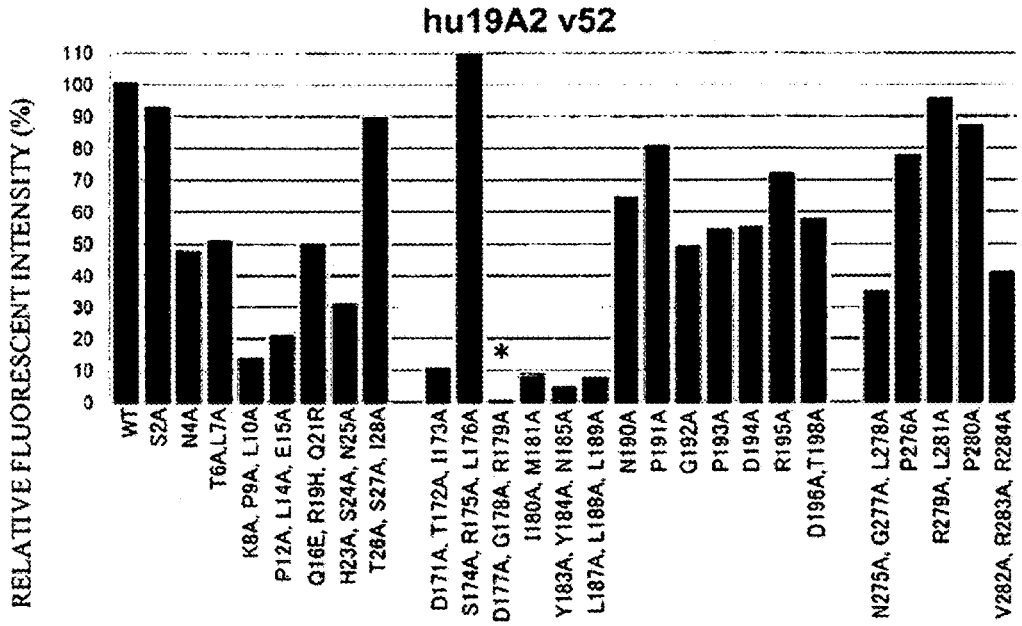
[FIG. 5(B)]
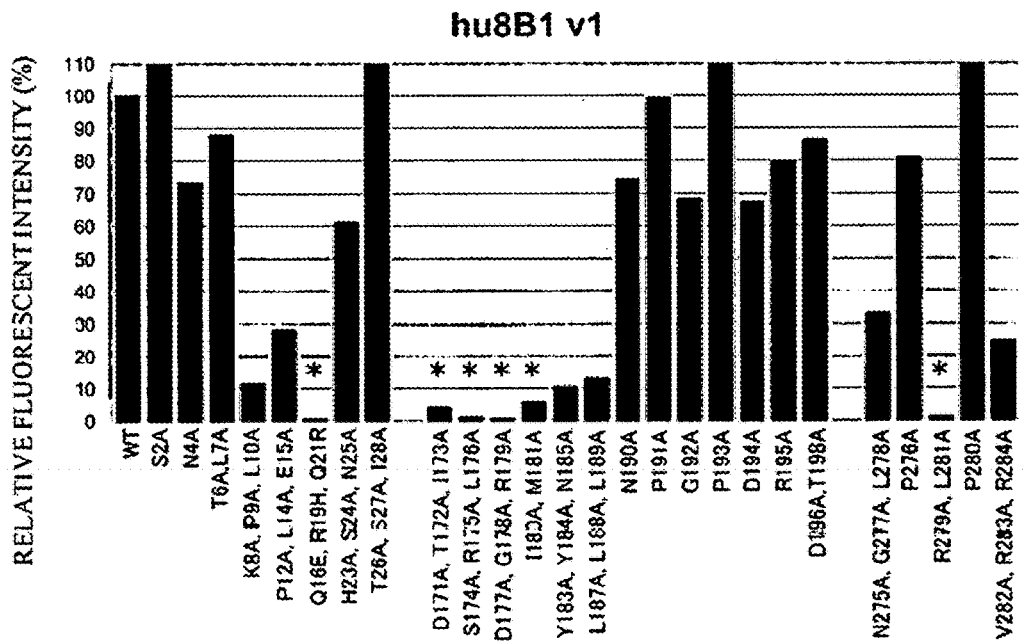

[FIG. 6(A)]
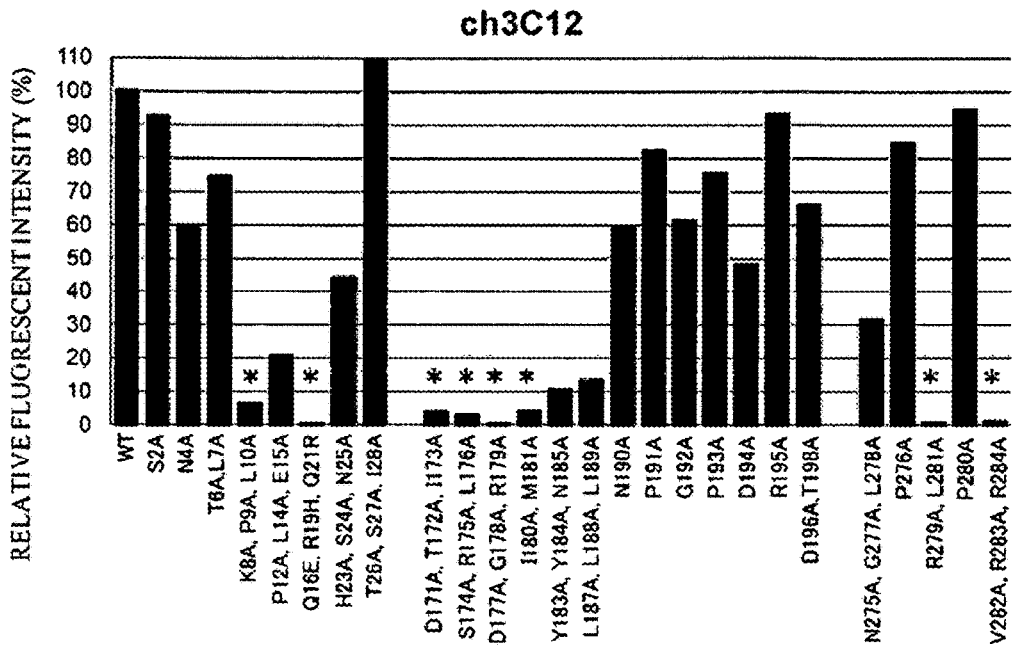
[FIG. 6(B)]
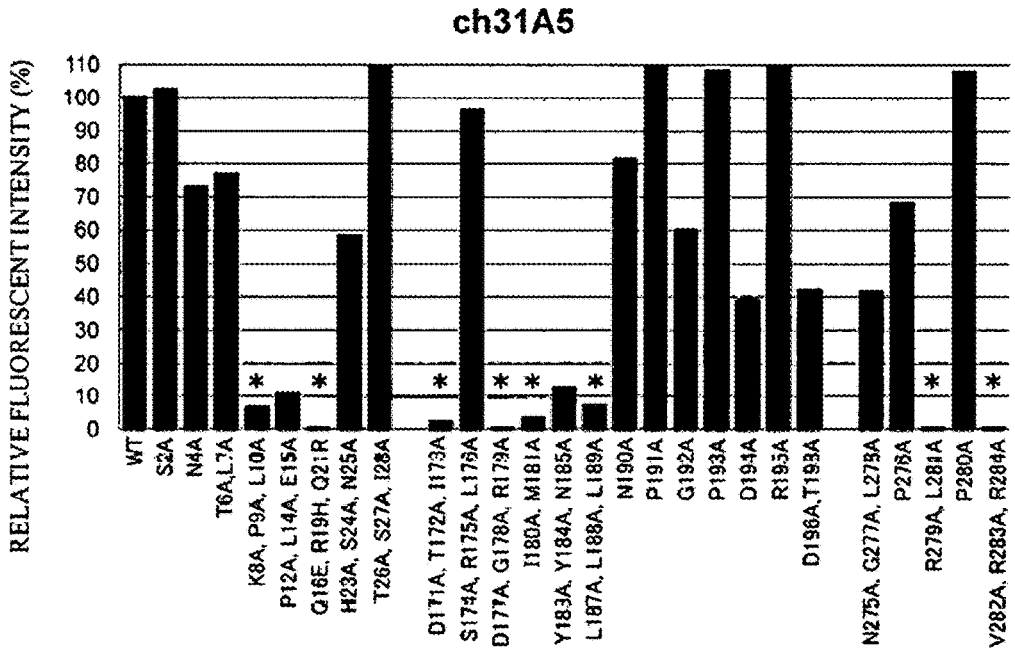

[FIG. 7]
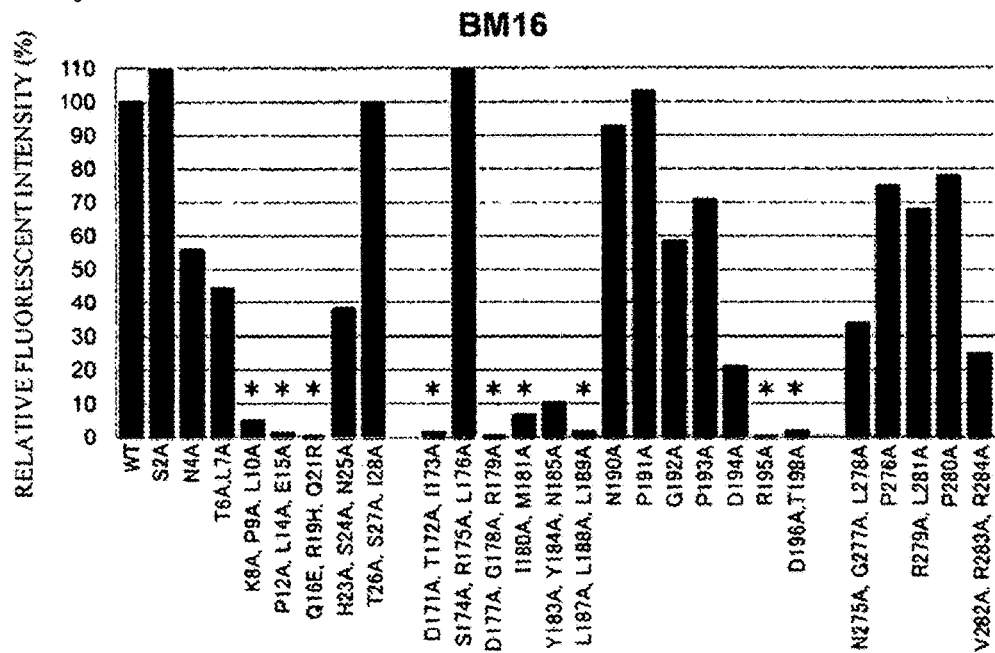
[FIG. 8]
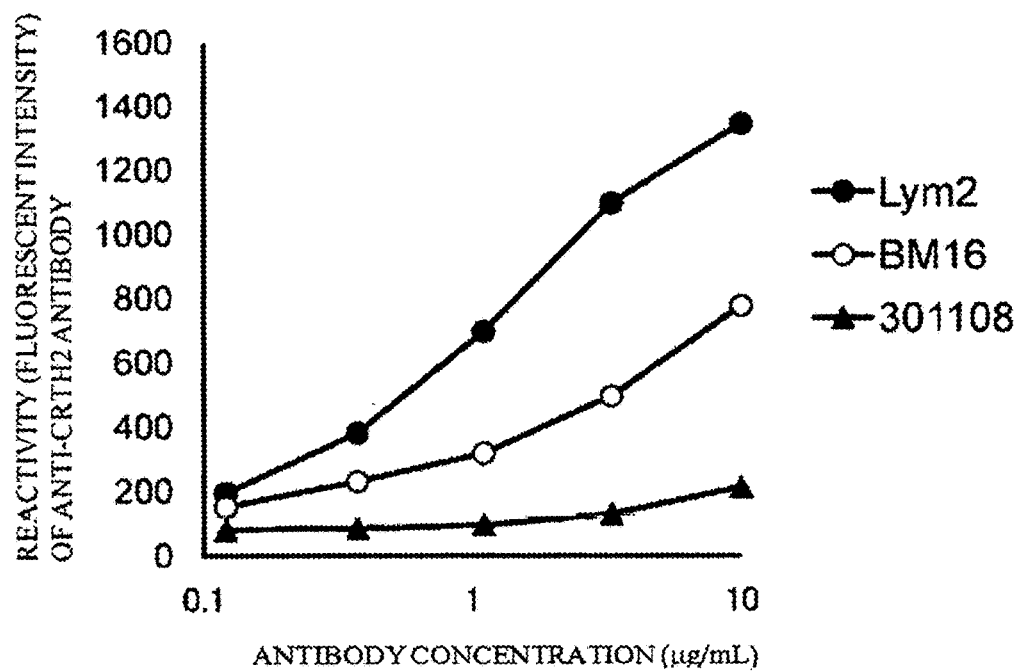

[FIG. 9]
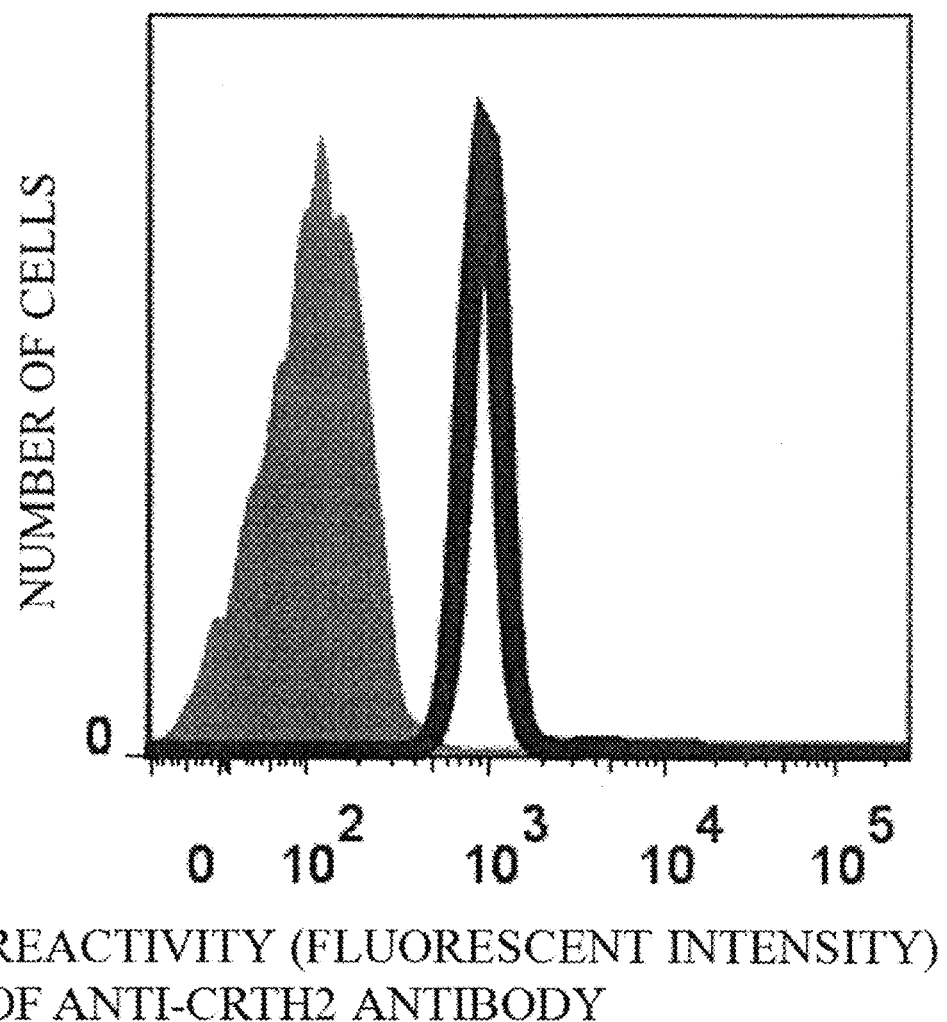

[FIG. 10]
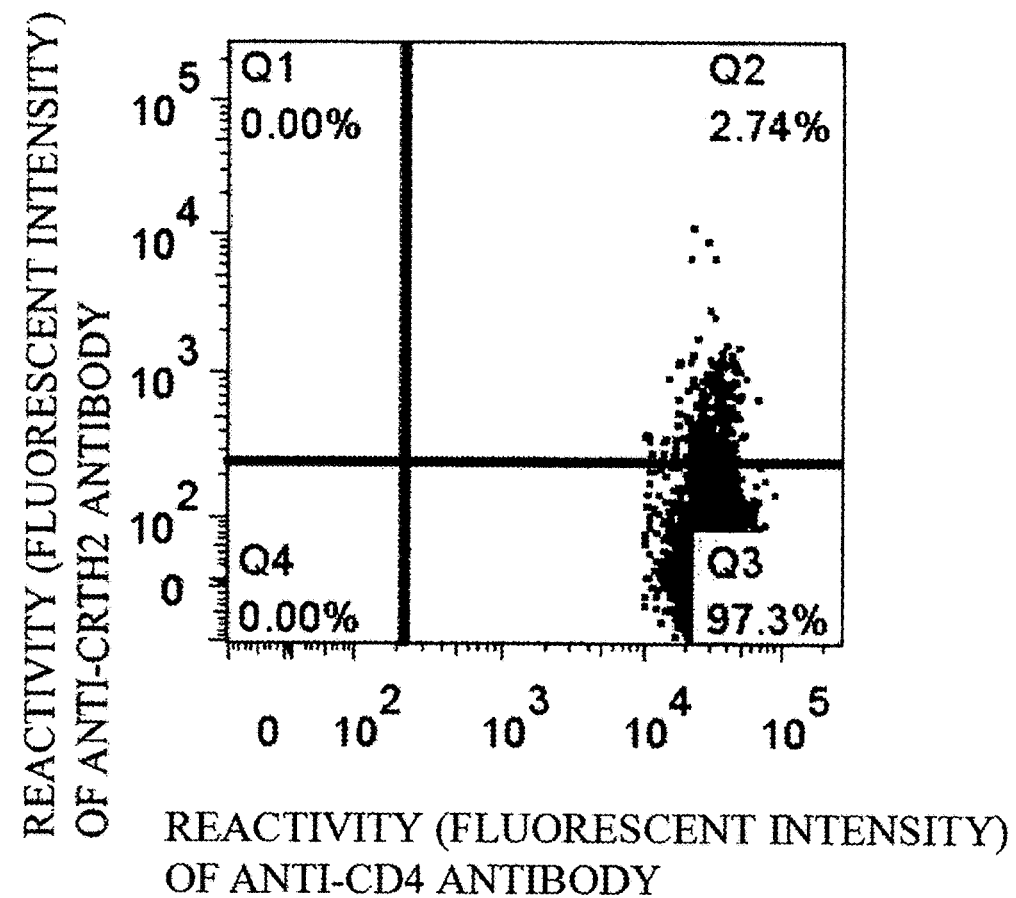

[FIG. 11(A)]
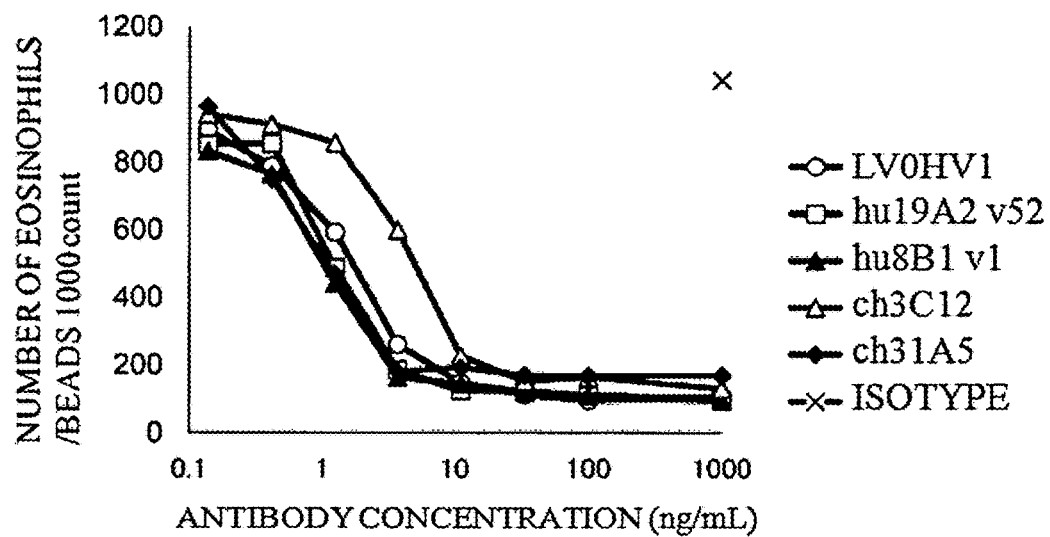
[FIG. 11(B)]
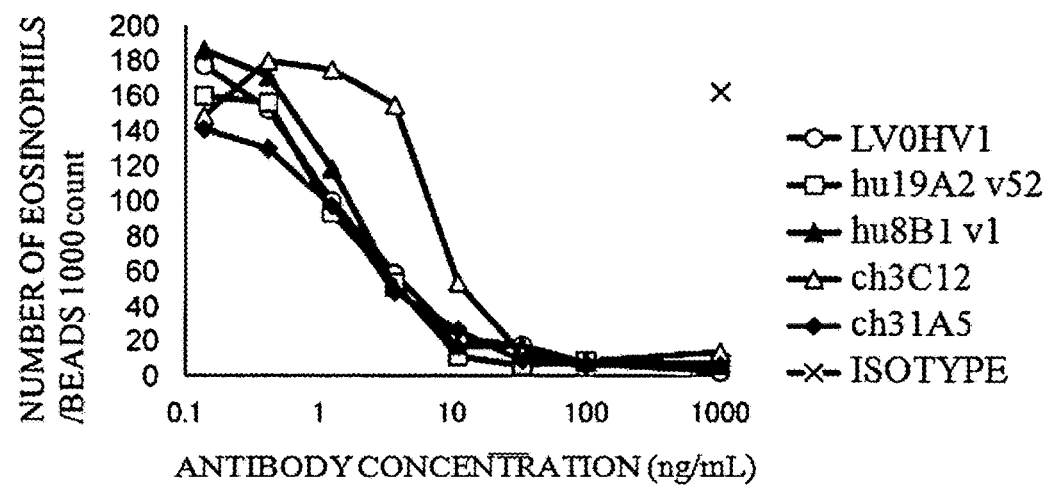

[FIG. 12(A)]
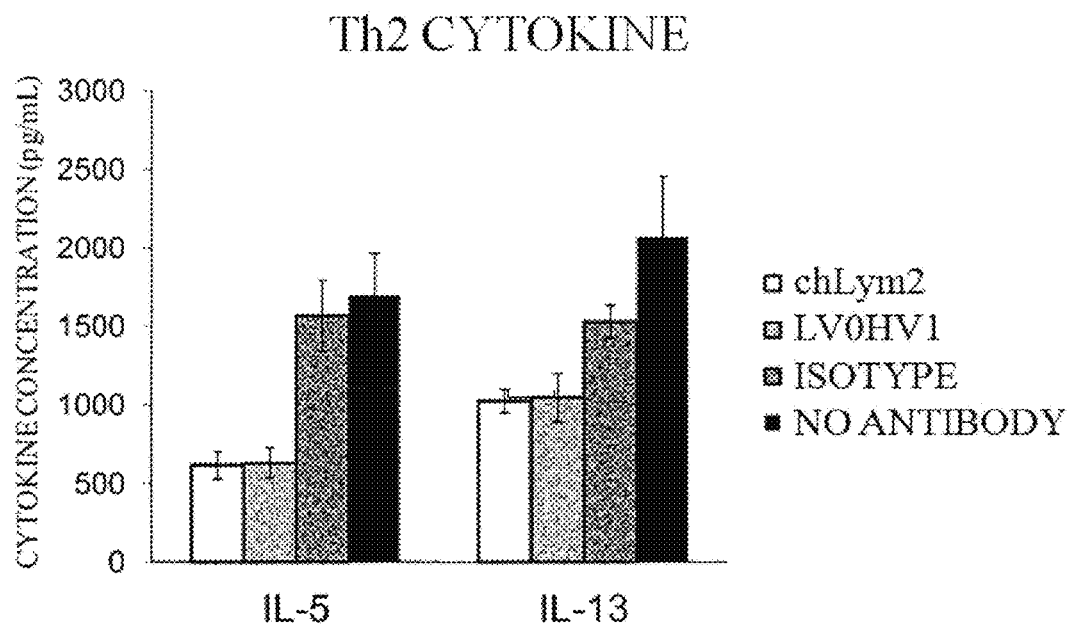
[FIG. 12(B)]
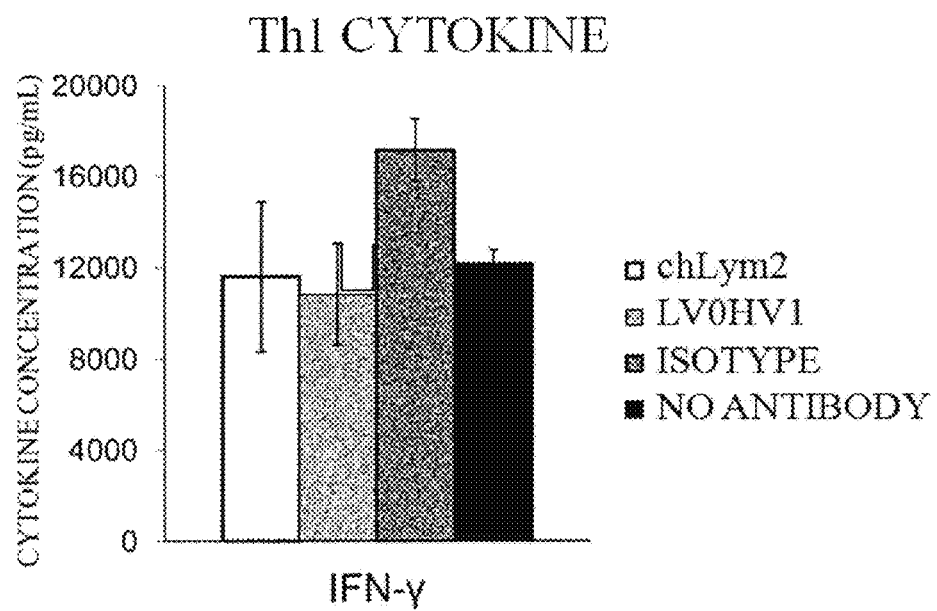

[FIG. 13(A)]
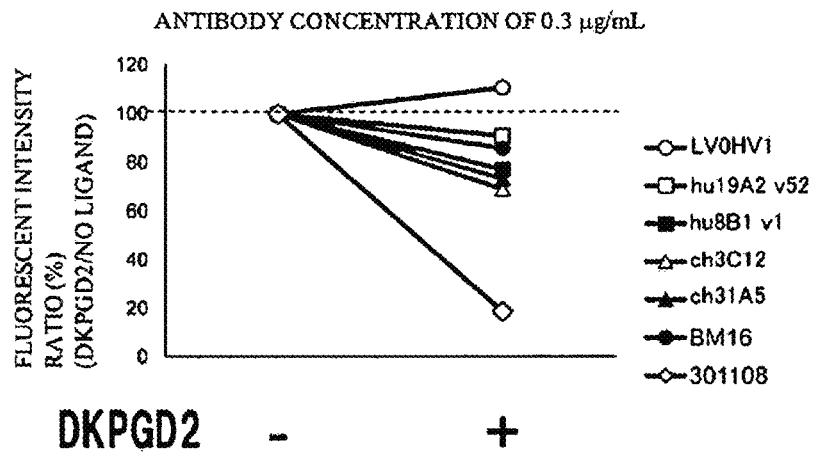
[FIG. 13(B)]
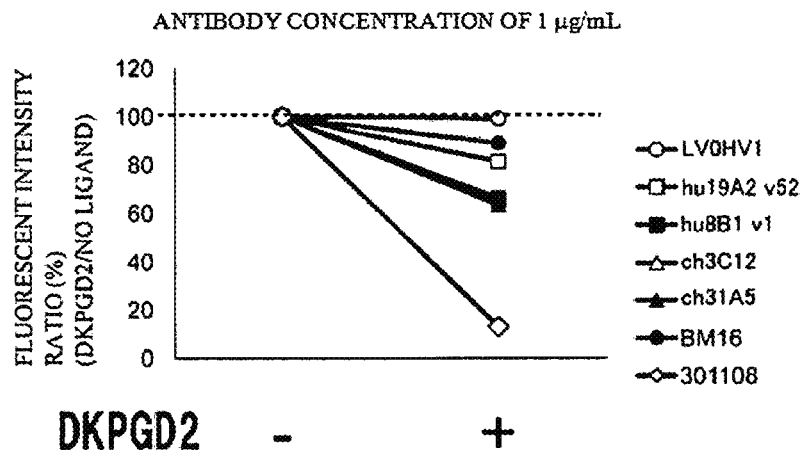
[FIG. 13(C)]
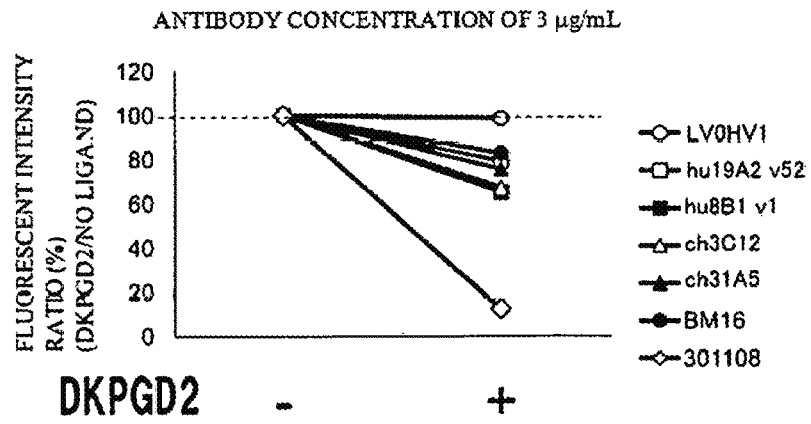

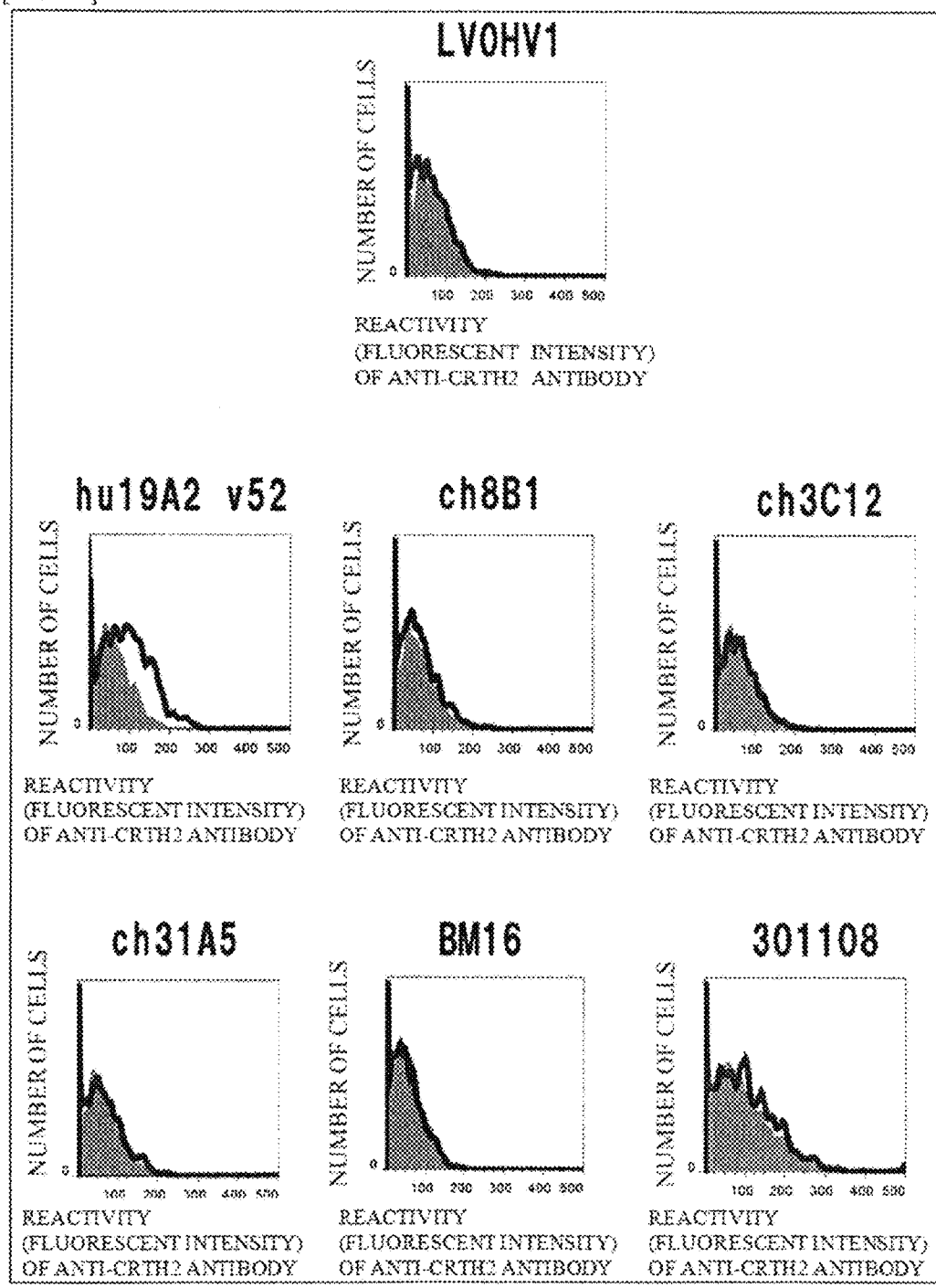
[FIG. 14]

[FIG. 15]
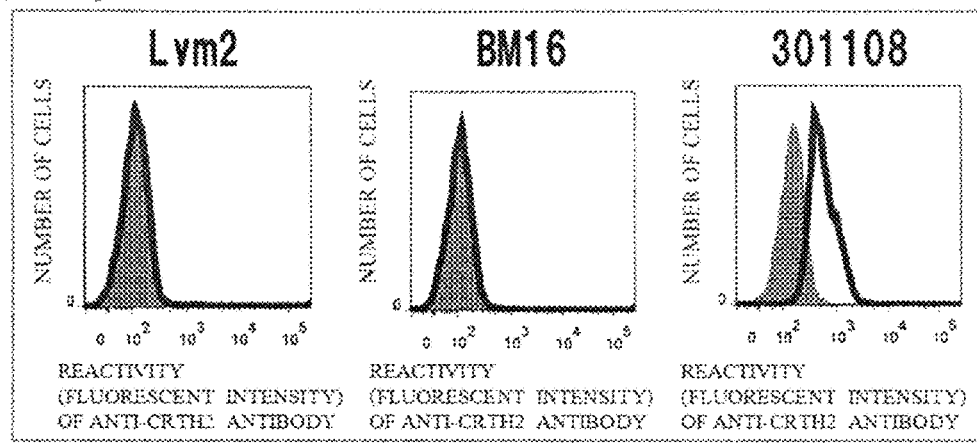
[FIG. 16]
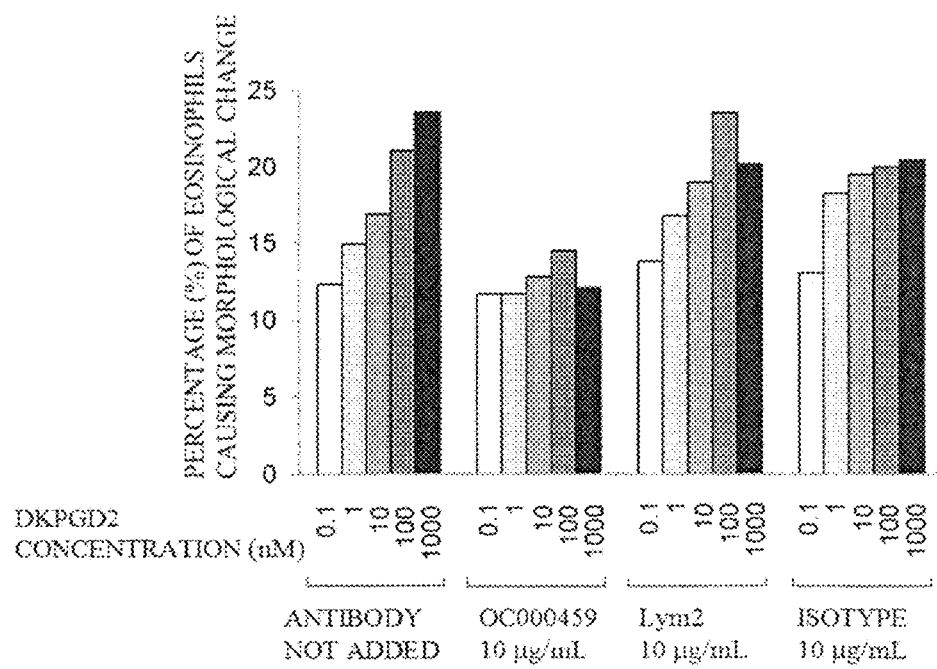

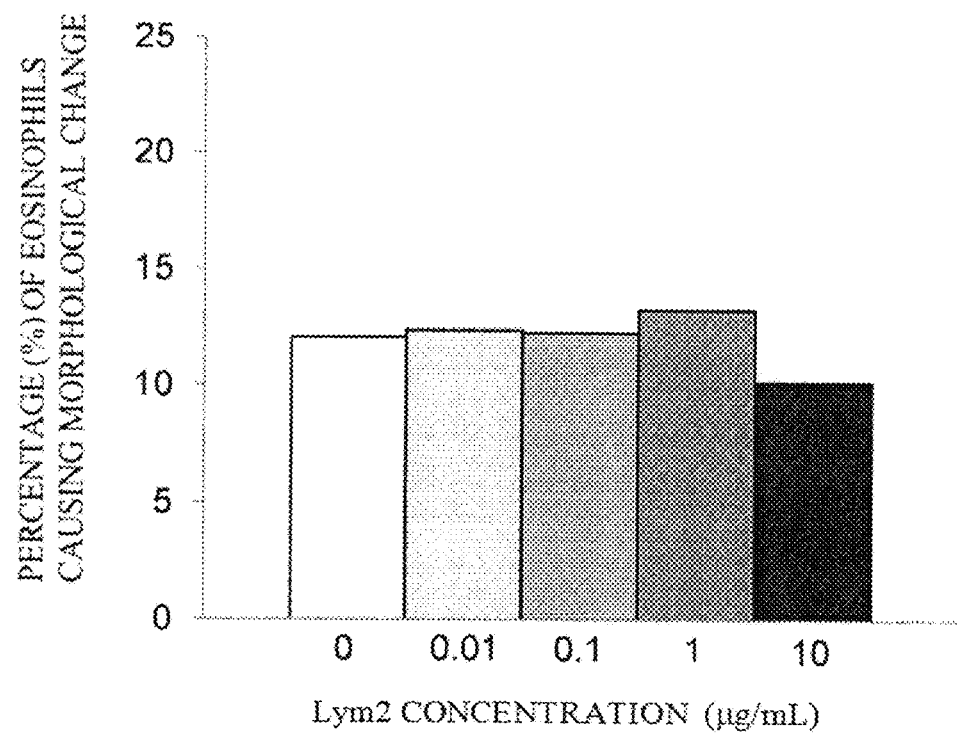
[FIG. 17]

[FIG. 18(A)]
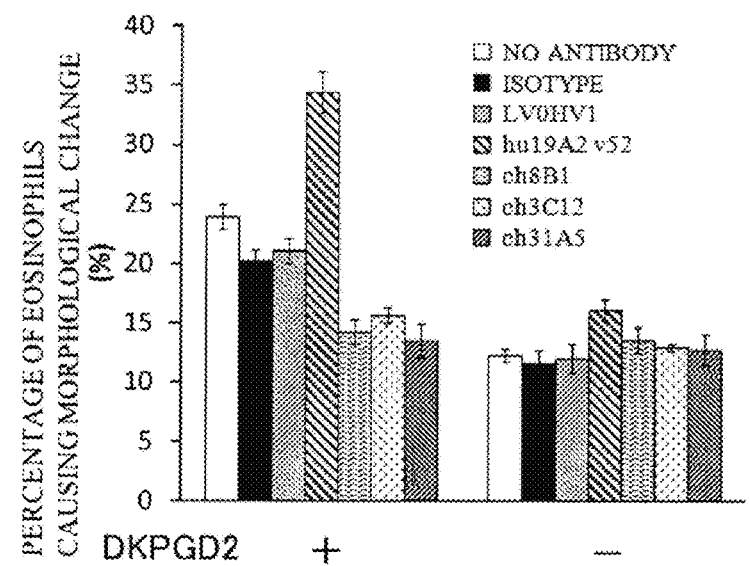
[FIG. 18(B)]
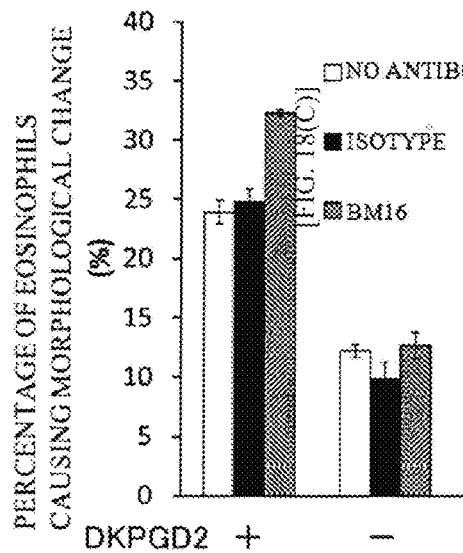
[FIG. 18(C)]
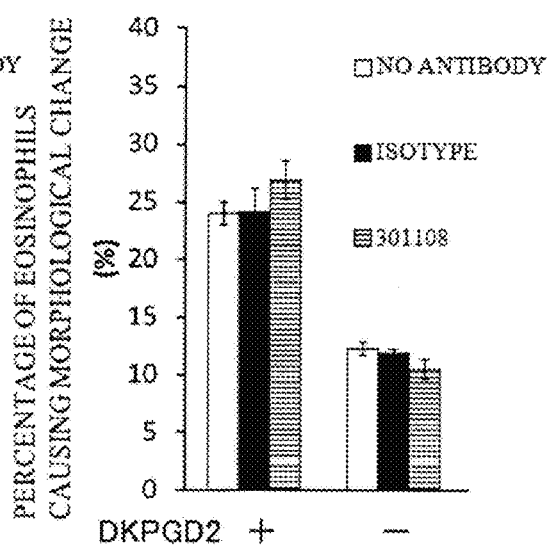

[FIG. 19]
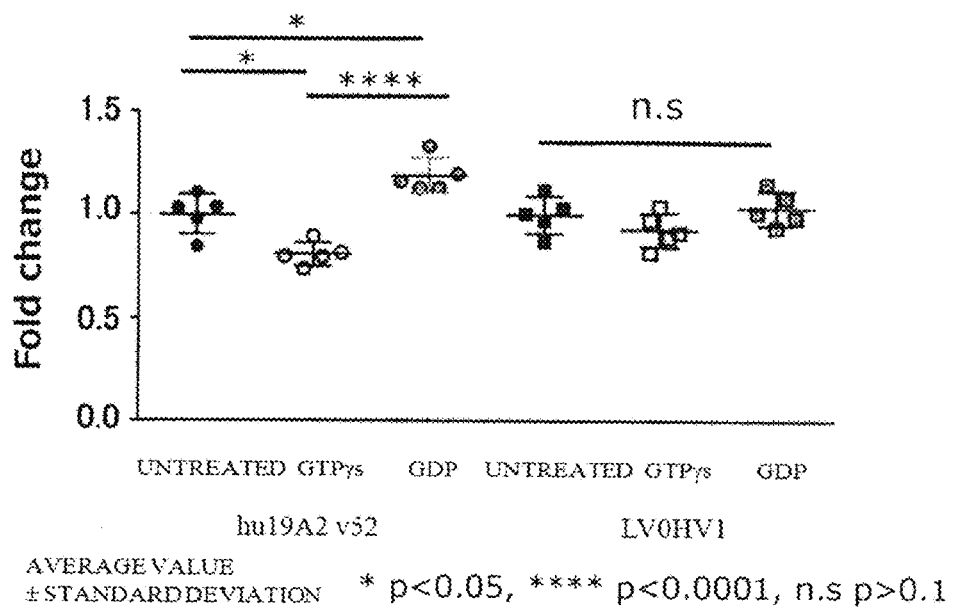
[FIG. 20]
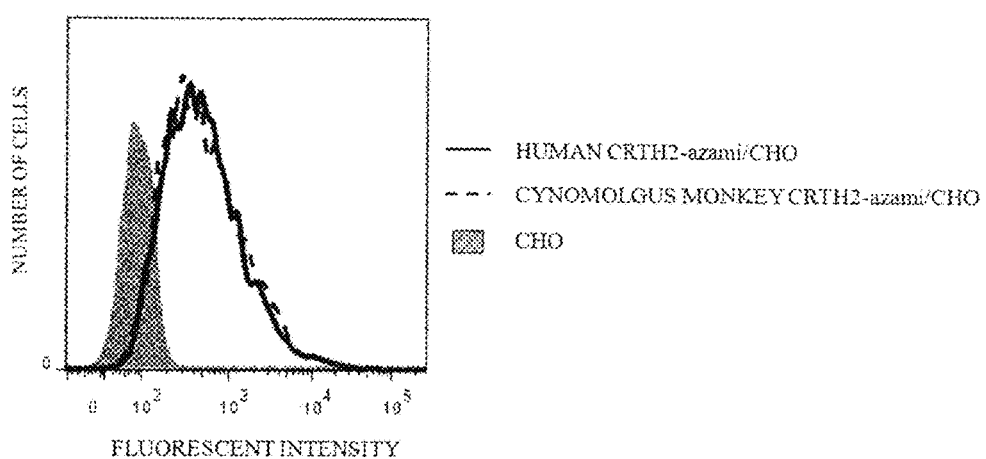

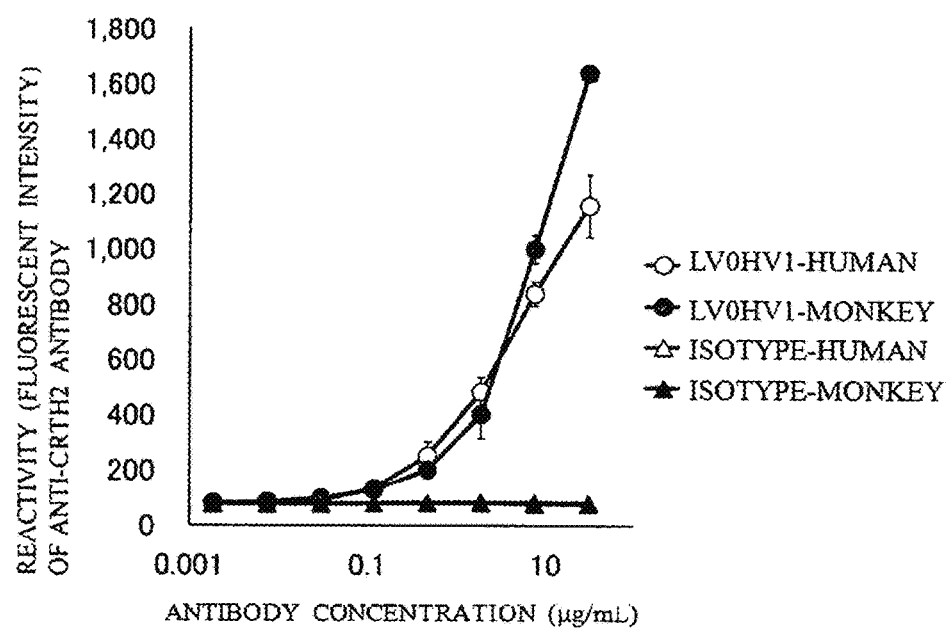
[FIG. 21]

SEQUENCE LISTING

```
<160> NUMBER OF SEQ ID NOS: 65

<210> SEQ ID NO 1
<211> LENGTH: 1188
<212> TYPE: DNA
<213> ORGANISM: Homo sapiens
<220> FEATURE:
<221> NAME/KEY: CDS
<222> LOCATION: (1)..(1188)

<400> SEQUENCE: 1 atg tcg gcc aac gcc aca ctg aag cca ctc tgc ccc atc ctg gag cag      48
Met Ser Ala Asn Ala Thr Leu Lys Pro Leu Cys Pro Ile Leu Glu Gln
1               5                   10                  15 atg agc cgt ctc cag agc cac agc aac acc agc atc cgc tac atc gac      96
Met Ser Arg Leu Gln Ser His Ser Asn Thr Ser Ile Arg Tyr Ile Asp
                20                  25                  30 cac gcg gcc gtg ctg ctc cac ggg ctg gcc tcg ctg ctg ggc ctg gtg     144
His Ala Ala Val Leu Leu His Gly Leu Ala Ser Leu Leu Gly Leu Val
            35                  40                  45 gag aat gga gtc atc ctc ttc gtg gtg ggc tgc cgc atg cgc cag acc     192
Glu Asn Gly Val Ile Leu Phe Val Val Gly Cys Arg Met Arg Gln Thr
        50                  55                  60 gtg gtc acc acc tgg gtg ctg cac ctg gcg ctg tcc gac ctg ttg gcc     240
Val Val Thr Thr Trp Val Leu His Leu Ala Leu Ser Asp Leu Leu Ala
65                  70                  75                  80
```

| | | |
|---|---|---|
| tct gct tcc ctg ccc ttc ttc acc tac ttc ttg gcc gtg ggc cac tcg<br>Ser Ala Ser Leu Pro Phe Phe Thr Tyr Phe Leu Ala Val Gly His Ser<br>                                85                    90                    95 | | 288 |
| tgg gag ctg ggc acc acc ttc tgc aaa ctg cac tcc tcc atc ttc ttt<br>Trp Glu Leu Gly Thr Thr Phe Cys Lys Leu His Ser Ser Ile Phe Phe<br>                 100                  105                110 | | 336 |
| ctc aac atg ttc gcc agc ggc ttc ctc ctc agc gcc atc agc ctg gac<br>Leu Asn Met Phe Ala Ser Gly Phe Leu Leu Ser Ala Ile Ser Leu Asp<br>          115                120                125 | | 384 |
| cgc tgc ctg cag gtg gtg cgg ccg gtg tgg gcg cag aac cac cgc acc<br>Arg Cys Leu Gln Val Val Arg Pro Val Trp Ala Gln Asn His Arg Thr<br>130                  135                140 | | 432 |
| gtg gcc gcg gcg cac aaa gtc tgc ctg gtg ctt tgg gca cta gcg gtg<br>Val Ala Ala Ala His Lys Val Cys Leu Val Leu Trp Ala Leu Ala Val<br>145                  150                155                160 | | 480 |
| ctc aac acg gtg ccc tat ttc gtg ttc cgg gac acc atc tcg cgg ctg<br>Leu Asn Thr Val Pro Tyr Phe Val Phe Arg Asp Thr Ile Ser Arg Leu<br>                 165                  170                175 | | 528 |
| gac ggg cgc att atg tgc tac tac aat gtg ctc ctc ctg aac ccg ggg<br>Asp Gly Arg Ile Met Cys Tyr Tyr Asn Val Leu Leu Leu Asn Pro Gly<br>               180                  185                190 | | 576 |
| cct gac cgc gat gcc acg tgc aac tcg cgg cag gtg gcc ctg gcc gtc<br>Pro Asp Arg Asp Ala Thr Cys Asn Ser Arg Gln Val Ala Leu Ala Val<br>         195                200                205 | | 624 |
| agc aag ttc ctg ctg gcc ttc ctg gtg ccg ctg gcg atc atc gcc tcg<br>Ser Lys Phe Leu Leu Ala Phe Leu Val Pro Leu Ala Ile Ile Ala Ser<br>          210                215                220 | | 672 |
| agc cac gcg gcc gtg agc ctg cgg ttg cag cac cgc ggc cgc cgg cgg<br>Ser His Ala Ala Val Ser Leu Arg Leu Gln His Arg Gly Arg Arg Arg<br>225                  230                235                240 | | 720 |
| cca ggc cgc ttc gtg cgc ctg gtg gcg gcc gtc gtg gcc gcc ttc gcg<br>Pro Gly Arg Phe Val Arg Leu Val Ala Ala Val Val Ala Ala Phe Ala<br>                 245                  250                255 | | 768 |
| ctc tgc tgg ggg ccc tac cac gtg ttc agc ctg ctg gag gcg cgg gcg<br>Leu Cys Trp Gly Pro Tyr His Val Phe Ser Leu Leu Glu Ala Arg Ala<br>               260                  265                270 | | 816 |
| cac gca aac ccg ggg ctg cgg ccg ctc gtg tgg cgc ggg ctg ccc ttc<br>His Ala Asn Pro Gly Leu Arg Pro Leu Val Trp Arg Gly Leu Pro Phe<br>         275                280                285 | | 864 |
| gtc acc agc ctg gcc ttc ttc aac agc gtg gcc aac ccg gtg ctc tac<br>Val Thr Ser Leu Ala Phe Phe Asn Ser Val Ala Asn Pro Val Leu Tyr<br>         290                295                300 | | 912 |
| gtg ctc acc tgc ccc gac atg ctg cgc aag ctg cgg cgc tcg ctg cgc<br>Val Leu Thr Cys Pro Asp Met Leu Arg Lys Leu Arg Arg Ser Leu Arg<br>305                  310                315                320 | | 960 |
| acg gtg ctg gag agc gtg ctg gtg gac gac agc gag ctg ggt ggc gcg<br>Thr Val Leu Glu Ser Val Leu Val Asp Asp Ser Glu Leu Gly Gly Ala<br>                 325                  330                335 | | 1008 |
| gga agc agc cgc cgc cgc cgc acc tcc tcc acc gcc cgc tcg gcc tcc<br>Gly Ser Ser Arg Arg Arg Arg Thr Ser Ser Thr Ala Arg Ser Ala Ser<br>               340                  345                350 | | 1056 |
| cct tta gct ctc tgc agc cgc ccg gag gaa ccg cgg ggc ccc gcg cgt<br>Pro Leu Ala Leu Cys Ser Arg Pro Glu Glu Pro Arg Gly Pro Ala Arg<br>         355                360                365 | | 1104 |
| ctc ctc ggc tgg ctg ctg ggc agc tgc gca gcg tcc ccg cag acg ggc<br>Leu Leu Gly Trp Leu Leu Gly Ser Cys Ala Ala Ser Pro Gln Thr Gly<br>         370                375                380 | | 1152 |
| ccc ctg aac cgg gcg ctg agc agc acc tcg agt tag<br>Pro Leu Asn Arg Ala Leu Ser Ser Thr Ser Ser<br>385                  390                395 | | 1188 |

<210> SEQ ID NO 2
<211> LENGTH: 395
<212> TYPE: PRT
<213> ORGANISM: Homo sapiens

<400> SEQUENCE: 2

Met Ser Ala Asn Ala Thr Leu Lys Pro Leu Cys Pro Ile Leu Glu Gln
1               5                   10                  15

Met Ser Arg Leu Gln Ser His Ser Asn Thr Ser Ile Arg Tyr Ile Asp
            20                  25                  30

His Ala Ala Val Leu Leu His Gly Leu Ala Ser Leu Leu Gly Leu Val
        35                  40                  45

Glu Asn Gly Val Ile Leu Phe Val Val Gly Cys Arg Met Arg Gln Thr
    50                  55                  60

Val Val Thr Thr Trp Val Leu His Leu Ala Leu Ser Asp Leu Leu Ala
65                  70                  75                  80

Ser Ala Ser Leu Pro Phe Phe Thr Tyr Phe Leu Ala Val Gly His Ser
                85                  90                  95

Trp Glu Leu Gly Thr Thr Phe Cys Lys Leu His Ser Ser Ile Phe Phe
            100                 105                 110

Leu Asn Met Phe Ala Ser Gly Phe Leu Leu Ser Ala Ile Ser Leu Asp
        115                 120                 125

Arg Cys Leu Gln Val Val Arg Pro Val Trp Ala Gln Asn His Arg Thr
    130                 135                 140

Val Ala Ala Ala His Lys Val Cys Leu Val Leu Trp Ala Leu Ala Val
145                 150                 155                 160

Leu Asn Thr Val Pro Tyr Phe Val Phe Arg Asp Thr Ile Ser Arg Leu
                165                 170                 175

Asp Gly Arg Ile Met Cys Tyr Tyr Asn Val Leu Leu Leu Asn Pro Gly
            180                 185                 190

Pro Asp Arg Asp Ala Thr Cys Asn Ser Arg Gln Val Ala Leu Ala Val
        195                 200                 205

Ser Lys Phe Leu Leu Ala Phe Leu Val Pro Leu Ala Ile Ile Ala Ser
    210                 215                 220

Ser His Ala Ala Val Ser Leu Arg Leu Gln His Arg Gly Arg Arg Arg
225                 230                 235                 240

Pro Gly Arg Phe Val Arg Leu Val Ala Val Val Ala Ala Phe Ala
        245                 250                 255

Leu Cys Trp Gly Pro Tyr His Val Phe Ser Leu Leu Glu Ala Arg Ala
        260                 265                 270

His Ala Asn Pro Gly Leu Arg Pro Leu Val Trp Arg Gly Leu Pro Phe
    275                 280                 285

Val Thr Ser Leu Ala Phe Phe Asn Ser Val Ala Asn Pro Val Leu Tyr
290                 295                 300

Val Leu Thr Cys Pro Asp Met Leu Arg Lys Leu Arg Arg Ser Leu Arg
305                 310                 315                 320

Thr Val Leu Glu Ser Val Leu Val Asp Asp Ser Glu Leu Gly Gly Ala
                325                 330                 335

Gly Ser Ser Arg Arg Arg Thr Ser Ser Thr Ala Arg Ser Ala Ser
            340                 345                 350

Pro Leu Ala Leu Cys Ser Arg Pro Glu Glu Pro Arg Gly Pro Ala Arg
        355                 360                 365

Leu Leu Gly Trp Leu Leu Gly Ser Cys Ala Ala Ser Pro Gln Thr Gly

Pro Leu Asn Arg Ala Leu Ser Ser Thr Ser Ser
385                 390                 395

<210> SEQ ID NO 3
<211> LENGTH: 27
<212> TYPE: DNA
<213> ORGANISM: Artificial
<220> FEATURE:
<223> OTHER INFORMATION: description of the artificial sequence: human
      CRTH2 FLAG-A

<400> SEQUENCE: 3
cataagcttg ccaccatgtc ggccaac                                        27

<210> SEQ ID NO 4
<211> LENGTH: 66
<212> TYPE: DNA
<213> ORGANISM: Artificial
<220> FEATURE:
<223> OTHER INFORMATION: description of the artificial sequence: human
      CRTH2 FLAG-B

<400> SEQUENCE: 4
catggtaccc tacttatcgt cgtcatcctt gtaatcactc gaggtgctgc tcagcgcccg    60
gttcag                                                              66

<210> SEQ ID NO 5
<211> LENGTH: 1212
<212> TYPE: DNA
<213> ORGANISM: Artificial
<220> FEATURE:
<223> OTHER INFORMATION: description of the artificial sequence: FLAG
      tagged human CRTH2 cDNA

<400> SEQUENCE: 5
atgtcggcca acgccacact gaagccactc tgccccatcc tggagcagat gagccgtctc    60
cagagccaca gcaacaccag catccgctac atcgaccacg cggccgtgct gctgcacggg   120
ctggcctcgc tgctgggcct ggtggagaat ggagtcatcc tcttcgtggt gggctgccgc   180
atgcgccaga ccgtggtcac cacctgggtg ctgcacctgg cgctgtccga cctgttggcc   240
tctgcttccc tgcccttctt cacctacttc ttggccgtgg ccactcgtg ggagctgggc   300 accaccttct gcaaactgca ctcctccatc ttctttctca acatgttcgc cagcggcttc   360
ctgctcagcg ccatcagcct ggaccgctgc ctgcaggtgg tgcggccggt gtgggcgcag   420
aaccaccgca ccgtggccgc ggcgcacaaa gtctgcctgg tgctttgggc actagcggtg   480
ctcaacacgg tgccctattt cgtgttccgg gacaccatct cgcggctgga cgggcgcatt   540
atgtgctact acaatgtgct gctcctgaac ccggggcctg accgcgatgc cacgtgcaac   600
tcgcggcagg tggccctggc cgtcagcaag ttcctgctgg ccttcctggt gccgctggcg   660
atcatcgcct cgagccacgc ggccgtgagc ctgcggttgc agcaccgcgg ccgccggcgg   720
ccaggccgct tcgtgcgcct ggtggcggcc gtcgtggccg ccttcgcgct ctgctggggg   780
ccctaccacg tgttcagcct gctggaggcg cgggcgcacg caaacccggg gctgcggccc   840
ctcgtgtggc gcgggctgcc cttcgtcacc agcctggcct tcttcaacag cgtggccaac   900
ccggtgctct acgtgctcac ctgccccgac atgctgcgca agctgcggcg ctcgctgcgc   960
acggtgctgg agagcgtgct ggtggacgac agcgagctgg gtggcgcggg aagcagccgc  1020
cgccgccgca cctcctccac cgcccgctcg gcctcccctt tagctctctg cagccgcccg  1080

```
gaggaaccgc ggggccccgc gcgtctcctc ggctggctgc tgggcagctg cgcagcgtcc    1140
ccgcagacgg gccccctgaa ccgggcgctg agcagcacct cgagtgatta caaggatgac    1200
gacgataagt ag                                                        1212
```

<210> SEQ ID NO 6
<211> LENGTH: 27
<212> TYPE: DNA
<213> ORGANISM: Artificial
<220> FEATURE:
<223> OTHER INFORMATION: description of the artificial sequence: human
      CRTH2 FLAG-C

<400> SEQUENCE: 6

```
catgaattcg ccaccatgtc ggccaac                                        27
```

<210> SEQ ID NO 7
<211> LENGTH: 27
<212> TYPE: DNA
<213> ORGANISM: Artificial
<220> FEATURE:
<223> OTHER INFORMATION: description of the artificial sequence: human
      CRTH2 FLAG-D

<400> SEQUENCE: 7

```
catggtaccc tacttatcgt cgtcatc                                        27
```

<210> SEQ ID NO 8
<211> LENGTH: 24
<212> TYPE: DNA
<213> ORGANISM: Artificial
<220> FEATURE:
<223> OTHER INFORMATION: description of the artificial sequence:
      RatIgG2bH-A

<400> SEQUENCE: 8

```
cgctggacag ggctccagag ttcc                                           24
```

<210> SEQ ID NO 9
<211> LENGTH: 28
<212> TYPE: DNA
<213> ORGANISM: Artificial
<220> FEATURE:
<223> OTHER INFORMATION: description of the artificial sequence:
      RatIgG2bH-B

<400> SEQUENCE: 9

```
gggcatgtag ggcatttgtg tccaatgc                                       28
```

<210> SEQ ID NO 10
<211> LENGTH: 31
<212> TYPE: DNA
<213> ORGANISM: Artificial
<220> FEATURE:
<223> OTHER INFORMATION: description of the artificial sequence: Ratk-A

<400> SEQUENCE: 10

```
gactgaggca cctccagttg ctaactgttc c                                   31
```

<210> SEQ ID NO 11
<211> LENGTH: 29
<212> TYPE: DNA
<213> ORGANISM: Artificial
<220> FEATURE:
<223> OTHER INFORMATION: description of the artificial sequence: Ratk-B

<400> SEQUENCE: 11
cctgttgaag ctcttgacga cgggtgagg                                              29

<210> SEQ ID NO 12
<211> LENGTH: 426
<212> TYPE: DNA
<213> ORGANISM: Rattus norvegicus
<220> FEATURE:
<221> NAME/KEY: CDS
<222> LOCATION: (1)..(426)

<400> SEQUENCE: 12

| atg gac atc agg ctc agc ttg gct ttc ctt gtc ctt ttc ata aaa ggt | 48 |
| Met Asp Ile Arg Leu Ser Leu Ala Phe Leu Val Leu Phe Ile Lys Gly | |
| 1               5                   10                  15     | |

| gtc cag tgt gag gtg cag ctg gtg gag tct ggg gga ggc tta gtg cag | 96 |
| Val Gln Cys Glu Val Gln Leu Val Glu Ser Gly Gly Gly Leu Val Gln | |
|         20                  25                  30             | |

| cct gga agg tcc atg aaa ctc tcc tgt gca gcc tca gga ttc act ttc | 144 |
| Pro Gly Arg Ser Met Lys Leu Ser Cys Ala Ala Ser Gly Phe Thr Phe | |
|             35                  40                  45         | |

| agt aac tat tac atg gcc tgg gtc cgc cag gct cca aag aag ggt ctg | 192 |
| Ser Asn Tyr Tyr Met Ala Trp Val Arg Gln Ala Pro Lys Lys Gly Leu | |
| 50                  55                  60                     | |

| gag tgg gtc gca acc att agt tat gat ggt agt agc act tac tat cga | 240 |
| Glu Trp Val Ala Thr Ile Ser Tyr Asp Gly Ser Ser Thr Tyr Tyr Arg | |
| 65                  70                  75                  80 | |

| gac tcc gtg aag ggc cga ttc act atc tcc aga gat aat gca aaa agc | 288 |
| Asp Ser Val Lys Gly Arg Phe Thr Ile Ser Arg Asp Asn Ala Lys Ser | |
|                 85                  90                  95     | |

| acc cta tac ctg caa atg gac agt ctg agg tct gag gac acg gcc act | 336 |
| Thr Leu Tyr Leu Gln Met Asp Ser Leu Arg Ser Glu Asp Thr Ala Thr | |
|             100                 105                 110        | |

| tat tac tgt gca aga cat cgg ggt tat tac tac agt ggg gcg ggg tac | 384 |
| Tyr Tyr Cys Ala Arg His Arg Gly Tyr Tyr Tyr Ser Gly Ala Gly Tyr | |
|         115                 120                 125            | |

| ttt gat tac tgg ggc caa gga gtc atg gtc aca gtc tcc tca         | 426 |
| Phe Asp Tyr Trp Gly Gln Gly Val Met Val Thr Val Ser Ser         | |
|     130                 135                 140                | |

<210> SEQ ID NO 13
<211> LENGTH: 142
<212> TYPE: PRT
<213> ORGANISM: Rattus norvegicus

<400> SEQUENCE: 13

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Met Lys Leu Ser Cys Ala Ala Ser Gly Phe Thr Phe
        35                  40                  45

Ser Asn Tyr Tyr Met Ala Trp Val Arg Gln Ala Pro Lys Lys Gly Leu
    50                  55                  60

Glu Trp Val Ala Thr Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Arg His Arg Gly Tyr Tyr Ser Gly Ala Gly Tyr
        115                 120                 125

Phe Asp Tyr Trp Gly Gln Gly Val Met Val Thr Val Ser Ser
    130                 135                 140

<210> SEQ ID NO 14
<211> LENGTH: 393
<212> TYPE: DNA
<213> ORGANISM: Rattus norvegicus
<220> FEATURE:
<221> NAME/KEY: CDS
<222> LOCATION: (1)..(393)

<400> SEQUENCE: 14

```
atg aaa gtg cct ggt agg ctg ctg gtg ctg ttg ttt tgg att cca gct      48
Met Lys Val Pro Gly Arg Leu Leu Val Leu Leu Phe Trp Ile Pro Ala
1               5                   10                  15 tcc agg agt gat gtt gtg ttg aca caa act cca gtt tcc ctg tct gtc      96
Ser Arg Ser Asp Val Val Leu Thr Gln Thr Pro Val Ser Leu Ser Val
                20                  25                  30 aca ctt gga gat caa gct tct ata tct tgc agg tct agt cag agc ctg     144
Thr Leu Gly Asp Gln Ala Ser Ile Ser Cys Arg Ser Ser Gln Ser Leu
            35                  40                  45 gaa tat agt gat gga tac act tat ttg gaa tgg tac cta cag aag cca     192
Glu Tyr Ser Asp Gly Tyr Thr Tyr Leu Glu Trp Tyr Leu Gln Lys Pro
        50                  55                  60 ggc cag tct cca cag gtc ctc atc tat gga gtt tcc aac cga ttt tct     240
Gly Gln Ser Pro Gln Val Leu Ile Tyr Gly Val Ser Asn Arg Phe Ser
65                  70                  75                  80 ggg gtc cca gac agg ttc att ggc agt ggg tca ggg aca gat ttc acc     288
Gly Val Pro Asp Arg Phe Ile Gly Ser Gly Ser Gly Thr Asp Phe Thr
                85                  90                  95 ctc aag atc agc aga gta gag cct gag gac ttg gga gtt tat tac tgc     336
Leu Lys Ile Ser Arg Val Glu Pro Glu Asp Leu Gly Val Tyr Tyr Cys
            100                 105                 110 ttc caa gct aca cat gat cct ctc acg ttc ggc tca ggg acg aag ttg     384
Phe Gln Ala Thr His Asp Pro Leu Thr Phe Gly Ser Gly Thr Lys Leu
        115                 120                 125 gaa ata aaa                                                          393
Glu Ile Lys
    130
```

<210> SEQ ID NO 15
<211> LENGTH: 131
<212> TYPE: PRT
<213> ORGANISM: Rattus norvegicus

<400> SEQUENCE: 15

Met Lys Val Pro Gly Arg Leu Leu Val Leu Leu Phe Trp Ile Pro Ala
1               5                   10                  15

Ser Arg Ser Asp Val Val Leu Thr Gln Thr Pro Val Ser Leu Ser Val
                20                  25                  30

Thr Leu Gly Asp Gln Ala Ser Ile Ser Cys Arg Ser Ser Gln Ser Leu
            35                  40                  45

Glu Tyr Ser Asp Gly Tyr Thr Tyr Leu Glu Trp Tyr Leu Gln Lys Pro
        50                  55                  60

Gly Gln Ser Pro Gln Val Leu Ile Tyr Gly Val Ser Asn Arg Phe Ser
65                  70                  75                  80

Gly Val Pro Asp Arg Phe Ile Gly Ser Gly Ser Gly Thr Asp Phe Thr
                85                  90                  95

Leu Lys Ile Ser Arg Val Glu Pro Glu Asp Leu Gly Val Tyr Tyr Cys
            100                 105                 110

Phe Gln Ala Thr His Asp Pro Leu Thr Phe Gly Ser Gly Thr Lys Leu
            115                 120                 125

Glu Ile Lys
    130

<210> SEQ ID NO 16
<211> LENGTH: 369
<212> TYPE: DNA
<213> ORGANISM: Rattus norvegicus
<220> FEATURE:
<221> NAME/KEY: CDS
<222> LOCATION: (1)..(369)

<400> SEQUENCE: 16

```
gag gtg cag ctg gtg gag tct ggg gga ggc tta gtg cag cct gga agg      48
Glu Val Gln Leu Val Glu Ser Gly Gly Gly Leu Val Gln Pro Gly Arg
1               5                   10                  15 tcc atg aaa ctc tcc tgt gca gcc tca gga ttc act ttc agt aac tat      96
Ser Met Lys Leu Ser Cys Ala Ala Ser Gly Phe Thr Phe Ser Asn Tyr
            20                  25                  30 tac atg gcc tgg gtc cgc cag gct cca aag aag ggt ctg gag tgg gtc     144
Tyr Met Ala Trp Val Arg Gln Ala Pro Lys Lys Gly Leu Glu Trp Val
        35                  40                  45 gca acc att agt tat gat ggt agt agc act tac tat cga gac tcc gtg     192
Ala Thr Ile Ser Tyr Asp Gly Ser Ser Thr Tyr Tyr Arg Asp Ser Val
    50                  55                  60 aag ggc cga ttc act atc tcc aga gat aat gca aaa agc acc cta tac     240
Lys Gly Arg Phe Thr Ile Ser Arg Asp Asn Ala Lys Ser Thr Leu Tyr
65                  70                  75                  80 ctg caa atg gac agt ctg agg tct gag gac acg gcc act tat tac tgt     288
Leu Gln Met Asp Ser Leu Arg Ser Glu Asp Thr Ala Thr Tyr Tyr Cys
                85                  90                  95 gca aga cat cgg ggt tat tac tac agt ggg gcg ggg tac ttt gat tac     336
Ala Arg His Arg Gly Tyr Tyr Tyr Ser Gly Ala Gly Tyr Phe Asp Tyr
            100                 105                 110 tgg ggc caa gga gtc atg gtc aca gtc tcc tca                         369
Trp Gly Gln Gly Val Met Val Thr Val Ser Ser
        115                 120
```

<210> SEQ ID NO 17
<211> LENGTH: 123
<212> TYPE: PRT
<213> ORGANISM: Rattus norvegicus

<400> SEQUENCE: 17

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Ser Asn Tyr
            20                  25                  30

Tyr Met Ala Trp Val Arg Gln Ala Pro Lys Lys Gly Leu Glu Trp Val
        35                  40                  45

Ala Thr Ile Ser Tyr Asp Gly Ser Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

```
          Ala Arg His Arg Gly Tyr Tyr Tyr Ser Gly Ala Gly Tyr Phe Asp Tyr
                          100                 105                 110

Trp Gly Gln Gly Val Met Val Thr Val Ser Ser
                  115                 120

<210> SEQ ID NO 18
<211> LENGTH: 336
<212> TYPE: DNA
<213> ORGANISM: Rattus norvegicus
<220> FEATURE:
<221> NAME/KEY: CDS
<222> LOCATION: (1)..(336)

<400> SEQUENCE: 18 gat gtt gtg ttg aca caa act cca gtt tcc ctg tct gtc aca ctt gga       48
Asp Val Val Leu Thr Gln Thr Pro Val Ser Leu Ser Val Thr Leu Gly
1               5                   10                  15 gat caa gct tct ata tct tgc agg tct agt cag agc ctg gaa tat agt       96
Asp Gln Ala Ser Ile Ser Cys Arg Ser Ser Gln Ser Leu Glu Tyr Ser
            20                  25                  30 gat gga tac act tat ttg gaa tgg tac cta cag aag cca ggc cag tct      144
Asp Gly Tyr Thr Tyr Leu Glu Trp Tyr Leu Gln Lys Pro Gly Gln Ser
        35                  40                  45 cca cag gtc ctc atc tat gga gtt tcc aac cga ttt tct ggg gtc cca      192
Pro Gln Val Leu Ile Tyr Gly Val Ser Asn Arg Phe Ser Gly Val Pro
    50                  55                  60 gac agg ttc att ggc agt ggg tca ggg aca gat ttc acc ctc aag atc      240
Asp Arg Phe Ile Gly Ser Gly Ser Gly Thr Asp Phe Thr Leu Lys Ile
65                  70                  75                  80 agc aga gta gag cct gag gac ttg gga gtt tat tac tgc ttc caa gct      288
Ser Arg Val Glu Pro Glu Asp Leu Gly Val Tyr Tyr Cys Phe Gln Ala
                85                  90                  95 aca cat gat cct ctc acg ttc ggc tca ggg acg aag ttg gaa ata aaa      336
Thr His Asp Pro Leu Thr Phe Gly Ser Gly Thr Lys Leu Glu Ile Lys
            100                 105                 110

<210> SEQ ID NO 19
<211> LENGTH: 112
<212> TYPE: PRT
<213> ORGANISM: Rattus norvegicus

<400> SEQUENCE: 19

Asp Val Val Leu Thr Gln Thr Pro Val Ser Leu Ser Val Thr Leu Gly
1               5                   10                  15

Asp Gln Ala Ser Ile Ser Cys Arg Ser Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Val Leu Ile Tyr Gly Val Ser Asn Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asp Pro Leu Thr Phe Gly Ser Gly Thr Lys Leu Glu Ile Lys
            100                 105                 110

<210> SEQ ID NO 20
<211> LENGTH: 5
<212> TYPE: PRT
<213> ORGANISM: Artificial
```

```
<220> FEATURE:
<223> OTHER INFORMATION: description of the artificial sequence: Lym2
      VH CDR1 amino acid

<400> SEQUENCE: 20

Asn Tyr Tyr Met Ala
1               5

<210> SEQ ID NO 21
<211> LENGTH: 17
<212> TYPE: PRT
<213> ORGANISM: Artificial
<220> FEATURE:
<223> OTHER INFORMATION: description of the artificial sequence: Lym2
      VH CDR2 amino acid

<400> SEQUENCE: 21

Thr Ile Ser Tyr Asp Gly Ser Ser Thr Tyr Tyr Arg Asp Ser Val Lys
1               5                   10                  15
Gly

<210> SEQ ID NO 22
<211> LENGTH: 14
<212> TYPE: PRT
<213> ORGANISM: Artificial
<220> FEATURE:
<223> OTHER INFORMATION: description of the artificial sequence: Lym2
      VH CDR3 amino acid

<400> SEQUENCE: 22

His Arg Gly Tyr Tyr Tyr Ser Gly Ala Gly Tyr Phe Asp Tyr
1               5                   10

<210> SEQ ID NO 23
<211> LENGTH: 16
<212> TYPE: PRT
<213> ORGANISM: Artificial
<220> FEATURE:
<223> OTHER INFORMATION: description of the artificial sequence: Lym2
      VL CDR1 amino acid

<400> SEQUENCE: 23

Arg Ser Ser Gln Ser Leu Glu Tyr Ser Asp Gly Tyr Thr Tyr Leu Glu
1               5                   10                  15

<210> SEQ ID NO 24
<211> LENGTH: 7
<212> TYPE: PRT
<213> ORGANISM: Artificial
<220> FEATURE:
<223> OTHER INFORMATION: description of the artificial sequence: Lym2
      VL CDR2 amino acid

<400> SEQUENCE: 24

Gly Val Ser Asn Arg Phe Ser
1               5

<210> SEQ ID NO 25
<211> LENGTH: 9
<212> TYPE: PRT
<213> ORGANISM: Artificial
<220> FEATURE:
<223> OTHER INFORMATION: description of the artificial sequence: Lym2
      VL CDR3 amino acid

<400> SEQUENCE: 25

Phe Gln Ala Thr His Asp Pro Leu Thr
```

<210> SEQ ID NO 26
<211> LENGTH: 437
<212> TYPE: DNA
<213> ORGANISM: Artificial
<220> FEATURE:
<223> OTHER INFORMATION: description of the artificial sequence:
      synthetic DNA of chLym2 VH for vector

<400> SEQUENCE: 26

```
gacccctcac catgaatctg gggctgtcgc tgatcttcct ggcgctgatc ctgaagggcg      60
tgcagtgcga agtgcagctt gtcgaatccg gcggcgggct tgttcagccc gggcgctcga     120
tgaagctgtc gtgcgccgcg tccggcttca cgttctcgaa ctactacatg cgtgggtgc      180
gccaggcgcc gaagaagggg ctggagtggg tcgcgacgat ctcgtacgac ggctcgtcga     240
cgtactatcg cgattccgtg aagggggcgct tcacgatctc gcgcgacaac gcgaagtcga    300
cgctgtatct gcagatggat tcgctgcgct ccgaggatac cgcgacgtac tactgcgcgc     360
gccatcgcgg ctactactac tccggcgccg gctacttcga ctactggggg cagggcgtga    420
tggtgaccgt gtcgtcc                                                    437
```

<210> SEQ ID NO 27
<211> LENGTH: 404
<212> TYPE: DNA
<213> ORGANISM: Artificial
<220> FEATURE:
<223> OTHER INFORMATION: description of the artificial sequence:
      synthetic DNA of chLym2 VL for vector

<400> SEQUENCE: 27

```
gcctcttcac catgaagctg cccgttcgcc tgcttgtgct gatgttctgg atccccgcgt      60
cgtcgtccga cgtcgtgctg acgcagacgc ccgtgtcgct gtccgtgacg ctgggcgatc     120
aggcgtcgat ctcgtgtcgc tcgtcgcagt cgctggagta ctccgacggc tacacgtatc     180
tggagtggta tctgcagaag cccgggcagt cgccgcaggt gctgatctac ggcgtgtcga     240
atcgcttctc cggcgttccc gatcgcttca tcggctccgg ctccgggacc gacttcacgc     300
tgaagatctc gcgcgtcgaa cccgaggatc tgggcgtgta ctactgcttc caggcgacgc     360
acgatccgct gacgttcggc tccgggacga agctggagat caag                      404
```

<210> SEQ ID NO 28
<211> LENGTH: 36
<212> TYPE: DNA
<213> ORGANISM: Artificial
<220> FEATURE:
<223> OTHER INFORMATION: description of the artificial sequence: chLym2
      VH-A

<400> SEQUENCE: 28

```
atcacagatc gtcgacgacc cctcaccatg aatctg                                36
```

<210> SEQ ID NO 29
<211> LENGTH: 35
<212> TYPE: DNA
<213> ORGANISM: Artificial
<220> FEATURE:
<223> OTHER INFORMATION: description of the artificial sequence: chLym2
      VH-B

<400> SEQUENCE: 29

```
ggcccttggt gctagcggac gacacggtca ccatc                                 35
```

```
<210> SEQ ID NO 30
<211> LENGTH: 36
<212> TYPE: DNA
<213> ORGANISM: Artificial
<220> FEATURE:
<223> OTHER INFORMATION: description of the artificial sequence: chLym2
      VH-C

<400> SEQUENCE: 30
acgccatcac agatctgcct cttcaccatg aagctg                              36

<210> SEQ ID NO 31
<211> LENGTH: 35
<212> TYPE: DNA
<213> ORGANISM: Artificial
<220> FEATURE:
<223> OTHER INFORMATION: description of the artificial sequence: chLym2
      VH-D

<400> SEQUENCE: 31
gtgcagccac cgtacgcttg atctccagct tcgtc                               35

<210> SEQ ID NO 32
<211> LENGTH: 336
<212> TYPE: DNA
<213> ORGANISM: Artificial
<220> FEATURE:
<223> OTHER INFORMATION: description of the artificial sequence: LV0 DNA
<220> FEATURE:
<221> NAME/KEY: CDS
<222> LOCATION: (1)..(336)

<400> SEQUENCE: 32 gac atc gtg atg acg cag acg ccg ctg tcg ctg ccc gtt acg ccc ggc     48
Asp Ile Val Met Thr Gln Thr Pro Leu Ser Leu Pro Val Thr Pro Gly
1               5                   10                  15 gaa tcc gcg tcg atc tcg tgt cgc tcg tcg cag tcg ctg gag tac tcc     96
Glu Ser Ala Ser Ile Ser Cys Arg Ser Ser Gln Ser Leu Glu Tyr Ser
            20                  25                  30 gac ggc tac acg tat ctg gag tgg tat ctg cag aag ccc ggg cag tcg    144
Asp Gly Tyr Thr Tyr Leu Glu Trp Tyr Leu Gln Lys Pro Gly Gln Ser
        35                  40                  45 ccg cag gtg ctg atc tac ggc gtg tcg aat cgc ttc tcc ggc gtt ccc    192
Pro Gln Val Leu Ile Tyr Gly Val Ser Asn Arg Phe Ser Gly Val Pro
    50                  55                  60 gat cgc ttc tcc ggc tcc ggc tcc ggg acc gac ttc acg ctg aag atc    240
Asp Arg Phe Ser Gly Ser Gly Ser Gly Thr Asp Phe Thr Leu Lys Ile
65                  70                  75                  80 tcg cgc gtc gag gcc gag gac gtc ggc gtg tac tac tgc ttc cag gcg    288
Ser Arg Val Glu Ala Glu Asp Val Gly Val Tyr Tyr Cys Phe Gln Ala
                85                  90                  95 acg cac gat ccg ctg acg ttc ggg cag ggg acg aag ctg gag atc aag    336
Thr His Asp Pro Leu Thr Phe Gly Gln Gly Thr Lys Leu Glu Ile Lys
            100                 105                 110

<210> SEQ ID NO 33
<211> LENGTH: 112
<212> TYPE: PRT
<213> ORGANISM: Artificial
<220> FEATURE:
<223> OTHER INFORMATION: Synthetic Construct

<400> SEQUENCE: 33

Asp Ile Val Met Thr Gln Thr Pro Leu Ser Leu Pro Val Thr Pro Gly
```

```
                1               5                   10                  15
            Glu Ser Ala Ser Ile Ser Cys Arg Ser Ser Gln Ser Leu Glu Tyr Ser
                            20                  25                  30

Asp Gly Tyr Thr Tyr Leu Glu Trp Tyr Leu Gln Lys Pro Gly Gln Ser
                        35                  40                  45

Pro Gln Val Leu Ile Tyr Gly Val Ser Asn Arg Phe Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Phe Gln Ala
                            85                  90                  95

Thr His Asp Pro Leu Thr Phe Gly Gln Gly Thr Lys Leu Glu Ile Lys
                        100                 105                 110

<210> SEQ ID NO 34
<211> LENGTH: 336
<212> TYPE: DNA
<213> ORGANISM: Artificial
<220> FEATURE:
<223> OTHER INFORMATION: description of the artificial sequence: LV1 DNA
<220> FEATURE:
<221> NAME/KEY: CDS
<222> LOCATION: (1)..(336)

<400> SEQUENCE: 34 gac atc gtg atg acg cag acg ccg ctg tcg ctg ccc gtg acg ctg ggc        48
Asp Ile Val Met Thr Gln Thr Pro Leu Ser Leu Pro Val Thr Leu Gly
1               5                   10                  15 gag tcc gcg tcg atc tcg tgt cgc tcg tcg cag tcg ctg gag tac tcc        96
Glu Ser Ala Ser Ile Ser Cys Arg Ser Ser Gln Ser Leu Glu Tyr Ser
                20                  25                  30 gac ggc tac acg tat ctg gag tgg tat ctg cag aag ccc ggg cag tcg       144
Asp Gly Tyr Thr Tyr Leu Glu Trp Tyr Leu Gln Lys Pro Gly Gln Ser
            35                  40                  45 ccg cag gtg ctg atc tac ggc gtg tcg aat cgc ttc tcc ggc gtt ccc       192
Pro Gln Val Leu Ile Tyr Gly Val Ser Asn Arg Phe Ser Gly Val Pro
        50                  55                  60 gat cgc ttc tcc ggc tcc ggc tcc ggg acc gac ttc acg ctg aag atc       240
Asp Arg Phe Ser Gly Ser Gly Ser Gly Thr Asp Phe Thr Leu Lys Ile
65                  70                  75                  80 tcg cgc gtc gag gcc gag gac gtc ggc gtg tac tac tgc ttc cag gcg       288
Ser Arg Val Glu Ala Glu Asp Val Gly Val Tyr Tyr Cys Phe Gln Ala
                85                  90                  95 acg cac gat ccg ctg acg ttc ggg cag ggg acg aag ctg gag atc aag       336
Thr His Asp Pro Leu Thr Phe Gly Gln Gly Thr Lys Leu Glu Ile Lys
            100                 105                 110

<210> SEQ ID NO 35
<211> LENGTH: 112
<212> TYPE: PRT
<213> ORGANISM: Artificial
<220> FEATURE:
<223> OTHER INFORMATION: Synthetic Construct

<400> SEQUENCE: 35

Asp Ile Val Met Thr Gln Thr Pro Leu Ser Leu Pro Val Thr Leu Gly
1               5                   10                  15

Glu Ser Ala Ser Ile Ser Cys Arg Ser Ser Gln Ser Leu Glu Tyr Ser
                20                  25                  30

Asp Gly Tyr Thr Tyr Leu Glu Trp Tyr Leu Gln Lys Pro Gly Gln Ser
            35                  40                  45
```

```
Pro Gln Val Leu Ile Tyr Gly Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ala
                 85                  90                  95

Thr His Asp Pro Leu Thr Phe Gly Gln Gly Thr Lys Leu Glu Ile Lys
            100                 105                 110

<210> SEQ ID NO 36
<211> LENGTH: 336
<212> TYPE: DNA
<213> ORGANISM: Artificial
<220> FEATURE:
<223> OTHER INFORMATION: description of the artificial sequence: LV2a
      DNA
<220> FEATURE:
<221> NAME/KEY: CDS
<222> LOCATION: (1)..(336)

<400> SEQUENCE: 36 gac atc gtg ctg acg cag acg ccg ctg tcg ctg ccc gtg acg ctg ggc      48
Asp Ile Val Leu Thr Gln Thr Pro Leu Ser Leu Pro Val Thr Leu Gly
 1               5                  10                  15 gag tcc gcg tcg atc tcg tgt cgc tcg tcg cag tcg ctg gag tac tcc      96
Glu Ser Ala Ser Ile Ser Cys Arg Ser Ser Gln Ser Leu Glu Tyr Ser
             20                  25                  30 gac ggc tac acg tat ctg gag tgg tat ctg cag aag ccc ggg cag tcg     144
Asp Gly Tyr Thr Tyr Leu Glu Trp Tyr Leu Gln Lys Pro Gly Gln Ser
         35                  40                  45 ccg cag gtg ctg atc tac ggc gtg tcg aat cgc ttc tcc ggc gtt ccc     192
Pro Gln Val Leu Ile Tyr Gly Val Ser Asn Arg Phe Ser Gly Val Pro
     50                  55                  60 gat cgc ttc tcc ggc tcc ggc tcc ggg acc gac ttc acg ctg aag atc     240
Asp Arg Phe Ser Gly Ser Gly Ser Gly Thr Asp Phe Thr Leu Lys Ile
 65                  70                  75                  80 tcg cgc gtc gag gcc gag gac gtc ggc gtg tac tac tgc ttc cag gcg     288
Ser Arg Val Glu Ala Glu Asp Val Gly Val Tyr Tyr Cys Phe Gln Ala
                 85                  90                  95 acg cac gat ccg ctg acg ttc ggg cag ggg acg aag ctg gag atc aag     336
Thr His Asp Pro Leu Thr Phe Gly Gln Gly Thr Lys Leu Glu Ile Lys
            100                 105                 110

<210> SEQ ID NO 37
<211> LENGTH: 112
<212> TYPE: PRT
<213> ORGANISM: Artificial
<220> FEATURE:
<223> OTHER INFORMATION: Synthetic Construct

<400> SEQUENCE: 37

Asp Ile Val Leu Thr Gln Thr Pro Leu Ser Leu Pro Val Thr Leu Gly
 1               5                  10                  15

Glu Ser Ala Ser Ile Ser Cys Arg Ser Ser Gln Ser Leu Glu Tyr Ser
             20                  25                  30

Asp Gly Tyr Thr Tyr Leu Glu Trp Tyr Leu Gln Lys Pro Gly Gln Ser
         35                  40                  45

Pro Gln Val Leu Ile Tyr Gly Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110

<210> SEQ ID NO 38
<211> LENGTH: 336
<212> TYPE: DNA
<213> ORGANISM: Artificial
<220> FEATURE:
<223> OTHER INFORMATION: description of the artificial sequence: LV2b
      DNA
<220> FEATURE:
<221> NAME/KEY: CDS
<222> LOCATION: (1)..(336)

<400> SEQUENCE: 38 gac atc gtg atg acg cag acg ccg ctg tcg ctg ccc gtg acg ctg ggc      48
Asp Ile Val Met Thr Gln Thr Pro Leu Ser Leu Pro Val Thr Leu Gly
1               5                   10                  15 gag tcc gcg tcg atc tcg tgt cgc tcg tcg cag tcg ctg gag tac tcc      96
Glu Ser Ala Ser Ile Ser Cys Arg Ser Ser Gln Ser Leu Glu Tyr Ser
            20                  25                  30 gac ggc tac acg tat ctg gag tgg tat ctg cag aag ccc ggg cag tcg     144
Asp Gly Tyr Thr Tyr Leu Glu Trp Tyr Leu Gln Lys Pro Gly Gln Ser
        35                  40                  45 ccg cag gtg ctg atc tac ggc gtg tcg aat cgc ttc tcc ggc gtt ccc     192
Pro Gln Val Leu Ile Tyr Gly Val Ser Asn Arg Phe Ser Gly Val Pro
    50                  55                  60 gat cgc ttc tcc ggc tcc ggc tcc ggg acc gac ttc acg ctg aag atc     240
Asp Arg Phe Ser Gly Ser Gly Ser Gly Thr Asp Phe Thr Leu Lys Ile
65                  70                  75                  80 tcg cgc gtc gaa ccc gag gac gtc ggc gtg tac tac tgc ttc cag gcg     288
Ser Arg Val Glu Pro Glu Asp Val Gly Val Tyr Tyr Cys Phe Gln Ala
                85                  90                  95 acg cac gat ccg ctg acg ttc ggg cag ggg acg aag ctg gag atc aag     336
Thr His Asp Pro Leu Thr Phe Gly Gln Gly Thr Lys Leu Glu Ile Lys
            100                 105                 110

<210> SEQ ID NO 39
<211> LENGTH: 112
<212> TYPE: PRT
<213> ORGANISM: Artificial
<220> FEATURE:
<223> OTHER INFORMATION: Synthetic Construct

<400> SEQUENCE: 39

Asp Ile Val Met Thr Gln Thr Pro Leu Ser Leu Pro Val Thr Leu Gly
1               5                   10                  15

Glu Ser Ala Ser Ile Ser Cys Arg Ser Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Val Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110
```

<210> SEQ ID NO 40
<211> LENGTH: 336
<212> TYPE: DNA
<213> ORGANISM: Artificial
<220> FEATURE:
<223> OTHER INFORMATION: description of the artificial sequence: LV2c
      DNA
<220> FEATURE:
<221> NAME/KEY: CDS
<222> LOCATION: (1)..(336)

<400> SEQUENCE: 40

```
gac gtc gtg ctg acg cag acg ccg ctg tcg ctg ccc gtt acg ccc ggc      48
Asp Val Val Leu Thr Gln Thr Pro Leu Ser Leu Pro Val Thr Pro Gly
1               5                   10                  15 gaa tcc gcg tcg atc tcg tgt cgc tcg tcg cag tcg ctg gag tac tcc      96
Glu Ser Ala Ser Ile Ser Cys Arg Ser Ser Gln Ser Leu Glu Tyr Ser
            20                  25                  30 gac ggc tac acg tat ctg gag tgg tat ctg cag aag ccc ggg cag tcg     144
Asp Gly Tyr Thr Tyr Leu Glu Trp Tyr Leu Gln Lys Pro Gly Gln Ser
        35                  40                  45 ccg cag gtg ctg atc tac ggc gtg tcg aat cgc ttc tcc ggc gtt ccc     192
Pro Gln Val Leu Ile Tyr Gly Val Ser Asn Arg Phe Ser Gly Val Pro
    50                  55                  60 gat cgc ttc tcc ggc tcc ggc tcc ggg acc gac ttc acg ctg aag atc     240
Asp Arg Phe Ser Gly Ser Gly Ser Gly Thr Asp Phe Thr Leu Lys Ile
65                  70                  75                  80 tcg cgc gtc gag gcc gag gac gtc ggc gtg tac tac tgc ttc cag gcg     288
Ser Arg Val Glu Ala Glu Asp Val Gly Val Tyr Tyr Cys Phe Gln Ala
                85                  90                  95 acg cac gat ccg ctg acg ttc ggg cag ggg acg aag ctg gag atc aag     336
Thr His Asp Pro Leu Thr Phe Gly Gln Gly Thr Lys Leu Glu Ile Lys
            100                 105                 110
```

<210> SEQ ID NO 41
<211> LENGTH: 112
<212> TYPE: PRT
<213> ORGANISM: Artificial
<220> FEATURE:
<223> OTHER INFORMATION: Synthetic Construct

<400> SEQUENCE: 41

```
Asp Val Val Leu Thr Gln Thr Pro Leu Ser Leu Pro Val Thr Pro Gly
1               5                   10                  15

Glu Ser Ala Ser Ile Ser Cys Arg Ser Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Val Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110
```

<210> SEQ ID NO 42
<211> LENGTH: 336
<212> TYPE: DNA
<213> ORGANISM: Artificial

<220> FEATURE:
<223> OTHER INFORMATION: description of the artificial sequence: LV3a
      DNA
<220> FEATURE:
<221> NAME/KEY: CDS
<222> LOCATION: (1)..(336)

<400> SEQUENCE: 42

```
gac gtc gtg ctg acg cag acg ccg ctg tcg ctg ccc gtt acg ccc ggc      48
Asp Val Val Leu Thr Gln Thr Pro Leu Ser Leu Pro Val Thr Pro Gly
1               5                   10                  15 gaa tcc gcg tcg atc tcg tgt cgc tcg tcg cag tcg ctg gag tac tcc      96
Glu Ser Ala Ser Ile Ser Cys Arg Ser Ser Gln Ser Leu Glu Tyr Ser
            20                  25                  30 gac ggc tac acg tat ctg gag tgg tat ctg cag aag ccc ggg cag tcg     144
Asp Gly Tyr Thr Tyr Leu Glu Trp Tyr Leu Gln Lys Pro Gly Gln Ser
        35                  40                  45 ccg cag gtg ctg atc tac ggc gtg tcg aat cgc ttc tcc ggc gtt ccc     192
Pro Gln Val Leu Ile Tyr Gly Val Ser Asn Arg Phe Ser Gly Val Pro
    50                  55                  60 gat cgc ttc tcc ggc tcc ggc tcc ggg acc gac ttc acg ctg aag atc     240
Asp Arg Phe Ser Gly Ser Gly Ser Gly Thr Asp Phe Thr Leu Lys Ile
65                  70                  75                  80 tcg cgc gtc gaa ccc gag gac gtc ggc gtg tac tac tgc ttc cag gcg     288
Ser Arg Val Glu Pro Glu Asp Val Gly Val Tyr Tyr Cys Phe Gln Ala
                85                  90                  95 acg cac gat ccg ctg acg ttc ggg cag ggg acg aag ctg gag atc aag     336
Thr His Asp Pro Leu Thr Phe Gly Gln Gly Thr Lys Leu Glu Ile Lys
            100                 105                 110
```

<210> SEQ ID NO 43
<211> LENGTH: 112
<212> TYPE: PRT
<213> ORGANISM: Artificial
<220> FEATURE:
<223> OTHER INFORMATION: Synthetic Construct

<400> SEQUENCE: 43

```
Asp Val Val Leu Thr Gln Thr Pro Leu Ser Leu Pro Val Thr Pro Gly
1               5                   10                  15

Glu Ser Ala Ser Ile Ser Cys Arg Ser Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Val Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110
```

<210> SEQ ID NO 44
<211> LENGTH: 336
<212> TYPE: DNA
<213> ORGANISM: Artificial
<220> FEATURE:
<223> OTHER INFORMATION: LV3b DNA
<220> FEATURE:
<221> NAME/KEY: CDS
<222> LOCATION: (1)..(336)

<400> SEQUENCE: 44

```
gac gtc gtg ctg acg cag acg ccg ctg tcg ctg ccc gtg acg ctg ggc        48
Asp Val Val Leu Thr Gln Thr Pro Leu Ser Leu Pro Val Thr Leu Gly
1               5                   10                  15 gag tcc gcg tcg atc tcg tgt cgc tcg tcg cag tcg ctg gag tac tcc        96
Glu Ser Ala Ser Ile Ser Cys Arg Ser Ser Gln Ser Leu Glu Tyr Ser
            20                  25                  30 gac ggc tac acg tat ctg gag tgg tat ctg cag aag ccc ggg cag tcg       144
Asp Gly Tyr Thr Tyr Leu Glu Trp Tyr Leu Gln Lys Pro Gly Gln Ser
        35                  40                  45 ccg cag gtg ctg atc tac ggc gtg tcg aat cgc ttc tcc ggc gtt ccc       192
Pro Gln Val Leu Ile Tyr Gly Val Ser Asn Arg Phe Ser Gly Val Pro
    50                  55                  60 gat cgc ttc tcc ggc tcc ggc tcc ggg acc gac ttc acg ctg aag atc       240
Asp Arg Phe Ser Gly Ser Gly Ser Gly Thr Asp Phe Thr Leu Lys Ile
65                  70                  75                  80 tcg cgc gtc gag gcc gag gac gtc ggc gtg tac tac tgc ttc cag gcg       288
Ser Arg Val Glu Ala Glu Asp Val Gly Val Tyr Tyr Cys Phe Gln Ala
                85                  90                  95 acg cac gat ccg ctg acg ttc ggg cag ggg acg aag ctg gag atc aag       336
Thr His Asp Pro Leu Thr Phe Gly Gln Gly Thr Lys Leu Glu Ile Lys
            100                 105                 110
```

<210> SEQ ID NO 45
<211> LENGTH: 112
<212> TYPE: PRT
<213> ORGANISM: Artificial
<220> FEATURE:
<223> OTHER INFORMATION: Synthetic Construct

<400> SEQUENCE: 45

```
Asp Val Val Leu Thr Gln Thr Pro Leu Ser Leu Pro Val Thr Leu Gly
1               5                   10                  15

Glu Ser Ala Ser Ile Ser Cys Arg Ser Ser Gln Ser Leu Glu Tyr Ser
            20                  25                  30

Asp Gly Tyr Thr Tyr Leu Glu Trp Tyr Leu Gln Lys Pro Gly Gln Ser
        35                  40                  45

Pro Gln Val Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110
```

<210> SEQ ID NO 46
<211> LENGTH: 336
<212> TYPE: DNA
<213> ORGANISM: Artificial
<220> FEATURE:
<223> OTHER INFORMATION: description of the artificial sequence: LV4 DNA
<220> FEATURE:
<221> NAME/KEY: CDS
<222> LOCATION: (1)..(336)

<400> SEQUENCE: 46

```
gac gtc gtg ctg acg cag acg ccg ctg tcg ctg ccc gtg acg ctg ggc        48
Asp Val Val Leu Thr Gln Thr Pro Leu Ser Leu Pro Val Thr Leu Gly
1               5                   10                  15 gag tcc gcg tcg atc tcg tgt cgc tcg tcg cag tcg ctg gag tac tcc        96
Glu Ser Ala Ser Ile Ser Cys Arg Ser Ser Gln Ser Leu Glu Tyr Ser
```

```
                Glu Ser Ala Ser Ile Ser Cys Arg Ser Ser Gln Ser Leu Glu Tyr Ser
                                 20                  25                  30 gac ggc tac acg tat ctg gag tgg tat ctg cag aag ccc ggg cag tcg        144
Asp Gly Tyr Thr Tyr Leu Glu Trp Tyr Leu Gln Lys Pro Gly Gln Ser
             35                  40                  45 ccg cag gtg ctg atc tac ggc gtg tcg aat cgc ttc tcc ggc gtt ccc        192
Pro Gln Val Leu Ile Tyr Gly Val Ser Asn Arg Phe Ser Gly Val Pro
 50                  55                  60 gat cgc ttc tcc ggc tcc ggc tcc ggg acc gac ttc acg ctg aag atc        240
Asp Arg Phe Ser Gly Ser Gly Ser Gly Thr Asp Phe Thr Leu Lys Ile
 65                  70                  75                  80 tcg cgc gtc gaa ccc gag gac gtc ggc gtg tac tac tgc ttc cag gcg        288
Ser Arg Val Glu Pro Glu Asp Val Gly Val Tyr Tyr Cys Phe Gln Ala
                 85                  90                  95 acg cac gat ccg ctg acg ttc ggg cag ggg acg aag ctg gag atc aag        336
Thr His Asp Pro Leu Thr Phe Gly Gln Gly Thr Lys Leu Glu Ile Lys
                100                 105                 110

<210> SEQ ID NO 47
<211> LENGTH: 112
<212> TYPE: PRT
<213> ORGANISM: Artificial
<220> FEATURE:
<223> OTHER INFORMATION: Synthetic Construct

<400> SEQUENCE: 47

Asp Val Val Leu Thr Gln Thr Pro Leu Ser Leu Pro Val Thr Leu Gly
 1               5                  10                  15

Glu Ser Ala Ser Ile Ser Cys Arg Ser Ser Gln Ser Leu Glu Tyr Ser
                 20                  25                  30

Asp Gly Tyr Thr Tyr Leu Glu Trp Tyr Leu Gln Lys Pro Gly Gln Ser
             35                  40                  45

Pro Gln Val Leu Ile Tyr Gly Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Pro Glu Asp Val Gly Val Tyr Tyr Cys Phe Gln Ala
                 85                  90                  95

Thr His Asp Pro Leu Thr Phe Gly Gln Gly Thr Lys Leu Glu Ile Lys
                100                 105                 110

<210> SEQ ID NO 48
<211> LENGTH: 369
<212> TYPE: DNA
<213> ORGANISM: Artificial
<220> FEATURE:
<223> OTHER INFORMATION: description of the artificial sequence: HV0 DNA
<220> FEATURE:
<221> NAME/KEY: CDS
<222> LOCATION: (1)..(369)

<400> SEQUENCE: 48 gaa gtg cag ctt gtc gaa tcc ggc ggc ggc gtc gtt cag ccc ggg cgc         48
Glu Val Gln Leu Val Glu Ser Gly Gly Gly Val Val Gln Pro Gly Arg
 1               5                  10                  15 tcg ctg cgc ctg tcg tgc gcc gcg tcc ggc ttc acg ttc tcg aac tac         96
Ser Leu Arg Leu Ser Cys Ala Ala Ser Gly Phe Thr Phe Ser Asn Tyr
                 20                  25                  30 tac atg gcg tgg gtg cgc cag gcg ccc ggg aag ggg ctg gag tgg gtc        144
Tyr Met Ala Trp Val Arg Gln Ala Pro Gly Lys Gly Leu Glu Trp Val
             35                  40                  45
```

```
gcg acg atc tcg tac gac ggc tcg tcg acg tac tat cgc gat tcc gtg      192
Ala Thr Ile Ser Tyr Asp Gly Ser Ser Thr Tyr Tyr Arg Asp Ser Val
 50                  55                  60 aag ggg cgc ttc acg atc tcg cgc gac aac gcg aag aac tcg ctg tat      240
Lys Gly Arg Phe Thr Ile Ser Arg Asp Asn Ala Lys Asn Ser Leu Tyr
 65                  70                  75                  80 ctg cag atg aac tcg ctg cgc gcc gag gat acc gcc gtg tac tac tgc      288
Leu Gln Met Asn Ser Leu Arg Ala Glu Asp Thr Ala Val Tyr Tyr Cys
                 85                  90                  95 gcg cgc cat cgc ggc tac tac tac tcc ggc gcc ggc tac ttc gac tac      336
Ala Arg His Arg Gly Tyr Tyr Tyr Ser Gly Ala Gly Tyr Phe Asp Tyr
            100                 105                 110 tgg ggg cag ggg acg atg gtg acc gtg tcg tcc                          369
Trp Gly Gln Gly Thr Met Val Thr Val Ser Ser
        115                 120
```

<210> SEQ ID NO 49
<211> LENGTH: 123
<212> TYPE: PRT
<213> ORGANISM: Artificial
<220> FEATURE:
<223> OTHER INFORMATION: Synthetic Construct

<400> SEQUENCE: 49

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ala Thr Ile Ser Tyr Asp Gly Ser Ser Thr Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Arg Gly Tyr Tyr Tyr Ser Gly Ala Gly Tyr Phe Asp Tyr
            100                 105                 110

Trp Gly Gln Gly Thr Met Val Thr Val Ser Ser
        115                 120
```

<210> SEQ ID NO 50
<211> LENGTH: 369
<212> TYPE: DNA
<213> ORGANISM: Artificial
<220> FEATURE:
<223> OTHER INFORMATION: description of the artificial sequence: HV1 DNA
<220> FEATURE:
<221> NAME/KEY: CDS
<222> LOCATION: (1)..(369)

<400> SEQUENCE: 50

```
gaa gtg cag ctt gtc gaa tcc ggc ggc ggc gtc gtg cag ccc ggg cgc       48
Glu Val Gln Leu Val Glu Ser Gly Gly Gly Val Val Gln Pro Gly Arg
 1               5                  10                  15 tcg ctg cgc ctg tcg tgc gcc gcg tcc ggc ttc acg ttc tcg aac tac       96
Ser Leu Arg Leu Ser Cys Ala Ala Ser Gly Phe Thr Phe Ser Asn Tyr
            20                  25                  30 tac atg gcg tgg gtg cgc cag gcg ccc ggg aag ggg ctg gag tgg gtc      144
Tyr Met Ala Trp Val Arg Gln Ala Pro Gly Lys Gly Leu Glu Trp Val
        35                  40                  45
```

```
gcg acg atc tcg tac gac ggc tcg tcg acg tac tat cgc gat tcc gtg        192
Ala Thr Ile Ser Tyr Asp Gly Ser Ser Thr Tyr Tyr Arg Asp Ser Val
 50                  55                  60 aag ggg cgc ttc acg atc tcg cgc gac aac gcg aag aac tcg ctg tat        240
Lys Gly Arg Phe Thr Ile Ser Arg Asp Asn Ala Lys Asn Ser Leu Tyr
 65                  70                  75                  80 ctg cag atg aac tcg ctg cgc gcc gag gat acc gcg acg tac tac tgc        288
Leu Gln Met Asn Ser Leu Arg Ala Glu Asp Thr Ala Thr Tyr Tyr Cys
                 85                  90                  95 gcg cgc cat cgc ggc tac tac tac tcc ggc gcc ggc tac ttc gac tac        336
Ala Arg His Arg Gly Tyr Tyr Tyr Ser Gly Ala Gly Tyr Phe Asp Tyr
             100                 105                 110 tgg ggg cag ggg acg atg gtg acc gtg tcg tcc                            369
Trp Gly Gln Gly Thr Met Val Thr Val Ser Ser
        115                 120
```

<210> SEQ ID NO 51
<211> LENGTH: 123
<212> TYPE: PRT
<213> ORGANISM: Artificial
<220> FEATURE:
<223> OTHER INFORMATION: Synthetic Construct

<400> SEQUENCE: 51

```
Glu Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Asn Tyr
             20                  25                  30

Tyr Met Ala Trp Val Arg Gln Ala Pro Gly Lys Gly Leu Glu Trp Val
         35                  40                  45

Ala Thr Ile Ser Tyr Asp Gly Ser Ser Thr Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Thr Tyr Tyr Cys
                 85                  90                  95

Ala Arg His Arg Gly Tyr Tyr Tyr Ser Gly Ala Gly Tyr Phe Asp Tyr
             100                 105                 110

Trp Gly Gln Gly Thr Met Val Thr Val Ser Ser
        115                 120
```

<210> SEQ ID NO 52
<211> LENGTH: 369
<212> TYPE: DNA
<213> ORGANISM: Artificial
<220> FEATURE:
<223> OTHER INFORMATION: description of the artificial sequence: HV2a
      DNA
<220> FEATURE:
<221> NAME/KEY: CDS
<222> LOCATION: (1)..(369)

<400> SEQUENCE: 52

```
gaa gtg cag ctt gtc gaa tcc ggc ggc ggc gtc gtg cag ccc ggg cgc         48
Glu Val Gln Leu Val Glu Ser Gly Gly Gly Val Val Gln Pro Gly Arg
 1               5                   10                  15 tcg ctg cgc ctg tcg tgc gcc gcg tcc ggc ttc acg ttc tcg aac tac         96
Ser Leu Arg Leu Ser Cys Ala Ala Ser Gly Phe Thr Phe Ser Asn Tyr
             20                  25                  30 tac atg gcg tgg gtg cgc cag gcg ccc ggg aag ggg ctg gag tgg gtc        144
Tyr Met Ala Trp Val Arg Gln Ala Pro Gly Lys Gly Leu Glu Trp Val
         35                  40                  45
```

```
gcg acg atc tcg tac gac ggc tcg tcg acg tac tat cgc gat tcc gtg       192
Ala Thr Ile Ser Tyr Asp Gly Ser Ser Thr Tyr Tyr Arg Asp Ser Val
 50                  55                  60 aag ggg cgc ttc acg atc tcg cgc gac aac gcg aag aac tcg ctg tat       240
Lys Gly Arg Phe Thr Ile Ser Arg Asp Asn Ala Lys Asn Ser Leu Tyr
 65                  70                  75                  80 ctg cag atg aac tcg ctg cgc gcc gag gat acc gcg acg tac tac tgc       288
Leu Gln Met Asn Ser Leu Arg Ala Glu Asp Thr Ala Thr Tyr Tyr Cys
                 85                  90                  95 gcg cgc cat cgc ggc tac tac tac tcc ggc gcc ggc tac ttc gac tac       336
Ala Arg His Arg Gly Tyr Tyr Tyr Ser Gly Ala Gly Tyr Phe Asp Tyr
             100                 105                 110 tgg ggg cag ggc gtg atg gtg acc gtg tcg tcc                           369
Trp Gly Gln Gly Val Met Val Thr Val Ser Ser
        115                 120

<210> SEQ ID NO 53
<211> LENGTH: 123
<212> TYPE: PRT
<213> ORGANISM: Artificial
<220> FEATURE:
<223> OTHER INFORMATION: Synthetic Construct

<400> SEQUENCE: 53

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
             20                  25                  30

Tyr Met Ala Trp Val Arg Gln Ala Pro Gly Lys Gly Leu Glu Trp Val
         35                  40                  45

Ala Thr Ile Ser Tyr Asp Gly Ser Ser Thr Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Thr Tyr Tyr Cys
                 85                  90                  95

Ala Arg His Arg Gly Tyr Tyr Tyr Ser Gly Ala Gly Tyr Phe Asp Tyr
             100                 105                 110

Trp Gly Gln Gly Val Met Val Thr Val Ser Ser
        115                 120

<210> SEQ ID NO 54
<211> LENGTH: 369
<212> TYPE: DNA
<213> ORGANISM: Artificial
<220> FEATURE:
<223> OTHER INFORMATION: description of the artificial sequence: HV2b
      DNA
<220> FEATURE:
<221> NAME/KEY: CDS
<222> LOCATION: (1)..(369)

<400> SEQUENCE: 54 gaa gtg cag ctt gtc gaa tcc ggc ggc ggc gtc gtt cag ccc ggg cgc        48
Glu Val Gln Leu Val Glu Ser Gly Gly Gly Val Val Gln Pro Gly Arg
 1               5                  10                  15 tcg atg cgc ctg tcg tgc gcc gcg tcc ggc ttc acg ttc tcg aac tac        96
Ser Met Arg Leu Ser Cys Ala Ala Ser Gly Phe Thr Phe Ser Asn Tyr
             20                  25                  30 tac atg gcg tgg gtg cgc cag gcg ccc ggg aag ggg ctg gag tgg gtc       144
Tyr Met Ala Trp Val Arg Gln Ala Pro Gly Lys Gly Leu Glu Trp Val
```

```
                         35                  40                  45
gcg acg atc tcg tac gac ggc tcg tcg acg tac tat cgc gat tcc gtg      192
Ala Thr Ile Ser Tyr Asp Gly Ser Ser Thr Tyr Tyr Arg Asp Ser Val
 50                  55                  60 aag ggg cgc ttc acg atc tcg cgc gac aac gcg aag aac tcg ctg tat      240
Lys Gly Arg Phe Thr Ile Ser Arg Asp Asn Ala Lys Asn Ser Leu Tyr
 65                  70                  75                  80 ctg cag atg aac tcg ctg cgc gcc gag gat acc gcc gtg tac tac tgc      288
Leu Gln Met Asn Ser Leu Arg Ala Glu Asp Thr Ala Val Tyr Tyr Cys
                 85                  90                  95 gcg cgc cat cgc ggc tac tac tac tcc ggc gcc ggc tac ttc gac tac      336
Ala Arg His Arg Gly Tyr Tyr Tyr Ser Gly Ala Gly Tyr Phe Asp Tyr
            100                 105                 110 tgg ggg cag ggc gtg atg gtg acc gtg tcg tcc                          369
Trp Gly Gln Gly Val Met Val Thr Val Ser Ser
        115                 120
```

<210> SEQ ID NO 55
<211> LENGTH: 123
<212> TYPE: PRT
<213> ORGANISM: Artificial
<220> FEATURE:
<223> OTHER INFORMATION: Synthetic Construct

<400> SEQUENCE: 55

```
Glu Val Gln Leu Val Glu Ser Gly Gly Gly Val Val Gln Pro Gly Arg
 1               5                   10                  15

Ser Met Arg Leu Ser Cys Ala Ala Ser Gly Phe Thr Phe Ser Asn Tyr
             20                  25                  30

Tyr Met Ala Trp Val Arg Gln Ala Pro Gly Lys Gly Leu Glu Trp Val
         35                  40                  45

Ala Thr Ile Ser Tyr Asp Gly Ser Ser Thr Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Arg Gly Tyr Tyr Tyr Ser Gly Ala Gly Tyr Phe Asp Tyr
            100                 105                 110

Trp Gly Gln Gly Val Met Val Thr Val Ser Ser
        115                 120
```

<210> SEQ ID NO 56
<211> LENGTH: 369
<212> TYPE: DNA
<213> ORGANISM: Artificial
<220> FEATURE:
<223> OTHER INFORMATION: description of the artificial sequence: HV3 DNA
<220> FEATURE:
<221> NAME/KEY: CDS
<222> LOCATION: (1)..(369)

<400> SEQUENCE: 56

```
gaa gtg cag ctt gtc gaa tcc ggc ggc ggc gtc gtt cag ccc ggg cgc       48
Glu Val Gln Leu Val Glu Ser Gly Gly Gly Val Val Gln Pro Gly Arg
 1               5                   10                  15 tcg atg cgc ctg tcg tgc gcc gcg tcc ggc ttc acg ttc tcg aac tac       96
Ser Met Arg Leu Ser Cys Ala Ala Ser Gly Phe Thr Phe Ser Asn Tyr
             20                  25                  30 tac atg gcg tgg gtg cgc cag gcg ccc ggg aag ggg ctg gag tgg gtc      144
Tyr Met Ala Trp Val Arg Gln Ala Pro Gly Lys Gly Leu Glu Trp Val
```

```
gcg acg atc tcg tac gac ggc tcg tcg acg tac tat cgc gat tcc gtg       192
Ala Thr Ile Ser Tyr Asp Gly Ser Ser Thr Tyr Tyr Arg Asp Ser Val
        50                  55                  60 aag ggg cgc ttc acg atc tcg cgc gac aac gcg aag aac tcg ctg tat       240
Lys Gly Arg Phe Thr Ile Ser Arg Asp Asn Ala Lys Asn Ser Leu Tyr
65                  70                  75                  80 ctg cag atg aac tcg ctg cgc gcc gag gat acc gcg acg tac tac tgc       288
Leu Gln Met Asn Ser Leu Arg Ala Glu Asp Thr Ala Thr Tyr Tyr Cys
                85                  90                  95 gcg cgc cat cgc ggc tac tac tac tcc ggc gcc ggc tac ttc gac tac       336
Ala Arg His Arg Gly Tyr Tyr Tyr Ser Gly Ala Gly Tyr Phe Asp Tyr
            100                 105                 110 tgg ggg cag ggc gtg atg gtg acc gtg tcg tcc                           369
Trp Gly Gln Gly Val Met Val Thr Val Ser Ser
            115                 120
```

<210> SEQ ID NO 57
<211> LENGTH: 123
<212> TYPE: PRT
<213> ORGANISM: Artificial
<220> FEATURE:
<223> OTHER INFORMATION: Synthetic Construct

<400> SEQUENCE: 57

```
Glu Val Gln Leu Val Glu Ser Gly Gly Gly Val Val Gln Pro Gly Arg
1               5                   10                  15

Ser Met Arg Leu Ser Cys Ala Ala Ser Gly Phe Thr Phe Ser Asn Tyr
            20                  25                  30

Tyr Met Ala Trp Val Arg Gln Ala Pro Gly Lys Gly Leu Glu Trp Val
        35                  40                  45

Ala Thr Ile Ser Tyr Asp Gly Ser Ser Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Ala Arg His Arg Gly Tyr Tyr Tyr Ser Gly Ala Gly Tyr Phe Asp Tyr
            100                 105                 110

Trp Gly Gln Gly Val Met Val Thr Val Ser Ser
            115                 120
```

<210> SEQ ID NO 58
<211> LENGTH: 369
<212> TYPE: DNA
<213> ORGANISM: Artificial
<220> FEATURE:
<223> OTHER INFORMATION: description of the artificial sequence: HV4 DNA
<220> FEATURE:
<221> NAME/KEY: CDS
<222> LOCATION: (1)..(369)

<400> SEQUENCE: 58

```
gaa gtg cag ctt gtc gaa tcc ggc ggc ggc gtc gtt cag ccc ggg cgc       48
Glu Val Gln Leu Val Glu Ser Gly Gly Gly Val Val Gln Pro Gly Arg
1               5                   10                  15 tcg atg cgc ctg tcg tgc gcc gcg tcc ggc ttc acg ttc tcg aac tac       96
Ser Met Arg Leu Ser Cys Ala Ala Ser Gly Phe Thr Phe Ser Asn Tyr
            20                  25                  30 tac atg gcg tgg gtg cgc cag gcg ccc ggg aag ggg ctg gag tgg gtc      144
Tyr Met Ala Trp Val Arg Gln Ala Pro Gly Lys Gly Leu Glu Trp Val
```

```
            35                  40                  45
gcg acg atc tcg tac gac ggc tcg tcg acg tac tat cgc gat tcc gtg        192
Ala Thr Ile Ser Tyr Asp Gly Ser Ser Thr Tyr Tyr Arg Asp Ser Val
         50                  55                  60 aag ggg cgc ttc acg atc tcg cgc gac aac gcg aag tcg tcg ctg tat        240
Lys Gly Arg Phe Thr Ile Ser Arg Asp Asn Ala Lys Ser Ser Leu Tyr
 65                  70                  75                  80 ctg cag atg aac tcg ctg cgc gcc gag gat acc gcg acg tac tac tgc        288
Leu Gln Met Asn Ser Leu Arg Ala Glu Asp Thr Ala Thr Tyr Tyr Cys
                 85                  90                  95 gcg cgc cat cgc ggc tac tac tac tcc ggc gcc ggc tac ttc gac tac        336
Ala Arg His Arg Gly Tyr Tyr Tyr Ser Gly Ala Gly Tyr Phe Asp Tyr
            100                 105                 110 tgg ggg cag ggc gtg atg gtg acc gtg tcg tcc                            369
Trp Gly Gln Gly Val Met Val Thr Val Ser Ser
            115                 120

<210> SEQ ID NO 59
<211> LENGTH: 123
<212> TYPE: PRT
<213> ORGANISM: Artificial
<220> FEATURE:
<223> OTHER INFORMATION: Synthetic Construct

<400> SEQUENCE: 59

Glu Val Gln Leu Val Glu Ser Gly Gly Gly Val Val Gln Pro Gly Arg
 1               5                  10                  15

Ser Met Arg Leu Ser Cys Ala Ala Ser Gly Phe Thr Phe Ser Asn Tyr
             20                  25                  30

Tyr Met Ala Trp Val Arg Gln Ala Pro Gly Lys Gly Leu Glu Trp Val
         35                  40                  45

Ala Thr Ile Ser Tyr Asp Gly Ser Ser Thr Tyr Tyr Arg Asp Ser Val
     50                  55                  60

Lys Gly Arg Phe Thr Ile Ser Arg Asp Asn Ala Lys Ser Ser Leu Tyr
 65                  70                  75                  80

Leu Gln Met Asn Ser Leu Arg Ala Glu Asp Thr Ala Thr Tyr Tyr Cys
                 85                  90                  95

Ala Arg His Arg Gly Tyr Tyr Tyr Ser Gly Ala Gly Tyr Phe Asp Tyr
            100                 105                 110

Trp Gly Gln Gly Val Met Val Thr Val Ser Ser
            115                 120

<210> SEQ ID NO 60
<211> LENGTH: 39
<212> TYPE: DNA
<213> ORGANISM: Artificial
<220> FEATURE:
<223> OTHER INFORMATION: description of the artificial sequence: human
      CRTH2 azami-A

<400> SEQUENCE: 60
catggatccg ccaccatgtc ggccaacgcc acactgaag                              39

<210> SEQ ID NO 61
<211> LENGTH: 28
<212> TYPE: DNA
<213> ORGANISM: Artificial
<220> FEATURE:
<223> OTHER INFORMATION: description of the artificial sequence: human
      CRTH2 azami-B

<400> SEQUENCE: 61
```

```
cataagctta ctcgaggtgc tgctcagc                                        28
```

<210> SEQ ID NO 62
<211> LENGTH: 1191
<212> TYPE: DNA
<213> ORGANISM: Macaca fascicularis

<400> SEQUENCE: 62

```
atgtccgcca acgccacgct gaagccgctc tgccccatcc tagaggagat gagccatctc     60
cggagccaca gcaacaccag catccgctac atcgaccacg cgaccgtgct gctgcacggg    120
ctggcctcgc tgctgggcct ggtggagaac ggagtcatcc tcttcgtggt gggctgccgc    180
atgcgccaga ccgtggtcac cacctgggtg ctacacctgg cactgtctga cctgttggcc    240
tctgcttccc tgcccttctt cacctacttc ttggccgtgg ccactcgtg ggagctgggc     300
accaccttct gcaaactgca ttcctccatc ttctttctca acatgtttgc cagcggcttc    360
ctgctcagcg ccatcagcct ggaccgctgc ctgcaggtgg tgtggccggt gtgggcgcag    420
aaccaccgca ccgtggccgc agcgcacaaa gtctgcctgg tgctctgggc actagcagtg    480
ctcaacacgg tgccctattt cgtgttccgg gacaccatct cacggctgga tgggcgcatc    540
atgtgctact acaacgtgct gctcctgaac ccggggcctg accgtgacgc cacgtgcaac    600
tcgcgccagg cggccctggc agtcagcaag ttcctgctgg ccttcctggt gccgctggcg    660
atcatcgcct cgagccatgc ggccgtgagc ctgcgactgc agcaccgcgg acgccggcgg    720
cccggccgct ttgtgcgcct ggtggcggcc gtcgtggcgg ccttcgcact ctgctgggg    780
ccctaccacg tgttcagcct gctggaggcg cgggcgcacg ccaaccccgg gttgcggccg    840
cttgtgtggc gcgggctgcc cttcgtcacc agcctggcct tcttcaacag cgtggccaac    900
ccggtgctct acgtgctcac ctgccccgac atgctgcgca gctgcggcg ctcgctgcgc    960
acggtgctgg agagcgtgct ggtggacgac agcgagctgg gtggcgcggg aagcagccgc   1020
cgccgccgcc gcacccctc cacggcccgc tcggcctcct ccttagctct cagcagccgc   1080
cccgaggaac ggcggggccc cgcgcgcctc ttcggctggc tgctgggcgg ctgcgcagcg   1140
tccccgcaga ggggccccct gaaccgggcg ctgagcagca cctcgagtta g            1191
```

<210> SEQ ID NO 63
<211> LENGTH: 396
<212> TYPE: PRT
<213> ORGANISM: Macaca fascicularis

<400> SEQUENCE: 63

```
Met Ser Ala Asn Ala Thr Leu Lys Pro Leu Cys Pro Ile Leu Glu Glu
1               5                   10                  15

Met Ser His Leu Arg Ser His Ser Asn Thr Ser Ile Arg Tyr Ile Asp
                20                  25                  30

His Ala Thr Val Leu Leu His Gly Leu Ala Ser Leu Leu Gly Leu Val
            35                  40                  45

Glu Asn Gly Val Ile Leu Phe Val Val Gly Cys Arg Met Arg Gln Thr
        50                  55                  60

Val Val Thr Thr Trp Val Leu His Leu Ala Leu Ser Asp Leu Leu Ala
65                  70                  75                  80

Ser Ala Ser Leu Pro Phe Phe Thr Tyr Phe Leu Ala Val Gly His Ser
                85                  90                  95

Trp Glu Leu Gly Thr Thr Phe Cys Lys Leu His Ser Ser Ile Phe Phe
                100                 105                 110
```

```
Leu Asn Met Phe Ala Ser Gly Phe Leu Leu Ser Ala Ile Ser Leu Asp
        115                 120                 125

Arg Cys Leu Gln Val Val Trp Pro Val Trp Ala Gln Asn His Arg Thr
130                 135                 140

Val Ala Ala His Lys Val Cys Leu Val Leu Trp Ala Leu Ala Val
145                 150                 155                 160

Leu Asn Thr Val Pro Tyr Phe Val Phe Arg Asp Thr Ile Ser Arg Leu
                165                 170                 175

Asp Gly Arg Ile Met Cys Tyr Tyr Asn Val Leu Leu Leu Asn Pro Gly
            180                 185                 190

Pro Asp Arg Asp Ala Thr Cys Asn Ser Arg Gln Ala Ala Leu Ala Val
            195                 200                 205

Ser Lys Phe Leu Leu Ala Phe Leu Val Pro Leu Ala Ile Ile Ala Ser
        210                 215                 220

Ser His Ala Ala Val Ser Leu Arg Leu Gln His Arg Gly Arg Arg Arg
225                 230                 235                 240

Pro Gly Arg Phe Val Arg Leu Val Ala Ala Val Val Ala Ala Phe Ala
                245                 250                 255

Leu Cys Trp Gly Pro Tyr His Val Phe Ser Leu Leu Glu Ala Arg Ala
            260                 265                 270

His Ala Asn Pro Gly Leu Arg Pro Leu Val Trp Arg Gly Leu Pro Phe
        275                 280                 285

Val Thr Ser Leu Ala Phe Phe Asn Ser Val Ala Asn Pro Val Leu Tyr
290                 295                 300

Val Leu Thr Cys Pro Asp Met Leu Arg Lys Leu Arg Arg Ser Leu Arg
305                 310                 315                 320

Thr Val Leu Glu Ser Val Leu Val Asp Asp Ser Glu Leu Gly Gly Ala
                325                 330                 335

Gly Ser Ser Arg Arg Arg Arg Thr Pro Ser Thr Ala Arg Ser Ala
            340                 345                 350

Ser Ser Leu Ala Leu Ser Ser Arg Pro Glu Arg Arg Gly Pro Ala
        355                 360                 365

Arg Leu Phe Gly Trp Leu Leu Gly Gly Cys Ala Ala Ser Pro Gln Arg
370                 375                 380

Gly Pro Leu Asn Arg Ala Leu Ser Ser Thr Ser Ser
385                 390                 395
```

<210> SEQ ID NO 64
<211> LENGTH: 39
<212> TYPE: DNA
<213> ORGANISM: Artificial
<220> FEATURE:
<223> OTHER INFORMATION: description of the artificial sequence: cyno CRTH2 azami-A

<400> SEQUENCE: 64
catggatccg ccaccatgtc cgccaacgcc acgctgaag         39

<210> SEQ ID NO 65
<211> LENGTH: 28
<212> TYPE: DNA
<213> ORGANISM: Artificial
<220> FEATURE:

-continued

```
<223> OTHER INFORMATION: description of the artificial sequence: cyno
      CRTH2 azami-B

<400> SEQUENCE: 65
cataagctta ctcgaggtgc tgctcagc                                          28
```

ANTIBODY WHICH SPECIFICALLY BINDS TO HUMAN CRTH2

CROSS REFERENCE TO RELATED APPLICATION

This is a continuation of U.S. application Ser. No. 15/342,534 filed Nov. 3, 2016 (allowed), which is a continuation of International Application No. PCT/JP2016/071027 filed on Jul. 15, 2016, and claims priority from Japanese Patent Application No. 2015-141633, filed on Jul. 15, 2015, the entire disclosures of which are incorporated herein by reference.

TECHNICAL FIELD

The present invention relates to an anti-human CRTH2 antibody which specifically recognizes and binds to human CRTH2; the antibody fragment thereof; DNA which encodes the amino acid sequence of the antibody; a vector which comprises the DNA; hybridomas and antibody producing cells which produce the antibody; a method of producing the antibody; a composition which comprises the antibody or the antibody fragment thereof; a treatment method and a diagnostic method of an allergic disease, an autoimmune disease, a disease accompanied by increase or hyperergasia of eosinophils, and a disease accompanied by increase or hyperergasia of Th2 cells using the antibody or the antibody fragment thereof; and a medicine and a diagnostic agent which comprise the antibody or the antibody fragment thereof.

BACKGROUND ART

Human CRTH2 (chemoattractant receptor-homologous molecule on Th2 cells) is a seven transmembrane type G protein-coupled receptor (hereinafter, referred to as GPCR) that is also known as the aliases of GPR44, CD294, DP2, and the like. Further, it is known that human CRTH2 is one of receptors of prostaglandin D2 (hereinafter, referred to as PGD2) (Non-Patent Document 1). It is disclosed that CRTH2 was cloned as human Th2-specific protein in 1996 and referred to as B19 (Patent Document 1).

It is known that CRTH2 binds to PGD2 and PGD2 metabolites typified by 13, 14-dihydro-15-keto prostaglandin D2 (hereinafter, referred to as DKPGD2) which are ligands, transmits a Gαi protein-mediated signal into cells, and accordingly, is involved in migration and activation of CRTH2-expressing cells (Non-Patent Document 1).

Human CRTH2 is recognized to be expressed on Th2 cells, eosinophils, basophils, type 2 innate lymphoid cells (hereinafter, referred to as ILC2), or the like (Non-Patent Documents 1 and 2). It is reported that CRTH2 is a surface marker specifically expressed on Th2 cytokine-producing cells (Non-Patent Document 3).

Moreover, ILC2 is a novel cell population involved in allergic responses identified in humans in 2011 and CRTH2 is exemplified as a specific surface marker defining the cells (Non-Patent Document 2). Further, it is reported that CRTH2 is expressed on non-classical monocyte or Th2/Th17 cells (Non-Patent Documents 4 and 5).

In allergic diseases including asthma, it is known that CRTH2-expressing cells contribute to the pathology. It is reported that CRTH2-positive T-cells are recognized at a higher frequency in cells in bronchioalveolar lavage fluid of asthma patients than in cells of the healthy people (Non-Patent Document 6) and CRTH2-positive T-cells increase in correlation with the severity of atopic dermatitis (Non-Patent Document 7).

Since eosinophils contain granule protein having cellular cytotoxicity and deposition of the protein is found in respiratory tract tissues of chronic bronchial asthma patients or lesions of atopic dermatitis patients, it is considered that eosinophils play an important role in pathogenesis of allergic diseases such as chronic bronchial asthma or atopic dermatitis (Non-Patent Documents 8 and 9).

Basophils are involved in induction of an allergic reaction by storing inflammatory molecules such as histamine and leukotriene in cells and releasing them by crosslinking an Fcε receptor or an Fcγ receptor that is expressed on the cell surface to release the molecules (Non-Patent Document 10).

ILC2 is a cell present in a local area such as respiratory tract mucosa or skin. It has characteristics of producing a large amount of Th2 cytokines in response to cytokines such as interleukin (hereinafter, referred to as IL)-25 and IL-33 produced due to tissue injury, and is considered to be involved in pathogenesis of allergic diseases (Non-Patent Document 11).

As monoclonal antibody against CRTH2, 301108 (R&D) is commercially available. Further, BM16 is also known (Patent Document 2). These are rodent antibodies and have not been developed as medicine.

Moreover, it is also disclosed that a recombinant chimeric antibody and a humanized antibody regarding clone 19A2 remove CRTH2-expressing cells by effector activity and a humanized antibody regarding clone 8B1 and mouse antibodies regarding clones 3C12 and 31A5 have antagonist activity against CRTH2.

Further, it is disclosed that an antibody regarding clone 19A2 has reactivity to human mast cells (Patent Document 3).

RELATED ART

Patent Document

[Patent Document 1] Japanese Patent No. 3144805
[Patent Document 2] Pamphlet of International Publication No. 97/46677
[Patent Document 3] Pamphlet of International Publication No. 2014/144865

Non-Patent Document

[Non-Patent Document 1] The Journal of Experimental Medicine, 2001. 193(2): p. 255 to 261.
[Non-Patent Document 2] Nature Immunology, 2011. 12(11): p. 1055 to 1062.
[Non-Patent Document 3] European Journal of Immunology, 2000. 30(10): p. 2972 to 2979.
[Non-Patent Document 4] Blood, 2011. 118(5): e16 to 31
[Non-Patent Document 5] Journal of Allergy and Clinical Immunology, 2014. 134(5): p. 1175 to 1186. e7.
[Non-Patent Document 6] Clinical & Experimental Immunology, 2010. 161(1): p. 34 to 40.
[Non-Patent Document 7] Journal of Investigative Dermatology, 2002. 119(3): p. 609 to 616.
[Non-Patent Document 8] Advances in Immunology, 1986. 39: p. 177 to 253.
[Non-Patent Document 9] Immunology Today, 1992. 13(12): p. 501 to 507.
[Non-Patent Document 10] Journal of Allergy and Clinical Immunology, 2013. 132(4): p. 789 to 801.

[Non-Patent Document 11] Journal of Allergy and Clinical Immunology, 2014. 134(3): p. 671 to 678.

DISCLOSURE OF INVENTION

Problems to be Solved by the Invention

A plurality of human CRTH2 antibodies have been established so far, but there has been a demand for establishment of an anti-human CRTH2 antibody having desired activity such as reactivity to various human immune cells, specific binding activity to human CRTH2, or an effect on human CRTH2 ligand-dependent activity.

An object of the present invention is to provide an anti-human CRTH2 antibody which has desired activity by recognizing and binding to a specific epitope of human CRTH2; the antibody fragment thereof; a DNA which encodes the amino acid sequence of the antibody; a vector which comprises the DNA; hybridomas and antibody producing cells which produce the antibody; a method of producing the antibody; a composition which comprises the antibody or the antibody fragment thereof; a treatment method and a diagnostic method for an allergic disease, an autoimmune disease, a disease accompanied by increase or hyperergasia of eosinophils, and a disease accompanied by increase or hyperergasia of Th2 cells using the antibody or the antibody fragment thereof; and a medicine and a diagnostic agent which comprise the antibody or the antibody fragment thereof.

Means for Solving the Problems

The present invention relates to the following (1) to (26).
(1) An antibody or the antibody fragment thereof which recognizes at least one of 192th glycine and 194th aspartic acid in the amino acid sequence of human CRTH2 represented by SEQ ID NO: 2 and binds thereto.
(2) The antibody or the antibody fragment thereof according to (1), wherein the antibody recognizes at least one amino acid residue selected from the group consisting of 12th proline, 13th isoleucine, 14th leucine, 15th glutamic acid, 177th aspartic acid, 178th glycine, 179th arginine, 180th isoleucine, 181th methionine, 182nd cysteine, 183rd tyrosine, 184th tyrosine, 185th asparagine, 186th valine, 187th leucine, 188th leucine, 189th leucine, 195th arginine, 196th aspartic acid, 197th alanine, and 198th threonine in the amino acid sequence of human CRTH2 represented by SEQ ID NO: 2 and binds thereto.
(3) The antibody or the antibody fragment thereof according to (1) or (2), wherein the antibody recognizes at least one amino acid residue selected from the group consisting of the following (a) to (g):
(a) 12th proline, 14th leucine, and 15th glutamic acid in the amino acid sequence of human CRTH2 represented by SEQ ID NO: 2;
(b) 177th aspartic acid, 178th glycine, and 179th arginine in the amino acid sequence of human CRTH2 represented by SEQ ID NO: 2;
(c) 180th isoleucine and 181st methionine in the amino acid sequence of human CRTH2 represented by SEQ ID NO: 2;
(d): 183rd tyrosine, 184th tyrosine, and 185th asparagine in the amino acid sequence of human CRTH2 represented by SEQ ID NO: 2;
(e) 187th leucine, 188th leucine, and 189th leucine in the amino acid sequence of human CRTH2 represented by SEQ ID NO: 2;

(f) 195th arginine in the amino acid sequence of human CRTH2 represented by SEQ ID NO: 2; and
(g) 196th aspartic acid and 198th threonine in the amino acid sequence of human CRTH2 represented by SEQ ID NO: 2.
(4) The antibody or the antibody fragment thereof according to any one of (1) to (3), wherein the antibody is any one selected from the group consisting of the following (a) to (d):
(a) an antibody in which complementarity determining regions (hereinafter, abbreviated as CDR) 1 to 3 of an antibody heavy chain variable region (hereinafter, abbreviated as VH) comprise amino acid sequences represented by SEQ ID NOS: 20 to 22, respectively, and CDRs 1 to 3 of an antibody light chain variable regions (hereinafter, abbreviated as VL) comprise amino acid sequences represented by SEQ ID NOS: 23 to 25, respectively;
(b) an antibody which comprises VH comprising the amino acid sequence represented by SEQ ID NO: 49 or the amino acid sequence obtained by introducing at least one modification selected from modifications of substituting 18th leucine with methionine, 77th asparagine with serine, 93th valine with threonine, and 117th threonine with valine in the amino acid sequence represented by SEQ ID NO: 49 and VL comprising the amino acid sequence represented by SEQ ID NO: 33 or the amino acid sequence obtained by at least one modification selected from modifications of substituting 2nd isoleucine with valine, 4th methionine with leucine, 15th proline with leucine, and 85th alanine with proline in the amino acid sequence represented by SEQ ID NO: 33;
(c) an antibody which comprises VH comprising any one of the amino acid sequences represented by SEQ ID NOS: 49, 51, 53, 55, 57, and 59 and VL comprising any one of the amino acid sequences represented by SEQ ID NOS: 33, 35, 37, 39, 41, 43, 45, and 47; and
(d) an antibody which comprises VH comprising the amino acid sequence represented by SEQ ID NO: 17 and VL comprising the amino acid sequence represented by SEQ ID NO: 19.
(5) The antibody or the antibody fragment thereof according to any one of (1) to (4), wherein the antibody has at least one characteristic selected from the group consisting of the following (a) to (h):
(a) reactivity of the antibody against human CRTH2 does not decrease in the presence of a ligand of human CRTH2;
(b) neutralizing activity is not shown by the antibody;
(c) antibody-dependent cell-mediated cytotoxicity (ADCC) is shown by the antibody;
(d) a reaction of the antibody with at least one of mast cells and Th1 cells does not occur;
(e) a reaction of the antibody with at least one selected from eosinophils, basophils, Th2 cells, and type 2 innate lymphoid cells (ILC2) occurs;
(f) agonist activity is not shown by the antibody;
(g) a signal caused by the ligand of human CRTH2 is not enhanced by the antibody; and
(h) reactivity of the antibody against human CRTH2 in an activated or inactivated state does not changed.
(6) The antibody or the antibody fragment thereof according to any one of (1) to (5), wherein the antibody comprises a human Fc region.
(7) The antibody or the antibody fragment thereof according to any one of (1) to (6), wherein the antibody is a monoclonal antibody.

(8) The antibody or the antibody fragment thereof according to any one of (1) to (7), wherein the antibody is a recombinant antibody.
(9) The recombinant antibody or the antibody fragment thereof according to (8), wherein the recombinant antibody is any one recombinant antibody selected from a human chimeric antibody, a human CDR-grafted antibody, and a human antibody.
(10) The antibody or the antibody fragment thereof according to any one of (1) to (9), wherein the antibody is an antibody which binds to monkey CRTH2.
(11) The antibody fragment according to any one of (1) to (10), wherein the antibody fragment is any one selected from Fab, Fab', F(ab')$_2$, scFv, diabody, dsFv, and peptide including CDR.
(12) A hybridoma which generates the antibody or the antibody fragment thereof according to any one of (1) to (11).
(13) A DNA which encodes the antibody or the antibody fragment thereof according to any one of (1) to (11).
(14) A recombinant vector which comprises the DNA according to (13).
(15) A transformant which is obtained by introducing the recombinant vector according to (14) into a host cell.
(16) A method of producing the antibody or the antibody fragment thereof according to any one of (1) to (11), comprising:
    culturing the hybridomas according to (12) or the transformant according to (15) in a culture medium;
    producing and accumulating the antibody or the antibody fragment thereof according to any one of (1) to (11) in a culture; and
    collecting the antibody or the antibody fragment thereof from the culture.
(17) A therapeutic agent for a disease associated with human CRTH2, comprising:
    the antibody or the antibody fragment thereof according to any one of (1) to (11) as an active ingredient.
(18) A diagnostic agent for a disease associated with human CRTH2, comprising:
    the antibody or the antibody fragment thereof according to any one of (1) to (11) as an active ingredient.
(19) The agent according to (17) or (18), wherein the disease associated with CRTH2 is an allergic disease; an autoimmune disease; a disease accompanied by at least one of increase and hyperergasia of eosinophils; a disease accompanied by at least one of increase and hyperergasia of Th2 cells; or a disease accompanied by at least one of increase and hyperergasia of type 2 innate lymphoid cells (ILC2).
(20) A method of treating a disease associated with human CRTH2 comprising:
    administrating an effective amount of the antibody or the antibody fragment thereof according to any one of (1) to (11).
(21) A method of diagnosing a disease associated with human CRTH2 comprising:
    administrating an effective amount of the antibody or the antibody fragment thereof according to any one of (1) to (11).
(22) The method according to (20) or (21), wherein the disease associated with human CRTH2 is an allergic disease; an autoimmune disease; a disease accompanied by at least one of increase and hyperergasia of eosinophils; a disease accompanied by at least one of increase and hyperergasia of Th2 cells; or a disease accompanied by at least one of increase and hyperergasia of ILC2.
(23) The antibody or the antibody fragment thereof according to any one of (1) to (11), for a use in at least one of treatment and diagnosis for a disease associated with human CRTH2.
(24) The antibody or the antibody fragment thereof according to (23), wherein the disease associated with human CRTH2 is an allergic disease; an autoimmune disease; a disease accompanied by at least one of increase and hyperergasia of eosinophils; a disease accompanied by at least one of increase and hyperergasia of Th2 cells; or a disease accompanied by at least one of increase and hyperergasia of ILC2.
(25) Use of the antibody or the antibody fragment thereof according to any one of (1) to (11), for the manufacture of at least one of a therapeutic agent and a diagnostic agent for a disease associated with human CRTH2.
(26) The use according to (25), wherein the disease associated with human CRTH2 is an allergic disease; an autoimmune disease; a disease accompanied by at least one of increase and hyperergasia of eosinophils; a disease accompanied by at least one of increase and hyperergasia of Th2 cells; or a disease accompanied by at least one of increase and hyperergasia of ILC2.

Effects of the Invention

According to the present invention, an antibody or the antibody fragment thereof or the like which recognizes at least one of 192th glycine and 194th aspartic acid in the amino acid sequences of human CRTH2 represented by SEQ ID NO: 2 and binds thereto can be provided.
The antibody of the present invention specifically reacts with cells expressing CRTH2 such as eosinophils, basophils, Th2 cells, or ILC2, exhibits high reactivity to CRTH2-expressing cells even in the presence of high concentration of a ligand, and does not have agonist activity, neutralizing activity, or activity of enhancing the signal caused by the ligand of human CRTH2. Therefore, the antibody or the antibody fragment thereof of the present invention is capable of exhibiting therapeutic effects that target the cells expressing CRTH2 such as eosinophils, basophils, Th2 cells, or ILC2 which express CRTH2.

BRIEF DESCRIPTION OF THE DRAWINGS

FIG. 1 shows amino acid sequences of the light chain variable region of Lym2 antibody and the light chain variable region of each humanized Lym2 antibody (LV0, LV1, LV2a, LV2b, LV2c, LV3a, LV3b, and LV4) which do not include signal sequences. The regions surrounded by frames in each sequence show CDR sequences.
FIG. 2 shows amino acid sequences of the heavy chain variable region of Lym2 antibody and the heavy chain variable region of each humanized Lym2 antibody (HV0, HV1, HV2a, HV2b, HV3, and HV4) which do not include signal sequences. The regions surrounded by frames in each sequence show CDR sequences.
FIGS. 3(A) to 3(C) show the results of analyzing cytotoxic activity against human eosinophils and human basophils of rat/human chimeric Lym2 antibody (hereinafter, also referred to as chLym2) and humanized Lym2 antibodies using flow cytometry. In FIGS. 3(A) to 3(C), each of the figures on the left side shows cytotoxic activity against human eosinophils and each of the right figures shows cytotoxic activity against human basophils. The vertical axis in each figure represents the number of cells per 2000 control beads and the horizontal axis in each figure represents the antibody concentration. In FIG. 3(A), ○ represents chLym2, ● represents a humanized Lym2 antibody LV0HV0, and Δ represents an isotype control antibody. In FIG. 3(B), ○ represents chLym2, ■ represents a humanized Lym2 antibody LV0HV1, and Δ represents an isotype control antibody. In FIG. 3(C), ○ represents chLym2, ▲ represents a humanized Lym2 antibody LV0HV2a, and Δ represents an isotype control antibody.

FIG. 4(A) shows reactivity of a humanized Lym2 antibody LV0HV1 against each of cells which express mutated human CRTH2 with amino acid substitution and FIG. 4(B) shows reactivity of chLym2 against each of cells which express mutated human CRTH2 with amino acid substitution. In each figure, the vertical axis represents the value (%) of reactivity against each of cells which express mutated human CRTH2 with amino acid substitution wherein the value of reactivity, which is relative fluorescent intensity obtained by correcting fluorescent intensity of each anti-human CRTH2 monoclonal antibody with fluorescent intensity of Azami-Green tag, against wild-type human CRTH2-expressing cells is set to 100%. In each horizontal axis, WT represents wild-type human CRTH2 and the others represent mutants with amino acid substitution. The symbol "*" means that 90% or greater of relative fluorescent intensity decreases from the relative fluorescent intensity of wild-type CRTH2. Hereinafter, the same applies to FIGS. 5 to 7.

FIG. 5(A) shows reactivity of hu19A2 v52 against each of CRTH2 mutants with amino acid substitution and FIG. 5(B) shows reactivity of hu8B1 v1 against each of CRTH2 mutants with amino acid substitution.

FIG. 6(A) shows reactivity of ch3C12 against each of CRTH2 mutants with amino acid substitution and FIG. 6(B) shows reactivity of ch31A5 against each of CRTH2 mutants with amino acid substitution.

FIG. 7 shows reactivity of BM16 against each of CRTH2 mutants with amino acid substitution.

FIG. 8 shows the results of analyzing reactivity of an anti-human CRTH2 monoclonal antibody against human eosinophils using flow cytometry. ● represents Lym2 antibody, ○ represents BM16, ▲ represents 301108. The vertical axis represents fluorescent intensity, and the horizontal axis represents the antibody concentration of each anti-human CRTH2 monoclonal antibody.

FIG. 9 shows the results of analyzing reactivity of chLym2 against human basophils using flow cytometry. A portion painted with black represents reactivity of an isotype control antibody and a portion surrounded by a solid line represents reactivity of chLym2. The vertical axis represents the number of cells and the horizontal axis represents the fluorescent intensity.

FIG. 10 shows the results of analyzing reactivity of a humanized Lym2 antibody LV0HV1 against human CD4-positive T-cells using flow cytometry. The vertical axis represents fluorescent intensity of fluorescence staining using a humanized Lym2 antibody LV0HV1 against a cell population in which lymphocytes are fractionated by Forward scatter (hereinafter, referred to as FSC)-Side scatter (hereinafter, referred to as SSC) deployment and further fractionated by CD3-positive cells and CD4-positive cells and the horizontal axis represents fluorescent intensity of fluorescence staining resulting from a CD4 antibody with respect to a cell population in which lymphocytes are fractionated by FSC-SSC deployment and further fractionated by CD3-positive cells and CD4-positive cells.

FIG. 11(A) and FIG. 11(B) show the results of analyzing cytotoxic activity of an anti-human CRTH2 monoclonal antibody against human eosinophils and human basophils using flow cytometry. The upper figure shows cytotoxic activity against human eosinophils and the lower figure shows cytotoxic activity against human basophils. In each figure, the vertical axis represents the number of cells per 1000 control beads and the horizontal axis represents the antibody concentration. ○ represents a humanized Lym2 antibody LV0HV1, □ represents hu19A2 v52, ▲ represents hu8B1 v1, Δ represents ch3C12, ♦ represents ch31A5, and x represents an isotype control antibody.

FIG. 12(A) and FIG. 12(B) show the results of analyzing activity of reducing human Th2 and Th1 cytokine of an anti-human CRTH2 monoclonal antibody. In FIG. 12(A), the vertical axis represents the concentration of IL-5 or IL-13 which is Th2 cytokine under the condition that each antibody is added. Further, in FIG. 12(B), the vertical axis represents the concentration of IFN-γ which is Th1 cytokine under the condition that each antibody is added.

FIGS. 13(A) to 13(C) show results of analyzing a change in reactivity of an anti-human CRTH2 monoclonal antibody in the presence of DKPGD2 which is a CRTH2 ligand using human CRTH2 expressing 293 EBNA cells using flow cytometry. When the concentrations of the anti-human CRTH2 monoclonal antibody shown in the legends are 0.3 μg/mL, 1 μg/mL, and 3 μg/mL, the results thereof are shown in FIG. 13(A), FIG. 13(B), and FIG. 13(C), respectively. In each figure, the vertical axis represents the percentage of fluorescent intensity when the fluorescent intensity in the absence of DKPGD2 is set to 100%.

FIG. 14 shows the results of analyzing reactivity of an anti-human CRTH2 monoclonal antibody against human differentiation induced mast cells stimulated by IgE and a crosslinking antibody treatment using flow cytometry. Each figure shows reactivity of an antibody described on the top of each figure. The vertical axis represents the number of cells and the horizontal axis represents the fluorescent intensity. A portion painted with black represents reactivity of an isotype control antibody and a portion surrounded by a solid line represents reactivity of the anti-human CRTH2 monoclonal antibody.

FIG. 15 shows the results of analyzing reactivity of an anti-human CRTH2 monoclonal antibody against human differentiation induced Th1 cells using flow cytometry. Each figure shows reactivity of an antibody described on the top of each figure. The vertical axis represents the number of cells and the horizontal axis represents the fluorescent intensity. A portion painted with black represents reactivity of an isotype control antibody and a portion surrounded by a solid line represents reactivity of the anti-human CRTH2 monoclonal antibody.

FIG. 16 shows the results of evaluation of antagonist activity of Lym2 antibody using shape change of human eosinophils as an index. The vertical axis represents the percentage (%) of eosinophils detected in a high FSC region by flow cytometer analysis when DKPGD2 was treated at the concentrations shown in the legends in the presence or absence of each antibody described on the bottom of the graph.

FIG. 17 shows the results of evaluation of antagonist activity of Lym2 antibody using shape change of human eosinophils as an index. The vertical axis represents the percentage (%) of eosinophils detected in a high FSC region when the Lym2 antibody was treated at the concentrations shown in the legends.

FIGS. 18(A) to 18(C) all show the results of evaluation of agonist activity, antagonist activity and enhancing activity of ligand-induced activation of an anti-human CRTH2 monoclonal antibody using shape change of human eosinophils as an index. FIG. 18(A) shows the result regarding a humanized antibody or a chimeric antibody, FIG. 18(B) shows the result regarding a rat antibody, and FIG. 18(C) shows the result regarding a mouse antibody. In each figure, the vertical axis represents the percentage (%) of eosinophils detected in a high FSC region by flow cytometer analysis when each anti-human CRTH2 monoclonal antibody or isotype antibody shown in the legends is treated in the presence or absence of DKPGD2.

FIG. 19 shows the results of analyzing an effect of a change in conformation of CRTH2, caused by GTPγS or GDP treatment applied to membrane fraction of CRTH2-expressing cells, on the reactivity of a CRTH2 monoclonal antibody by ELISA. The vertical axis represents Fold change where the absorbance when GTPγ and GDP are untreated is set to 1. The horizontal axis represents the presence or absence of GTPγS and GDP treatment and evaluated antibodies (hu19A2 v52 and a humanized Lym2 antibody LV0HV1).

FIG. 20 shows the results of analyzing Azami-Green expression in Azami-Green fusion human CRTH2 expressing CHO/DG44 cells and cynomolgus monkey CRTH2 expressing CHO/DG44 cells using flow cytometry. The vertical axis represents the number of cells and the horizontal axis represents fluorescent intensity of Azami-Green. A portion pained with black represents fluorescent intensity in CHO/DG44 cells which are parent cells, a portion surrounded by a solid line represents fluorescent intensity in Azami-Green fusion human CRTH2 expressing CHO/DG44 cells, and a portion surrounded by a dotted line represents fluorescent intensity in Azami-Green fusion cynomolgus monkey CRTH2 expressing CHO/DG44 cells.

FIG. 21 shows the results of analyzing reactivity of a humanized Lym2 antibody LV0HV1 and an isotype antibody against Azami-Green fusion human CRTH2 expressing CHO/DG44 cells and cynomolgus monkey CRTH2 expressing CHO/DG44 cells using flow cytometry. ○ represents reactivity of LV0HV1 against Azami-Green fusion human CRTH2 expressing CHO/DG44 cells, ● represents reactivity of LV0HV1 against Azami-Green fusion cynomolgus monkey CRTH2 expressing CHO/DG44 cells, △ represents reactivity of an isotype antibody against Azami-Green fusion human CRTH2 expressing CHO/DG44 cells, and ▲ represents reactivity of an isotype antibody against Azami-Green fusion cynomolgus monkey CRTH2 expressing CHO/DG44 cells. Further, the vertical axis represents fluorescent intensity and the horizontal axis represents the antibody concentration of each antibody.

EMBODIMENTS FOR CARRYING OUT THE INVENTION

As human CRTH2 in the present invention, a polypeptide comprising the amino acid sequence represented by SEQ ID NO: 2 or GenBank accession number BAA74518 may be exemplified. A polypeptide comprising an amino acid sequence, in which one or more amino acids are deleted, substituted, inserted, and/or added in the amino acid sequence represented by SEQ ID NO: 2 or GenBank accession number BAA74518, and has a function of human CRTH2 and a polypeptide which is formed of an amino acid sequence having 60% or greater, preferably 80% or greater, more preferably 90% or greater, still more preferably 95% or greater, and most preferably 98% or greater homology with the amino acid sequence represented by SEQ ID NO: 2 or GenBank accession number BAA74518 and having a function of human CRTH2 are incorporated in human CRTH2 of the present invention.

A polypeptide comprising an amino acid sequence represented by SEQ ID NO: 2 or GenBank accession number BAA74518, in which one or more amino acids are deleted, substituted, inserted, and/or added can be obtained by site-directed mutagenesis [Molecular Cloning, A Laboratory Manual, Second Edition, Cold Spring Harbor Laboratory Press (1989), Current Protocols in Molecular Biology, John Wiley & Sons (1987 to 1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985)], for example, by introducing site-directed mutation to DNA that encodes a polypeptide comprising the amino acid sequence represented by SEQ ID NO: 2. The number of amino acids to be deleted, substituted, or added is not particularly limited, but preferably in a range of 1 to several tens of amino acids, for example, 1 to 20 amino acids and more preferably in a range of 1 to several amino acids, for example, 1 to 5 amino acids.

As a gene encoding human CRTH2, a base sequence represented by GenBank accession number AB008535 or SEQ ID NO: 1 may be exemplified. A gene which comprises a base sequence represented by GenBank accession number AB008535 or SEQ ID NO: 1 in which one or more base is deleted, substituted, or added and includes DNA which encodes a protein having a function of human CRTH2; a gene which comprises a base sequence having at least 60% or greater, preferably 80% or greater, and more preferably 95% or greater homology with the base sequence represented by GenBank accession number AB008535 or SEQ ID NO: 1 and comprises DNA which encodes a polypeptide having a function of human CRTH2; and a gene which comprises DNA hybridizing with DNA comprising the base sequence represented by SEQ ID NO: 1 under stringent conditions and comprises DNA encoding a polypeptide having a function of human CRTH2 are included in the genes encoding CRTH2 of the present invention.

The DNA hybridizing under stringent conditions indicates DNA which is obtained by a colony hybridization method, a plaque hybridization method, a southern blot hybridization method, or a DNA microarray method using DNA comprising the base sequence represented by SEQ ID NO: 1 as a probe and is capable of hybridizing.

Specifically, DNA which can be identified by performing hybridization at 65° C. in the presence of 0.7 to 1.0 mol/L of sodium chloride using a filter or a slide glass with a hybridized colony- or plaque-derived DNA, a PCR product comprising the sequence or an oligo DNA immobilizing there on, and then washing the filter or slide glass at 65° C. with 0.1 to 2-fold concentration of SSC solution (SSC solution having a 1-fold concentration consists of 150 mmol/L of sodium chloride and 15 mmol/L of sodium citrate) [Molecular cloning, A Laboratory Manual, Second Edition, Cold Spring Harbor Laboratory Press (1989), Current Protocols in Molecular Biology, John Wiley & Sons (1987 to 1997), DNA Cloning 1: Core Techniques, A Practical Approach, Second Edition, Oxford University, (1995)] may be exemplified.

As DNA which is capable of hybridizing, DNA having at least 60% or greater, preferably 80% or greater, and more preferably 95% or greater homology with the base sequence represented by GenBank accession number AB008535 or SEQ ID NO: 1 may be exemplified.

In a base sequence of a gene which encodes protein of a eukaryote, gene polymorphism is frequently found. A gene in which a base sequence of genes used in the present invention is mutated in a small scale by such polymorphism is also included in genes encoding human CRTH2 of the present invention.

The value of homology in the present invention may be a value calculated using a homology search program known to those skilled in the art unless otherwise noted. Further, in regard to base sequences, values calculated using default parameters in BLAST [J. Mol. Biol., 215, 403 (1990)] and the like may be exemplified. In regard to amino acid sequences, values calculated using default parameters in BLAST2 [Nucleic Acids Res., 25, 3389 (1997), Genome Res., 7, 649 (1997), http://www.ncbi.nlm.nih.gov/Education/BLASTinfo/information3.html] and the like may be exemplified.

As the default parameters, G (Cost to open gap) is 5 for a base sequence and 11 for an amino acid sequence; -E (Cost to extend gap) is 2 for a base sequence and 1 for an amino acid sequence; -q (Penalty for nucleotide mismatch) is −3; -r (reward for nucleotide match) is 1; -e (expect value) is 10, -W (wordsize) is 11 residues for a base sequence and 3 residues for an amino acid sequence; -y [Dropoff (X) for blast extensions in bits] is 20 for blastn and 7 for a program other than blastn; -X (X dropoff value for gapped alignment in bits) is 15; and -Z (final X dropoff value for gapped alignment in bits) is 50 for blastn and 25 for a program other than blastn (http://www.ncbi.nlm.nih.gob/blast/html/blastcgihelp.html).

The polypeptide comprising a partial sequence of the amino acid sequence represented by SEQ ID NO: 2 or GenBank accession number BAA74518 can be produced by a method known to those skilled in the art. For example, it can be produced by deleting a part of DNA encoding the amino acid sequence represented by SEQ ID NO: 2 and culturing a transformant into which an expression vector containing the DNA is introduced. In addition, using the same method as described above, a polypeptide comprising an amino acid sequence represented by the partial sequence of the amino acid represented by SEQ ID NO: 2 or GenBank accession number BAA74518 in which one or more amino acids are deleted, substituted, or added can be obtained based on the polypeptide or the DNA produced according to the above-described method. Moreover, the polypeptide comprising a partial sequence of the amino acid sequence represented by SEQ ID NO: 2 or GenBank accession number BAA74518 or the polypeptide comprising the partial sequence of the amino acid represented by SEQ ID NO: 2 or GenBank accession number BAA74518 in which one or more amino acids are deleted, substituted, or added can be produced using a chemical synthesis method such as a fluorenylmethyloxycarbonyl (Fmoc) method or a t-butyloxycarbonyl (tBoc) method.

Examples of the functions of human CRTH2 include migration of cells expressing human CRTH2, enhancement of production of cytokine from the cells, and induction of a change in cell shape accompanied by a change in diameter or surface area in cells by human CRTH2-dependent intracellular signal transduction caused by binding to the ligand thereof, for example, PGD2.

Examples of extracellular regions of human CRTH2 include an N-terminal region comprising 1st to 33th amino acid residues; a loop 1 region comprising 95th to 111st amino acid residues; a loop 2 region comprising 169th to 206th amino acid residues; and a loop 3 region comprising 264th to 285th amino acid residues [J Immunol, 1999. 162(3): p. 1278 to 1286] in the amino acid sequence of human CRTH2 represented by SEQ ID NO: 2. As the N-terminal region, the loop 1 region, the loop 2 region, and the loop 3 region, specifically, polypeptide portions comprising 1st to 33th amino acid residues, 95th to 111th amino acid residues, 169th to 206th amino acid residues, and 264th to 285th amino acid residues in the amino acid sequence represented by SEQ ID NO: 2, respectively, may be exemplified.

The antibody of the present invention may be any kind of antibody such as a monoclonal antibody or a polyclonal antibody, but a monoclonal antibody is preferable: Specific examples of the antibody of the present invention include an antibody produced by hybridomas or a recombinant antibody produced by a recombinant DNA technology. Further, examples of the recombinant antibody include a mouse antibody, a rat antibody, a human chimeric antibody, a humanized antibody, and a human antibody produced by a recombinant DNA technology.

The monoclonal antibody is an antibody secreted by antibody-producing cells of a single clone and recognizes only one epitope (also referred to as antigenic determinant), and amino acid sequences (primary structure) constituting the monoclonal antibody are uniform.

Examples of the monoclonal antibody of the present invention include recombinant antibodies produced using a recombinant DNA technology such as an antibody produced by hybridomas and an antibody produced by a transformant transformed by an expression vector including antibody genes.

The polyclonal antibody is an antibody group including two or more monoclonal antibodies and a plurality of epitopes can be recognized by a plurality of antibodies constituting the antibody group.

Example of the epitope of the present invention include a single amino acid sequence, a three-dimensional structure comprising the amino acid sequence, an amino acid sequence modified by post-translational modification, and a three-dimensional structure comprising the amino acid sequence, and the like which is recognized and bound by the antibody.

As the amino acid sequence modified by post-translational modification, an amino acid sequence which is bound by an O-binding type sugar chain in which sugar chain binds to threonine and serine which have a OH substituent, a N-binding type sugar chain in which a sugar chain binds to glutamine and asparagine which have a $NH_2$ substituent, a sulfate group in which a sulfuric acid molecule binds to threonine which has a OH substituent, or the like may be exemplified.

The epitope of human CRTH2 recognized by the antibody of the present invention can be determined by performing a binding experiment of an antibody using a deletion variant obtained by deleting a domain as a part of human CRTH2, a mutant obtained by substituting an amino acid residue as a part of human CRTH2 with another amino acid residue, a mutant substituted with a domain derived from other proteins, and a partial peptide fragment of human CRTH2 and the like. Further, the epitope of human CRTH2 to which the antibody of the present invention binds can be determined by adding the antibody of the present invention to human CRTH2 digested by a protease and performing epitope mapping using known mass spectrometry.

As the amino acid residue included in the epitope of human CRTH2 recognized by the antibody of the present invention, an amino acid residue identified by the loss of reactivity of the antibody of the present invention due to substitution of the amino acid residue may be exemplified.

The reactivity of the antibody of the present invention can be determined, for example, by measuring the amount (corrected according to the amount of the wild-type human CRTH2 receptor or the mutant with amino acid substitution to be expressed) of the antibody which bind to cells expressing a wild-type human CRTH2 receptor or a mutant with amino acid substitution using flow cytometry or the like. Further, the amount of the antibody which bind can be confirmed by radioimmunoassay using a solid-phase sandwich method or the like; a known immunological detection method with respect to human CRTH2 using an enzyme immunoassay (ELISA) method or the like; or a surface plasmon resonance method using a Biacore system (GE Healthcare) or the like.

Further, the amount can be confirmed by combining a known immunological detection method [Monoclonal Antibodies—Principles and Practice, Third edition, Academic Press (1996), Antibodies—A Laboratory Manual, Cold Spring Harbor Laboratory (1988), monoclonal antibody experiment manual, Kodansha Scientific (1987)] or the like.

The expression of "the reactivity of the antibody of the present invention is lost" means that the reactivity of the antibody against cells expressing a mutant with amino acid substitution decreases by 70% or greater, preferably 80% or greater, more preferably 90% or greater, and still more preferably 95% or greater, compared to reactivity of the antibody against cells expressing wild-type human CRTH2.

As the epitope to which the antibody of the present invention binds, an epitope comprising at least one amino acid residue of 192th glycine and 194th aspartic acid in the amino acid sequence of human CRTH2 represented by SEQ ID NO:2 may be exemplified.

Moreover, specific examples of the epitope to which the antibody of the present invention binds include the following epitopes (a) to (c).

(a) an epitope comprising 192th glycine in the amino acid sequence of human CRTH2 represented by SEQ ID NO: 2;

(b) an epitope comprising 194th aspartic acid in the amino acid sequence of human CRTH2 represented by SEQ ID NO: 2; and (c) an epitope comprising 192th glycine and 194th aspartic acid in the amino acid sequence of human CRTH2 represented by SEQ ID NO: 2.

Moreover, examples of the epitope to which the antibody of the present invention binds include an epitope which comprises at least one amino acid residue of 192nd glycine and 194th aspartic acid in the amino acid sequence of human CRTH2 represented by SEQ ID NO: 2 and comprises at least one amino acid residue selected from the group consisting of 12th proline, 14th leucine, 15th glutamic acid, 177th aspartic acid, 178th glycine, 179th arginine, 180th isoleucine, 181th methionine, 183rd tyrosine, 184th tyrosine, 185th asparagine, 187th leucine, 188th leucine, 189th leucine, 195th arginine, 196th aspartic acid, and 198th threonine in the amino acid sequences of human CRTH2 represented by SEQ ID NO: 2.

Moreover, examples of the epitope to which the antibody of the present invention binds include an epitope which comprises at least one amino acid residue of 192th glycine and 194th aspartic acid in the amino acid sequence of human CRTH2 represented by SEQ ID NO: 2 and includes at least one of the following (a) to (g).

(a) 12th proline, 14th leucine, and 15th glutamic acid in the amino acid sequences of human CRTH2 represented by SEQ ID NO: 2;

(b) 177th aspartic acid, 178th glycine, and 179th arginine in the amino acid sequences of human CRTH2 represented by SEQ ID NO: 2;

(c) 180th isoleucine and 181st methionine in the amino acid sequences of human CRTH2 represented by SEQ ID NO: 2;

(d): 183rd tyrosine, 184th tyrosine, and 185th asparagine in the amino acid sequences of human CRTH2 represented by SEQ ID NO: 2;

(e) 187th leucine, 188th leucine, and 189th leucine in the amino acid sequences of human CRTH2 represented by SEQ ID NO: 2;

(f) 195th arginine in the amino acid sequences of human CRTH2 represented by SEQ ID NO: 2; and (g) 196th aspartic acid and 198th threonine in the amino acid sequences of human CRTH2 represented by SEQ ID NO: 2.

Other amino acid residue included in the epitope to which the antibody of the present invention binds is not particularly limited as long as the amino acid residue is present in the amino acid sequence of human CRTH2 represented by SEQ ID NO: 2 and substantially recognized and binded when the antibody of the present invention binds to human CRTH2, and specific examples thereof include an amino acid residue present, on the three-dimensional structure, in the vicinity of the amino acid residue selected from the group consisting of 12th proline, 14th leucine, 15th glutamic acid, 177th aspartic acid, 178th glycine, 179th arginine, 180th isoleucine, 181st methionine, 183rd tyrosine, 184th tyrosine, 185th asparagine, 187th leucine, 188th leucine, 189th leucine, 192nd glycine, 194th aspartic acid, 195th arginine, 196th aspartic acid, and 198th threonine in the amino acid sequences of human CRTH2 represented by SEQ ID NO: 2; and an amino acid residue present, in the primary sequence, in the vicinity of the amino acid sequence selected from amino acids selected from the group consisting of 12th proline, 14th leucine, 15th glutamic acid, 177th aspartic acid, 178th glycine, 179th arginine, 180th isoleucine, 181st methionine, 183rd tyrosine, 184th tyrosine, 185th asparagine, 187th leucine, 188th leucine, 189th leucine, 192nd glycine, 194th aspartic acid, 195th arginine, 196th aspartic acid, and 198th threonine in the amino acid sequences of human CRTH2 represented by SEQ ID NO: 2.

An antibody molecule is also referred to as immunoglobulin (hereinafter, referred to as Ig) and human antibodies are classified into isotypes of IgA1, IgA2, IgD, IgE, IgG1, IgG2, IgG3, IgG4, and IgM according to a difference in molecular structure. IgG1, IgG2, IgG3, and IgG4 having relatively high homology of an amino acid sequence are also collectively referred to as IgG.

An antibody molecule is constituted with a polypeptide referred to as a heavy chain (hereinafter, referred to as an H chain) and a polypeptide referred to as a light chain (hereinafter, referred to as an L chain). Further, the H chain is constituted with each region of an H chain variable region (also referred to as VH) and an H chain constant region (also referred to as CH) from the N terminal side and the L chain is constituted with each region of an L chain variable region (also referred to as VL) and an L chain constant region (also referred to as CL) from the N terminal side.

In the CH, an α chain, a δ chain, a ε chain, a γ chain, and a μ chain are known for each sub-class. The CH is constituted with each domain of a CH1 domain, a hinge domain, a CH2 domain, and a CH3 domain from the N terminal side. A domain indicates a functional structural unit constituting each polypeptide of an antibody molecule. Moreover, the CH2 domain and the CH3 domain are collectively referred to as an Fc region or simply referred to as Fc. In the CL, a Cλ chain and a Cκ chain are known.

The CH in the antibody of the present invention is not particularly limited as long as the CH belongs to Ig, but any one of the IgG class is preferable and any one in the sub-class such as IgG1, IgG2, IgG3, or IgG4 belonging to the IgG class can be also used.

The amino acid sequence of the CL in the antibody of the present invention may be any of an amino acid sequence of a human antibody or an amino acid sequence of a non-human animal antibody, but Cκ or Cλ of an amino acid sequence of a human antibody is preferable.

The antibody of the present invention is an antibody that recognizes at least one amino acid residue of 192th glycine and 194th aspartic acid in the amino acid sequence of human CRTH2 represented by SEQ ID NO: 2 and binds thereto.

Specific examples of the antibody of the present invention include an antibody selected from the following (a) to (c).

(a) An antibody which recognizes 192th glycine in the amino acid sequence of human CRTH2 represented by SEQ ID NO: 2 and binds thereto;

(b) An antibody which recognizes 194th aspartic acid in the amino acid sequence of human CRTH2 represented by SEQ ID NO: 2 and binds thereto; and (c) An antibody which recognizes both of 192th glycine and 194th aspartic acid in the amino acid sequence of human CRTH2 represented by SEQ ID NO: 2 and binds thereto.

Further, as the antibody of the present invention, an antibody which recognizes at least one amino acid residue of 192nd glycine and 194th aspartic acid in the amino acid sequence of human CRTH2 represented by SEQ ID NO: 2 and recognizes at least one amino acid residue selected from the group consisting of 12nd proline, 14th leucine, 15th glutamic acid, 177th aspartic acid, 178th glycine, 179th arginine, 180th isoleucine, 181st methionine, 183rd tyrosine, 184th tyrosine, 185th asparagine, 187th leucine, 188th leucine, 189th leucine, 195th arginine, 196th aspartic acid, and 198th threonine in the amino acid sequences of human CRTH2 represented by SEQ ID NO: 2 and binds thereto may be exemplified.

Further, as the antibody of the present invention, an antibody which recognizes at least one amino acid residue of 192th glycine and 194th aspartic acid in the amino acid sequence of human CRTH2 represented by SEQ ID NO: 2 and recognizes at least one of the following (a) to (g) and binds thereto may be exemplified.

(a) 12th proline, 14th leucine, and 15th glutamic acid in the amino acid sequences of human CRTH2 represented by SEQ ID NO: 2;

(b) 177th aspartic acid, 178th glycine, and 179th arginine in the amino acid sequences of human CRTH2 represented by SEQ ID NO: 2;

(c) 180th isoleucine and 181th methionine in the amino acid sequences of human CRTH2 represented by SEQ ID NO: 2;

(d): 183th tyrosine, 184th tyrosine, and 185th asparagine in the amino acid sequences of human CRTH2 represented by SEQ ID NO: 2;

(e) 187th leucine, 188th leucine, and 189th leucine in the amino acid sequences of human CRTH2 represented by SEQ ID NO: 2;

(f) 195th arginine in the amino acid sequences of human CRTH2 represented by SEQ ID NO: 2; and (g) 196th aspartic acid and 198th threonine in the amino acid sequences of human CRTH2 represented by SEQ ID NO: 2.

Specific examples of the antibody of the present invention include an antibody selected from the following (a) to (d).

(a) An antibody in which the amino acid sequences of complementary determining regions (CDRs, hereinafter, abbreviated as CDRs) 1 to 3 of VH comprises the amino acid sequences represented by SEQ ID NOS: 20, 21, and 22, respectively, and the amino acid sequences of CDRs 1 to 3 of VL includes the amino acid sequences represented by SEQ ID NOS: 23, 24, and 25, respectively;

(b) An antibody which competes with the above-described antibody (a) and binds to human CRTH2;

(c) An antibody which binds to an epitope having an epitope to which the above-described antibody (a) binds; and (d) An antibody which binds to the same epitope as the epitope to which the above-described antibody (a) binds.

The above-described antibody (b) of the present invention indicates an anti-human CRTH2 antibody which inhibits the binding of the above-described antibody (a) to human CRTH2. Further, in a case where the above-described antibody (a) is set to a first antibody and the epitope to which the first antibody binds is set to a first epitope, the above-described antibody (c) of the present invention indicates an antibody which binds to an epitope having the first epitope.

Further, specific examples of the antibody of the present invention include an antibody selected from the following (a) to (c).

(a) An antibody which comprises VH comprising the amino acid sequence represented by SEQ ID NO: 49 or the amino acid sequence which is obtained by introducing at least one modification selected from modifications of substituting 18th leucine with methionine, 77th asparagine with serine, 93th valine with threonine, and 117th threonine with valine in the amino acid sequence represented by SEQ ID NO: 49 and VL comprising the amino acid sequence represented by SEQ ID NO: 33 or the amino acid sequence which is obtained by introducing at least one modification selected from modifications of substituting 2th isoleucine with valine, 4th methionine with leucine, 15th proline with leucine, and 85th alanine with proline in the amino acid sequence represented by SEQ ID NO: 33;

(b) An antibody which comprises VH comprising any one of the amino acid sequences represented by SEQ ID NOS: 49, 51, 53, 55, 57, and 59 and VL comprising any one of the amino acid sequences represented by SEQ ID NOS: 33, 35, 37, 39, 41, 43, 45, and 47; and (c) An antibody which comprises VH comprising the amino acid sequence represented by SEQ ID NO: 17 and VL comprising the amino acid sequence represented by SEQ ID NO: 19.

Preferred examples of the above-described antibody (b) include an antibody selected from the following (1) to (3).

(1) An antibody which comprises VH comprising the amino acid sequence represented by SEQ ID NO: 49 and VL comprising any one of the amino acid sequences represented by SEQ ID NOS: 33, 35, 37, 39, 41, 43, 45, and 47;

(2) An antibody which comprises VH comprising the amino acid sequence represented by SEQ ID NO: 59 and VL comprising any one of the amino acid sequences represented by SEQ ID NOS: 33, 35, 37, 39, 41, 43, 45, and 47; and (3) An antibody which comprises VH comprising any one of the amino acid sequences represented by SEQ ID NOS: 51, 53, 55, and 57 and VL comprising the amino acid sequence represented by SEQ ID NO: 33.

Particularly preferred examples of the above-described antibody (b) include an antibody which comprises VH comprising the amino acid sequence represented by SEQ ID NO: 51 and VL comprising the amino acid sequence represented by SEQ ID NO: 33.

As the antibody of the present invention, an antibody whose reactivity against a mutant with amino acid substitution obtained by substituting at least one of 192th glycine and 194th aspartic acid of human CRTH2 with alanine is lost may be exemplified.

Further, the antibody of the present invention includes an antibody whose reactivity against human CRTH2 does not decrease in the presence of a ligand of human CRTH2. The antibody whose reactivity against human CRTH2 does not decrease in the presence of the ligand of human CRTH2 is capable of exhibiting high reactivity under conditions in which the ligand of human CRTH2 is present at a high concentration such as a local inflammation area, compared to an antibody whose reactivity against human CRTH2 decreases. Accordingly, the antibody can specifically bind to human CRTH2 in a human CRTH2 ligand-independent manner and thus drug efficacy can be exhibited.

In the present invention, the expression of "the reactivity of the antibody decreases in the presence of a ligand of human CRTH2" means that the reactivity of the antibody against human CRTH2-expressing cells decreases by 5% or greater in the presence of the ligand of human CRTH2 compared to the reactivity in the absence of the ligand of human CRTH2. More precisely, the expression means that the reactivity decreases by 10% or greater.

The ligand of human CRTH2 is not particularly limited as long as the ligand specifically binds to human CRTH2, and preferred examples thereof include PGD2 and DKPGD2. Among the examples, DKPGD2 is more preferable.

In the present invention, the expression of "the reactivity against human CRTH2 in the activated or inactivated state does not change" means that the reactivity of the antibody against human CRTH2 does not change in the presence or absence of guanosine diphosphate (GDP), GDP analog, guanosine triphosphate (GTP), or GTP analog.

As the GDP analog, guanosine 5'-O-(β-thio) diphosphate (GDPβS) may be exemplified. As the GTP analog, guanosine 5'-O-(γ-thio) triphosphate (GTPγS) may be exemplified.

The antibody of the present invention include an antibody which does not have neutralizing activity, an antibody which does not have agonist activity, an antibody which does not enhance the signal caused by the ligand of human CRTH2, and an antibody whose reactivity against human CRTH2 in the activated or inactivated state does not change.

In the present invention, the neutralizing activity of the antibody indicates activity of inhibiting biological activity of human CRTH2 of the antibody. Examples thereof include antagonist activity such as activity of inhibiting binding of human CRTH2 to the ligand thereof or activity of inhibiting transduction of the signal caused by the human CRTH2.

In the present invention, the agonist activity indicates activity that mimics biological activity of the ligand of human CRTH2 such as activity of inducing activation of CRTH2 or various reactions accompanied by the activation. Specific examples of the agonist activity of the present invention include cell migration activity and activity of inducing cell shape change.

In the present invention, the signal caused by the ligand of human CRTH2 indicates the signal as a consequence of activation of human CRTH2 by binding of the ligand of human CRTH2.

The signal caused by the ligand of human CRTH2 and the agonist activity can be evaluated by analyzing various reactions as a consequence of activation of human CRTH2. For example, the signal and the agonist activity can be evaluated by analyzing shape change of human CRTH2-expressing cells.

Any cells may be used as human CRTH2-expressing cells as long as the cells express human CRTH2, and examples thereof include eosinophils, basophils, Th2 cells, type 2 innate lymphoid cells (ILC2), non-classical monocyte, and Th2/Th17 cells.

In the present invention, the expression of "the antibody does not enhance the signal caused by the ligand of human CRTH2" indicates that activation of human CRTH2 and various reactions as a consequence of the activation are not enhanced when human CRTH2 is treated with both of the ligand of human CRTH2, compared to a case where human CRTH2 is treated with only the ligand of human CRTH2.

The antibody of the present invention includes an antibody exhibiting cytotoxic activity against human CRTH2-expressing cells. Examples of the cytotoxic activity of the present invention include complement-dependent cytotoxic activity (hereinafter, referred to as CDC activity) and antibody-dependent cellular cytotoxic activity (hereinafter, referred to as ADCC activity).

As the CDC activity of the present invention, a reaction in which an antibody molecule which binds to human CRTH2 on the cell surface binds to C1q of a complement system through an Fc portion and, as a result, each complement component from C1 to C9 is activated so that C5 to C9 finally form a hole-forming polymer referred to as a membrane attack complex on the cell membrane to cause cytolysis may be exemplified [Immunol Today. 1999 December; 20(12): 576 to 82]

As the ADCC activity of the present invention, a cytotoxic response caused by release of cytotoxic molecules such as perforin and granzyme or enhancement of phagocytosis caused by activation of Fc receptor-expressing cells such as natural killer cells (hereinafter, referred to as NK cells) through the Fc portion by binding of an antibody molecule, which binds to human CRTH2 on the cell surface may be exemplified [Chemical Immunology, 65, 88 (1997); Immunol Today, 20, 576 (1999)].

The antibody of the present invention includes an antibody which does not have cellular cytotoxicity against mast cells. Such an antibody has an advantage that there is no fear of side effect caused by release of an inflammatory mediator due to the injury of the mast cells.

The antibody of the present invention include an antibody in which a N-glycoside-linked sugar chain binds to an Fc region of the antibody and fucose does not bind to N-acetyl glucosamine of a reducing terminal of the N-glycoside-linked sugar chain. As the antibody in which a N-glycoside-linked sugar chain binds to an Fc region of the antibody and fucose does not bind to N-acetyl glucosamine of a reducing terminal of the N-glycoside-linked sugar chain, an antibody produced using CHO cells (Pamphlet of International Publication No. 2005/035586, Pamphlet of International Publication No. 02/31140) in which α1,6-fucose transferase genes are deficient may be exemplified. The antibody of the present invention in which a N-glycoside-linked sugar chain binds to an Fc region of the antibody and fucose does not bind to N-acetyl glucosamine of a reducing terminal of the N-glycoside-linked sugar chain has high ADCC activity.

The antibody of the present invention includes an antibody in which amino acid residues of an Fc region of the antibody are modified such that the binding activity of the amino acid residues to an Fc receptor becomes high. As the antibody in which amino acid residues of an Fc region of the antibody are modified such that the binding activity to an Fc receptor becomes high, and antibody molecules produced by a method described in U.S. Pat. No. 7,317,091 may be exemplified.

The antibody of the present invention include an antibody in which the surface charge of a polypeptide comprising a variable region of the antibody or an antigen-binding activity in the pH in an early endosome is modified so that half-life in blood is extended.

As the antibody in which the surface charge of a polypeptide comprising a variable region of the antibody molecule or antigen-binding activity in the pH in an early endosome is modified so that half-life in blood is extended, antibodies produced by the methods described in JP-A-2013-165716 and JP-A-2012-021004A may be exemplified.

The antibody of the present invention include recombinant antibodies such as a human chimeric antibody (hereinafter, also simply referred to as a chimeric antibody), a human CDR-grafted antibody (hereinafter, also referred to as a humanized antibody), and a human antibody.

The chimeric antibody indicates an antibody comprising VH and VL of an antibody of animal other than humans (non-human animal) and a CH and a CL of a human antibody. Any animal such as a mouse, a rat, a hamster, or a rabbit can be used as the non-human animal as long as hybridomas can be prepared.

The chimeric antibody of the present invention can be produced by obtaining cDNA that encodes the VH and the VL of an antibody of a non-human animal specifically reacting with human CRTH2, inserting the cDNA into an expression vector for animal cell comprising genes encoding the CH and the CL of a human antibody, respectively, and thus constructing a chimeric antibody expression vector and by introducing the vector into animal cells to express the antibody.

The humanized antibody indicates an antibody in which the CDRs of the VH and the VL of an antibody of an animal other than humans is grafted into suitable positions in the VH and the VL of a human antibody.

The humanized antibody of the present invention can be produced by constructing cDNA that encodes a variable region (hereinafter, also referred to as a V region) constructed by grafting the CDRs of the VH and the VL of an antibody of a non-human animal specifically reacting with human CRTH2 to a framework (hereinafter, also referred to as an FR) of the VH and the VL of a suitable human antibody, inserting the cDNA into an expression vector for animal cell comprising DNA encoding the CH and the CL, respectively, and thus constructing a humanized antibody expression vector and by introducing the vector into animal cells to express the antibody.

Any amino acid sequence can be used as the amino acid sequence of the FR of the VH and the VL of a human antibody as long as the amino acid sequence is derived from a human antibody. Specific examples thereof include amino acid sequences of the FR of the VH and the VL of a human antibody registered in the database such as Protein Data Bank and common amino acid sequences of each sub group of the FR of the VH and the VL of a human antibody (Sequences of Proteins of Immunological Interest, US Dept. Health and Human Services, 1991) may be exemplified.

The antibody of the present invention include antibodies comprising these amino acid sequences in which one or more amino acids are deleted, added, substituted, or inserted and which specifically binds to human CRTH2 and has the same function in the biological activity such as cytotoxic activity; and the antibody fragments.

The antibody of the present invention includes an antibody bonded to monkey CRTH2. Examples of the monkey CRTH2 include marmoset CRTH2, cynomolgus monkey CRTH2, and rhesus monkey CRTH2. Among these, cynomolgus monkey CRTH2 is preferable.

The antibody of the present invention include Fc fusion protein in which Fc and an antibody fragment are bound to each other, Fc fusion protein in which Fc and a naturally-occurring ligand or a receptor are bound to each other (also referred to as immunoadhesion), and Fc fusion protein in which a plurality of Fc regions are fused. Further, modified Fc regions including amino acid residue modification in which amino acid residue substitution is carried out for stabilizing an antibody or for controlling half-life in blood can be used for the antibodies of the present invention.

In the present invention, the antibody fragment is a fragment which comprises an antigen-binding domain which recognizes at least one of 192th glycine and 194th aspartic acid in the amino acid sequence of human CRTH2 represented by SEQ ID NO: 2, and binds thereto, and has antigen-binding activity. Examples of the antibody fragment of the present invention include Fab, Fab', $F(ab')_2$, single chain Fv (hereinafter, also referred to as scFv), diabody, dsFv, and peptides comprising a plurality of CDRs.

Fab is an antibody fragment with a molecular weight of approximately 50000 in which the approximately half of an H chain on an N terminal side and the entire L chain are bonded to each other with a disulfide bond and which has antigen-binding activity, among fragments obtained by treating IgG with a protease papain (cleaving at the 224th amino acid residue of the H chain).

The Fab of the present invention can be obtained by treating the antibody of the present invention which specifically binds to human CRTH2 with a protease papain. Alternatively, the Fab can be produced by inserting DNA-encoding Fab of the antibody into an expression vector for prokaryote or an expression vector for eukaryote and introducing the vector into a prokaryote or a eukaryote.

$F(ab')_2$ is an antibody fragment with a molecular weight of approximately 100000 which is slightly larger than Fab fragments bonded to each other through a disulfide bond of the hinge region and has antigen-binding activity, among fragments obtained by treating IgG with a protease pepsin (cleaving at the 234th amino acid residue of the H chain is cut).

The $F(ab')_2$ of the present invention can be obtained by treating the antibody of the present invention which specifically binds to human CRTH2 with a protease pepsin. Alternatively, the $F(ab')_2$ can be produced by bonding the following Fab' through a thioether bond or a disulfide bond.

Fab' is an antibody fragment which is obtained by cutting the disulfide bond of the hinge region of the $F(ab')_2$ and has antigen-binding activity with a molecular weight of approximately 50000.

The Fab' of the present invention can be obtained by treating the $F(ab')_2$ composition which specifically binds to human CRTH2 of the present invention with a reductant dithiothreitol. Alternatively, the Fab' can be produced by inserting DNA encoding Fab' fragment of the antibody into an expression vector for prokaryote or an expression vector for eukaryote and introducing the vector into a prokaryote or a eukaryote to express the Fab'.

scFv is an antibody fragment having antigen-binding activity, which is a VH-P-VL or VL-P-VH polypeptide in which one VH and one VL are linked to each other using an appropriate peptide linker (P) such as a linker peptide obtained by connecting an arbitrary number of linkers formed of four Glys and one Ser residue (G4S).

scFv of the present invention can be produced by obtaining cDNA that encodes the VH and the VL of the antibody of the present invention which specifically binds to human CRTH2, constructing DNA which encodes scFv, inserting the DNA into an expression vector for prokaryote or an expression vector for eukaryote and introducing the vector into a prokaryote or a eukaryote to express the scFv.

A diabody is an antibody fragment in which scFv is dimerized and which has divalent antigen-binding activity. The divalent antigen-binding activity may be the same as each other or may be made to be different from each other.

The diabody of the present invention can be produced by obtaining cDNA that encodes the VH and the VL of an antibody of the present invention which specifically binds to human CRTH2, forming DNA encoding scFv such that the length of the amino acid sequence of P becomes 8 residues or less, inserting the DNA into an expression vector for prokaryote or an expression vector for eukaryote and introducing the vector into a prokaryote or a eukaryote.

dsFv is obtained by binding polypeptides in which one amino acid residue in each VH and VL is substituted with a cysteine residue through a disulfide bond between the cysteine residues. The amino acid residue to be substituted with a cysteine residue can be selected based on the three-dimensional structure prediction of an antibody according to a method shown by Reiter et al. (Protein Engineering, 7, 697, 704, 1994).

The dsFv of the present invention can be produced by obtaining cDNA that encodes the VH and the VL of the antibody of the present invention which specifically binds to human CRTH2, constructing DNA encoding dsFv, inserting the DNA into an expression vector for prokaryote or an expression vector for eukaryote and introducing the expression vector into a prokaryote or a eukaryote to express the dsFv.

The peptide comprising CDR is formed to include at least one region of the CDR of VH or VL. The peptide including a plurality of CDRs can be bound to each other directly or through an appropriate peptide linker.

The peptide comprising CDR of the present invention can be produced by constructing DNA encoding CDR of VH and VL of the antibody of the present invention which specifically bound to human CRTH2, inserting the DNA into an expression vector for prokaryote or a expression vector for eukaryote, and introducing the expression vector into a prokaryote or a eukaryote to express the peptide comprising CDR.

Moreover, a peptide comprising CDR can be produced by a chemical synthesis method such as a Fmoc method (fluorenylmethyloxycarbonyl method) or a tBoc method (t-butyloxycarbonyl method).

The antibody or the antibody fragment thereof of the present invention includes a monoclonal antibody or the antibody fragment thereof in which one or more amino acids comprising an amino acid sequence constituting the above-described antibody or the antibody fragment thereof are deleted, substituted, inserted, or added and has the same activity as that of the above-described antibody or the antibody fragment thereof. The number of amino acids to be deleted, substituted, inserted, or added is not particularly limited as long as the number is 1 or greater, but is almost the number of amino acids which can be deleted, substituted, or added by a known technique such as site-specific mutagenesis described in Molecular Cloning, Second Edition, Current Protocols in Molecular Biology, Nucleic Acids Research, 10, 6487 (1982), Proc. Natl. Acad. Sci., USA, 79, 6409 (1982), Gene, 34, 315 (1985), Nucleic Acids Research, 13, 4431 (1985), and Proc. Natl. Acad. Sci. USA, 82, 488 (1985). The number of amino acids may be 1 to several tens, preferably 1 to 20, more preferably 1 to 10, and still more preferably 1 to 5.

The expression of "one or more amino acid residues are deleted, substituted, inserted, or deleted in the amino acid sequence of human CRTH2 or the antibody of the present invention" means that one or a plurality of amino acid residues are deleted, substituted, inserted or added at optional positions in one or a plurality of amino acid sequences in the same sequence. The deletion, substitution, insertion, or addition may occur simultaneously and amino acid residues to be substituted, inserted, or added may be natural type or non-natural type residues.

Examples of natural type amino acid residue include L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, and L-cysteine.

Preferred examples of the amino acid residues which can be substituted with each other are as follows. Amino acid residues included in the same group can be substituted with each other.

A group: leucine, isoleucine, norleucine, valine, norvaline, alanine, 2-aminobutanoic acid, methionine, O-methylserine, t-butylglycine, t-butylalanine, and cyclohexylalanine;

B group: aspartic acid, glutamic acid, isoaspartic acid, isoglutamic acid, 2-aminoadipic acid, and 2-aminosuberic acid;

C group: asparagine and glutamine;

D group: lysine, arginine, ornithine, 2,4-diaminobutanoic acid, and 2,3-diaminopropionic acid;

E group: proline, 3-hydroxy proline, and 4-hydroxy proline;

F group: serine, threonine, and homoserine; and

G group: phenylalanine and tyrosine.

The transformant of the present invention is not particularly limited as long as the transformant which is obtained by introducing DNA encoding an antibody molecule which specifically binds to human CRTH2 into a host cell and produces the antibody of the present invention. Specific examples thereof include transformants obtained by introducing DNA encoding antibody molecules which specifically binds to human CRTH2 into host cells such as the following (a) to (i).

(a) Chinese hamster ovary tissue-derived CHO cells;
(b) rat myeloma cell line YB2/3HL. P2. G11. 16Ag. 20 cells;
(c) mouse myeloma cell line NS0 cells;
(d) mouse myeloma cell line SP2/0-Ag14 cells;
(e) Syrian hamster kidney tissue-derived BHK cells;
(f) hybridoma cells producing an antibody;
(g) human leukemia cell line Namalwa cells;
(h) embryonic stem cells; and
(i) amphicytula.

Further, preferred examples of the transformant of the present invention that produces an antibody in which a N-glycoside-linked sugar chain binds to an Fc region of the antibody and fucose is not bonded to a N-acetyl glucosamine of a reducing terminal of the N-glycoside-linked sugar chain include a transformant obtained by introducing DNA encoding an antibody molecule which specifically binds to human CRTH2 into a host cell in which glycosyltransferase is decreased or deficient which is produced by a method described in Pamphlet of International Publication No. 2005/035586 and Pamphlet of International Publication No. 02/31140.

A method of producing the antibody or the antibody fragment thereof of the present invention is not particularly limited as long as the method is for culturing a transformant that produces the antibody or the antibody fragment thereof of the present invention, and preferred examples thereof include a method of producing an antibody or the antibody fragment thereof by culturing a transformant that produces the antibody or the antibody fragment thereof of the present invention, secreting and accumulating the antibody or the antibody fragment thereof in a culture, and collecting and purifying the antibody or the antibody fragment thereof.

The antibody or the antibody fragment thereof produced by the above-described production method is also exemplified as the antibody or the antibody fragment thereof of the present invention.

The composition of the present invention is not particularly limited as long as the composition comprises the antibody or the antibody fragment thereof of the present invention, and examples thereof include a composition comprising antibody molecule in which single type of sugar chain binds thereto and a composition comprising antibody molecules comprising a plurality of sugar chain structures. Further, a composition comprising an appropriate additive and a buffer may be used. Preferred examples of the composition of the present invention include medicine and diagnostic agents comprising the antibody or the antibody fragment thereof of the present invention as an active ingredient.

The medicine or the diagnostic agent of the present invention is not particularly limited as long as the medicine or the diagnostic agent contains the antibody or the antibody fragment thereof of the present invention as active ingredients. Preferred examples thereof include medicine or diagnostic agent for diseases associated with human CRTH2-expressing cells.

The treatment method of the present invention is not particularly limited as long as the method is a treatment method of administering an effective amount of antibody or antibody fragment thereof of the present invention, and preferred examples thereof include a method of treating diseases associated with human CRTH2-expressing cells.

The use of the antibody or the antibody fragment thereof of the present invention is not particularly limited as long as the antibody or the antibody fragment thereof of the present invention is used for producing a therapeutic agent for a disease associated with human CRTH2-expressing cells. Further, the antibody or the antibody fragment thereof of the present invention can be used for at least one of treatment and prevention of a disorder or a disease associated with human CRTH2-expressing cells.

The disorder or the disease associated with human CRTH2-expressing cells is not particularly limited, and examples thereof include an allergic disease, an autoimmune disease, a disease accompanied by at least one of increase and hyperergasia of eosinophils, and a disease accompanied by at least one of increase and hyperergasia of Th2 cells and a disease accompanied by at least one of increase and hyperergasia of ILC2.

Specific examples thereof include allergic or non-allergic rhinitis, chronic sinusitis or rhinitis, nasal polyp, chronic sinusitis accompanied by nasal polyp, eosinophilic sinusitis, acute sinusitis, asthma, childhood asthma, allergic bronchitis, alveolitis, farmer's disease, hypersensitivity respiratory tract, infections, for example, allergic conjunctivitis caused by bacteria, virus, worms, fungi, protozoa, and other pathogens, bronchitis or pneumonitis, bronchiectasis, adult respiratory distress syndrome, bronchus and lung edema, bronchitis, pneumonitis, or interstitial pneumonitis caused by various sources such as poison gas and suction or inhalation of vapor, bronchitis, pneumonitis, or interstitial pneumonitis caused by heart failure, X-ray, radiation, or chemotherapy, bronchitis, pneumonitis, or interstitial pneumonitis associated with collagen disease, for example, erythematosus or generalized scleroderma, pulmonary fibrosis, idiopathic pulmonary fibrosis (IPF), interstitial lung disease or interstitial pneumonitis of various origins, for example, asbestosis, silicosis, m. Boeck, or sarcoidosis, granulomatous disease, cystic fibrosis, mucoviscidosis, α1-antitrypsin deficiency, eosinophilic cellulite (for example, Well syndrome), eosinophilic pneumonia (for example, Loeffler syndrome or chronic eosinophilic pneumonia), eosinophilic fasciitis (for example, Shulman syndrome), eosinophilic esophagitis, eosinophils increased syndrome, delayed-type hypersensitivity, non-allergic asthma, exercise-induced bronchoconstriction; chronic obstructive pulmonary disease (COPD), acute bronchitis, chronic bronchitis, emphysema, systemic anaphylaxis, hypersensitivity reaction, drug allergy (for example, with respect to penicillin or cephalosporin), eosinophilia myalgia syndrome caused by ingestion of pollution tryptophan, insect sting allergy; autoimmune disease, for example, rheumatoid arthritis, psoriatic arthritis, multiple sclerosis, systemic lupus erythematosus, myasthenia gravis, immune thrombocytopenia (adult ITP, neonatal thrombocytopenia, pediatric ITP), immune hemolytic anemia (autoimmune and drug-induced), Evans syndrome (platelet and red blood cell immune cytopenia), Rh disease of a newborn, Goodpasture syndrome (anti-GBM disease), celiac disease (Celiac), autoimmune cardiomyopathy, juvenile-onset diabetes; glomerulonephritis, autoimmune thyroiditis, Behcet's disease, graft rejection (for example, in transplantation), for example, homograft rejection or graft-versus-host disease; inflammatory bowel disease, for example, Crohn's disease or ulcerative colitis; spondyloarthropathy; scleroderma; psoriasis (including T-cell mediated psoriasis) and inflammatory skin disease, for example, dermatitis, eczema, atopic dermatitis, allergic contact dermatitis, urticaria (for example, chronic idiopathic, chronic spontaneity, or physical urticaria), bullous pemphigoid; vasculitis (for example, necrotic, cutaneous, granulomatous and hypersensitive angiitis, eosinophilic polyneuropathy vasculitis granulomatous disease); erythema nodosum; eosinophilic myositis, eosinophilic fasciitis, and inflammatory or allergic diseases and conditions including cancer with leukocyte infiltration of the skin or organ.

Preferred examples of the disorder or the disease associated with human CRTH2-expressing cells include asthma, childhood asthma, chronic obstructive pulmonary disease, atopic dermatitis, allergic rhinitis, and acute or chronic sinusitis.

The medicine containing the antibody or the antibody fragment thereof of the present invention or a derivative of these may include only the antibody or the antibody fragment thereof or a derivative of these as an effective component, but is typically provided as a medicinal formulation produced by being mixed with one or more carriers pharmacologically acceptable according to a known method in the technical field of pharmaceutics.

Examples of administration routes include oral administration and parenteral administration such as oral cavity administration, tracheobronchial administration, rectally administration, subcutaneous administration, intramuscular administration, intravenous administration, or intraperitoneal administration. Examples of administration forms include sprays, capsules, tablets, powders, granules, syrups, emulsions, suppositories, injections, ointments, and tapes.

Examples of the formulation suitable for oral administration include emulsions, syrups, capsules, tablets, powders, and granules.

The antibody of the present invention include a derivative of an antibody in which a radioisotope, a small molecule drug, a macromolecule drug, protein, or nucleic acid binds to the antibody or the antibody fragment thereof of the present invention chemically or in a genetic engineering manner.

In a case where a derivative of an antibody is used as a treatment method, a prophylaxis method, therapeutic agent or therapeutic agent, examples of the drug bound to the antibody or the antibody fragment thereof of the present invention include a chemotherapeutic agent, an antibody drug, an immunostimulant, and a macromolecule drug. Examples of protein include cytokine, growth factors, and toxic protein. Examples of nucleic acid include decoy, antisense, siRNA, and miRNA.

In a case where a derivative of an antibody is used for a detection method, a quantification method, a reagent for detection, or a reagent for quantification, examples of the drug bound to the antibody or the antibody fragment thereof of the present invention include a marker used for a typical immunological detection method or immunological measurement method.

In the present invention, a derivative of an antibody can be produced by bonding a radioisotope, a small molecule drug, a macromolecule drug or protein to the N terminal side or the C terminal side of an H chain or an L chain of the antibody or the antibody fragment thereof, an appropriate substituent or a side chain in the antibody or the antibody fragment thereof, or a sugar chain of the antibody or the antibody fragment thereof of the present invention, by a chemical method [methods described in Antibody Engineering Introduction, Chijin Shokan (1994) or the like].

In the present invention, a derivative of an antibody can be produced by a genetic engineering method wherein DNA encoding the antibody or the antibody fragment thereof of the present invention is connected with DNA encoding protein intended to be connected, the DNA is inserted into an expression vector, and the expression vector is introduced into an appropriate host cell to express the derivative.

Examples of the radioisotope include $^{131}$I, $^{125}$I, $^{90}$Y, $^{64}$Cu, $^{99}$Tc, $^{77}$Lu, and $^{211}$At. The radioisotope can be directly bonded to an antibody by a chloramine-T method or the like. Further, a substance that chelates the radioisotope may be bonded to an antibody. Examples of the chelating agent include 1-isothiocyanatobenzyl-3-methyldiethylenetriamine pentaacetate (MX-DTPA).

Examples of the small molecule drug include alight emitting substance such as acridinium ester or lophine and a fluorescent substance such as fluorescein isothiocyanate (FITC) or tetramethyl rhodamine isothiocyanate (RITC).

Examples of the method of bonding a small molecule drug to an antibody include a method of bonding a chemical agent to an amino group of an antibody using glutaraldehyde and a method of bonding an amino group of a chemical agent to a carboxyl group of an antibody using water-soluble carbodiimide.

Examples of the macromolecule drug include polyethylene glycol (hereinafter, referred to as PEG), albumin, dextran, polyoxyethylene, a styrene-maleic acid copolymer, polyvinylpyrrolidone, a pyran copolymer, and hydroxypropyl methacrylamide.

The immunological detection method or the immunological measurement method is a method of detecting or measuring the amount of antibody or the amount of antigen using the antigen or antibody which is labeled. Examples of the immunological detection method or the immunological measurement method include a radioactive substance-labeled immunoantibody assay (RIA) method, an enzyme immunoassay (EIA or ELISA) method, a fluorescent immunoassay (FIA) method, a luminescent immunoassay method, a western blotting method, and a physico-chemical method.

Diseases associated with human CRTH2 can be diagnosed by detecting or measuring human CRTH2-expressing cells according to the above-described method using the antibody or the antibody fragment thereof of the present invention.

A biological sample which is a subject for detecting or measuring human CRTH2 of the present invention is not particularly limited as long as the sample may include human CRTH2 or a peptide fragment having a part thereof secreted out of cells, or human CRTH2-expressing cells, such as tissue cells, blood, plasma, serum, pancreatic juice, urine, feces, tissue fluid, bronchioalveolar lavage, or a culture solution.

The diagnostic agent containing the antibody or the antibody fragment thereof of the present invention or a derivative of these may include a reagent for carrying out an antigen-antibody reaction or a reagent for detecting the reaction according to a diagnostic method. Examples of the reagent for carrying out an antigen-antibody reaction include a buffering agent and salts. Examples of the reagent for detecting the reaction include reagents used for a typical immunological detection method or immunological measurement method, such as a secondary antibody labeled which recognizes the antibody, the antibody fragment thereof or a derivative of these, or a substrate corresponding to the label.

Hereinafter, a method of producing the antibody of the present invention, a method of treating a disease, and a method of diagnosing a disease will be described in detail.

1. Method of Producing Antibody (1) Preparation of Antigen

Human CRTH2 as an antigen or cells expressing human CRTH2 can be obtained by introducing an expression vector comprising cDNA that encodes the full length or the partial length of human CRTH2 into *E. coli*, yeast, insect cells, or animal cells.

Further, the antigen can be also obtained by purifying human CRTH2 from various human cultured cells or human tissues or the like which express a large amount of human CRTH2. Moreover, the cultured cells or the tissues can be used as an antigen as they are. Further, a synthetic peptide comprising a partial sequence of human CRTH2 is prepared by a chemical synthetic method such as an Fmoc method or a tBoc method and then can be used as an antigen.

A known tag such as FLAG or His may be added to the C terminal or the N terminal of the synthetic peptide comprising human CRTH2 or a partial sequence of human CRTH2.

The human CRTH2 used in the present invention can be produced by expressing DNA encoding the human CRTH2 in a host cell using a method described in Molecular Cloning, A Laboratory Manual, Second Edition, Cold Spring Harbor Laboratory Press (1989) or Current Protocols in Molecular Biology, John Wiley & Sons (1987 to 1997), for example, the following method.

First, a recombinant vector is prepared by inserting full-length cDNA comprising a part that encodes human CRTH2 into the downstream of a promotor of an appropriate expression vector. A DNA with suitable length fragment which is prepared based on the full-length cDNA, has a part that encodes a polypeptide may be used in place of the above described full-length cDNA. Next, a transformant that produces the polypeptide can be obtained by introducing the recombinant vector to be obtained into a host cell suitable for the expression vector.

The expression vector is not particularly limited as long as the expression vector can be autonomously replicated or integrated into a chromosome in a host cell being used and includes a suitable promotor at a position where DNA encoding a polypeptide can be transcribed.

The host cell is not particularly limited as long as the host cell can express a target gene and the example there of is a microorganism belonging to the genus *Escherichia* such as *E. coli*, yeast, insect cells, or animal cells.

In a case where a prokaryote such as *E. coli* is used as a host cell, it is preferable that the recombinant vector enables autonomous replication in a prokaryote and includes a promotor, a ribosome-binding sequence, DNA comprising a part that encodes human CRTH2, and a transcription termination sequence.

Moreover, the recombinant vector does not necessarily have a transcription termination sequence, but it is preferable that a transcription termination sequence is arranged immediately right after a structural gene. Further, the recombinant vector may include genes controlling a promotor.

As the recombinant vector, it is preferable to use a plasmid in which the distance between a Shine-Dalgarno sequence (also referred to as an SD sequence) which is a ribosome-binding sequence and initiation codon is appropriately adjusted (for example, 6 to 18 bases).

Moreover, in a base sequence of DNA encoding the human CRTH2, a base can be substituted so as to be a codon optimal for expression in a host and thus the production rate of desired human CRTH2 can be improved.

The expression vector is not particularly limited as long as the expression vector is capable of exhibiting the function in a host cell being used, and examples thereof include pBTrp2, pBTac1, pBTac2 (all Roche Diagnostics K.K.), pKK233-2 (Pharmacia Corp.), pSE280 (Invitrogen), pGEMEX-1 (Promega Corporation), pQE-8 (QIAGEN), pKYP10 (JP-A-558-110600), pKYP200 [Agricultural Biological Chemistry, 48, 669(1984)], pLSA1 [Agric Biol. Chem., 53, 277 (1989)], pGEL1 [Proc. Natl. Acad. Sci. USA, 82, 4306 (1985)], pBluescript II SK (−) (Stratagene), pTrs30 [prepared from *E. coli* JM109/pTrS30 (FERM BP-5407)], pTrs32 [prepared from *E. coli* JM109/pTrS32 (FERM BP-5408)], pGHA2 [prepared from *E. coli* IGHA2 (FERM BP-400), JP-A-560-221091], pGKA2 [prepared from *E. coli* IGKA2 (FERM BP6798), JP-A-560-221091], pTerm2 (U.S. Pat. No. 4,686,191, U.S. Pat. No. 4,939,094, and U.S. Pat. No. 5,160,735), pSupex, pUB110, pTP5, pC194, pEG400 [J. Bacteriol., 172, 2392 (1990)], pGEX (Pharmacia Corp.), pET system (Novagen), and pME18SFL3.

The promotor is not particularly limited as long as the promotor can exhibit the function in a host cell being used. Examples thereof include promotors derived from *E. coli* or phage such as a trp promoter (Ptrp), a lac promoter, a PL promoter, a PR promoter, and a T7 promoter. Further, promotors whose designs are artificially changed, such as a tandem promoter in which two Ptrps are serially arranged, a tac promoter, a lacT7 promoter, and a letI promoter can be used.

Examples of the host cell include *E. coli* XL-1Blue, *E. coli* XL2-Blue, *E. coli* DH1, *E. coli* MC1000, *E. coli* KY3276, *E. coli* W1485, *E. coli* JM109, *E. coli* HB101, *E. coli* No. 49, *E. coli* W3110, *E. coli* NY49, and *E. coli* DH5α.

The method of introducing a recombinant vector into a host cell is not particularly limited as long as the method is for introducing DNA into a host cell being used, and examples thereof include a method of using calcium ions [Proc. Natl. Acad. Sci. USA, 69, 2110 (1972); Gene, 17, 107 (1982); Molecular & General Genetics, 168, 111 (1979)].

In a case where animal cells are used as host cells, the expression vector is not particularly limited as long as the vector can exhibit the function in animal cells and examples thereof include pcDNA I, pcDM8 (Funakoshi Co., Ltd.), pAGE107 [JP-A-H03-22979; Cytotechnology, 3, 133 (1990)], pAS3-3 (JP-A-H02-227075), pcDM8 [Nature, 329, 840 (1987)], pcDNA I/Amp (Invitrogen), pcDNA 3.1 (Invitrogen), pREP4 (Invitrogen), pAGE103 [J. Biochemistry, 101, 1307 (1987)], pAGE210, pME18SFL3, pKANTEX93 (Pamphlet of International Publication No. 97/10354), N5KG1val (U.S. Pat. No. 6,001,358), INPEP4 (Biogen-IDEC), and a transposon vector (Pamphlet of International Publication No. 2010/143698).

The promotor is not particularly limited as long as the promotor can exhibit the function in animal cells, and examples thereof include a promotor of immediate early (IE) genes of cytomegalovirus (CMV), an early promotor of SV40, a promotor of retrovirus, a metallothionein promotor, a heat shock promotor, an SRα promotor, and a promotor or an enhancer of Moloney mouse leukemia virus. Further, an enhancer of IE genes of human CMV may be used with a promotor.

Examples of host cells include human leukemia cell Namalwa cells, monkey cell COS cells, Chinese hamster ovary cell CHO cells [Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci. USA, 60, 1275 (1968); Cell, 6, 121 (1975); Molecular Cell Genetics, Appendix I, II (pp. 883 to 900)]], CHO/DG44, CHO-K1 (ATCC No: CCL-61), DUkXB11 (ATCC No: CCL-9096), Pro-5 (ATCC No: CCL-1781), CHO-S (Life Technologies, Cat #11619), Pro-3, rat myeloma cells YB2/3HL. P2. G11. 16Ag. 20 (or referred to as YB2/0), mouse myeloma cells NS0, mouse myeloma cells SP2/0-Ag14, and Syrian hamster cells BHK or HBT5637 (JP-A-S63-000299).

The method of introducing a recombinant vector into a host cell is not particularly limited as long as the method is for introducing DNA into an animal cell, and examples thereof include an electroporation method [Cytotechnology, 3, 133 (1990)], a calcium phosphate method (JP-A-H02-227075)), and a lipofection method [Proc. Natl. Acad. Sci. USA, 84, 7413 (1987)].

Human CRTH2 can be produced by culturing a transformant derived from a microorganism or an animal cell that includes a recombinant vector in which DNA encoding human CRTH2 is integrated obtained in the above-described manner in a culture medium, secreting and accumulating the human CRTH2 in a culture, and collecting the human CRTH2 from the culture. The method of culturing the transformant in a culture medium can be carried out according to a typical method used for culturing a host.

In a case where cells derived from a eukaryote are used for expression, human CRTH2 to which sugar or a sugar chain is added can be obtained.

When a microorganism transformed by a recombinant vector using an inductive promotor is cultured, an inducer may be added to a culture medium if necessary. For example, isopropyl-β-D-thiogalactopyranoside may be added to a culture medium in which a microorganism transformed by a recombinant vector using a lac promotor is cultured and indole acrylic acid may be added to a culture medium in which a microorganism transformed by a recombinant vector using a trp promotor is cultured.

Examples of the culture medium for culturing a transformant obtained from animal cells as a host include generally used RPMI1640 culture medium [The Journal of the American Medical Association, 199, 519 (1967)], an Eagle's MEM culture medium [Science, 122, 501 (1952)], Dubecco's modified MEM culture medium [Virology, 8, 396 (1959)], 199 culture medium [Proc. Soc. Exp. Biol. Med., 73, 1 (1950)], Iscove's Modified Dulbecco's medium (IMDM) culture medium, and culture media obtained by adding fetal bovine serum (FBS) or the like to these culture media. The culturing is usually carried out under the conditions of pH of 6 to 8 at 30° C. to 40° C. for 1 to 7 days in the presence of 5% $CO_2$. Further, antibiotics such as' kanamycin or penicillin may be added to a culture medium during the culturing if necessary.

As a method of expressing genes encoding human CRTH2, a method of secretory production or fusion protein expression [Molecular Cloning, A Laboratory Manual, Second Edition, Cold Spring Harbor Laboratory Press (1989)] can be used in addition to direct expression.

Examples of the method of producing human CRTH2 include a method of producing human CRTH2 in a host cell, a method of secreting human CRTH2 out of a host cell, and a method of producing human CRTH2 on an outer membrane of a host cell, and an appropriate method can be selected by changing the host cell being used or the structure of human CRTH2 to be produced.

In a case where human CRTH2 is produced in a host cell or on an outer membrane of a host cell, human CRTH2 can be actively secreted outside the host cell using a method of Paulson et al. [J. Biol. Chem., 264, 17619 (1989)], a method of Lowe et al. [Proc. Natl. Acad. Sci. USA, 86, 8227 (1989); Genes Develop., 4, 1288 (1990)], and methods described in JP-A-H05-336963) and Pamphlet of International Publication No. 94/23021.

In addition, the amount of producing human CRTH2 can be increased with a gene amplification system (JP-A-H02-227075) using dihydroforate reductase genes.

The human CRTH2 to be obtained can be isolated or purified in the following manner for example. In a case where human CRTH2 in cells is expressed as a soluble protein, cells are recovered by centrifugation after culturing and disrupted using an ultrasonic crusher, a French press, a Manton Gaulin homogenizer, or a dynomill after suspension in an aqueous buffer, thereby obtaining a cell-free extract.

A purified preparation can be obtained from a supernatant obtained by centrifugation of the cell-free extract is centrifuged, using a typical method of isolating and purifying protein, that is, a solvent extraction method, a salting-out method using ammonium sulfate and the like, a desalting method, a precipitation method using an organic solvent, anion exchange chromatography using a resin such as diethylaminoethyl (DEAE)-Sepharose or DIAION HPA-75 (Mitsubishi Chemical Corporation), cation exchange chromatography using a resin such as S-Sepharose FF (Pharmacia Corp.), hydrophobic chromatography using a resin such as butyl Sepharose or phenyl Sepharose, gel filtration using a molecular sieve, affinity chromatography, a chromatofocusing method, or an electrophoresis method such as isoelectric point electrophoresis. These methods may be used alone or in combination.

In a case where human CRTH2 is expressed as an insoluble matter in cells, the insoluble matter of the human CRTH2 are recovered as a precipitate fraction by disrupting the cells in the above-described manner after recovering and performing centrifugation. The recovered insoluble matter of the human CRTH2 is solubilized by a protein denaturing agent. A purified preparation of a polypeptide can be obtained by diluting or dialyzing the solubilized solution after the human CRTH2 is restored to have a normal three-dimensional structure using the same isolation and purification method as described above.

In a case where human CRTH2 or the derivative thereof such as glycosylated product is secreted outside the cells, the derivative of human CRTH2 or a sugar modification can be recovered from a culture supernatant. A soluble fraction is obtained by treating the culture through a method of centrifugation or the like in the same manner as described above and the same isolation and purification method as described above is used, thereby obtaining a purified preparation from the soluble fraction.

Human CRTH2 used in the present invention can be produced by a chemical synthesis method such as an Fmoc method or a tBoc method. Further, human CRTH2 can be chemically synthesized using a peptide synthesizer of Advanced Chem Tech, PerkinElmer Inc., Pharmacia Corp., Protein Technology Instruments, Synthecell-Vega Corp., Perceptive Inc., Shimadzu Corporation or the like.

(2) Immunization of Animal and Preparation of Antibody-Producing Cells for Fusion An animal such as a mouse, rat, or hamster which is 3- to 20-week-old is immunized with the antigen obtained in (1) described above and antibody-producing cells in the spleen, the lymph node, and the peripheral blood of the animal is collected. Further, in a case where immunogenicity is low and the antibody titer is not sufficiently increased in the animal, human CRTH2 knockout mouse can be used as an animal to be immunized.

An animal is immunized by subcutaneous administration, tail administration, intravenous administration, or intraperitoneal administration of an antigen together with an appropriate adjuvant such as Freund's complete adjuvant or aluminum hydroxide gel or pertussis vaccine. In a case where the antigen is a partial peptide, conjugate are prepared with carrier protein such as bovine serum albumin (BSA) or keyhole limpet hemocyanin (KLH) and these are used immunogens.

An antigen is administered 1 to 10 times at one- to two-week interval after first administration. The blood is collected from venous plexus of eye fundus or tail vein at the third to seventh day after each administration and the antibody titer of the serum is measured using an enzyme immunoassay method [Antibodies—A Laboratory Manual, Cold Spring Harbor Laboratory (1988)] or the like. An animal whose serum shows sufficient antibody titer with respect to an antigen used for immunization is used as a supply source of antibody-producing cells for fusion.

At the third to seventh day after final administration of an antigen, tissues including antibody-producing cells of the immunized animal, such as the spleen or the like, are resected and antibody-producing cells are collected. In a case of using spleen cells, the spleen is cut, loosened, and centrifuged and red blood cells are removed, thereby obtaining antibody-producing cells for fusion.

(3) Preparation of Myeloma Cells

As myeloma cells, established cells obtained from a mouse, for example, 8-azaguanine-resistant mouse (BALB/c-derived) myeloma cell line P3-X63Ag8-U1 (P3-U1) [Current Topics in Microbiology and Immunology, 18, 1 (1978)], P3-NS1/1Ag41 (NS-1) [European J. Immunology, 6, 511 (1976)], SP2/0-Ag14 (SP-2)[Nature, 276, 269 (1978)], P3-X63-Ag8653 (653) [J. Immunology, 123, 1548 (1979)], or P3-X63-Ag8 (X63) [Nature, 256, 495 (1975)] are used.

The myeloma cells are subcultured in a normal culture medium [RPMI1640 culture medium to which glutamine, 2-mercaptoethanol, gentamicin, FBS, and 8-azaguanine are added] and subcultured in a normal culture medium before 3 to 4 days of cell fusion to ensure $2 \times 10^7$ or more cells on the day of fusion.

(4) Cell Fusion and Preparation of Monoclonal Antibody-Producing Hybridomas

The antibody-producing cells for fusion obtained in (2) described above and the myeloma cells obtained in (3) described above are washed with a minimum essential medium (MEM) culture medium or PBS (1.83 g of disodium phosphate, 0.21 g of monopotassium phosphate, 7.65 g of salt, 1 L of distilled water, pH of 7.2) mixed with each other so as to yield the ratio of the cell number of antibody-producing cells for fusion:myeloma cells=5:1 to 10:1, and the supernatant is removed after centrifugation.

After the precipitated cell group is sufficiently loosened, a mixed solution of polyethylene glycol-1000 (PEG-1000), MEM culture medium, and dimethyl sulfoxide is added while being stirred at 37° C. Further, 1 to 2 mL of the MEM culture medium is added several times at 1- to 2-minute interval, and then MEM culture medium is added to yield a total amount of 50 mL. After centrifugation, the supernatant is removed.

After the precipitated cell group is gently loosened, antibody-producing cells for fusion are gently suspended in HAT culture medium [normal culture medium to which hypoxanthine, thymidine, and aminopterin are added]. The suspension is cultured in a 5% $CO_2$ incubator at 37° C. for 7 to 14 days.

A part of the culture supernatant is sampled after culturing, a cell group which reacts with an antigen including human CRTH2 and does not react with an antigen that does not include human CRTH2 is selected according to a method of selecting hybridomas, such as reactivity analysis against human CRTH2-expressing cells described below. Next, cloning is repeated twice by a limiting dilution method [an HT culture medium (culture medium obtained by removing aminopterin from an HAT culture medium) is used for the first cloning and a normal culture medium is used for the second cloning] and then hybridomas recognized to stably have strong antibody titer are selected as monoclonal antibody-producing hybridomas.

(5) Preparation of Purified Monoclonal Antibody

The monoclonal antibody-producing hybridomas obtained in (4) described above are intraperitoneally injected to a Pristine-treated [0.5 mL of 2,6,10,14-tetramethylpentadecane (Pristane) is intraperitoneally administered and the animal is bred for 2 weeks] 8- to 10-week-old mouse or nude mouse. The hybridomas develop ascites cancer after 10 to 21 days. After the ascites fluid is collected from the mouse and the solid content is removed by centrifugation, the fluid is subject to salting out with 40 to 50% ammonium sulfate, purification is carried out using a caprylic acid precipitation method, a DEAE-sepharose column, a protein A-column, or a gel filtration column, and then IgG fractions or IgM fractions are collected to obtain a purified monoclonal antibody.

Furthermore, after the monoclonal antibody-producing hybridomas obtained in (4) described above are cultured in an RPMI1640 culture medium to which 10% FBS is added, the supernatant is removed by centrifugation, suspended in a Hybridoma-SFM culture medium, and cultured for 3 to 7 days. The obtained cell suspension is centrifuged, the obtained supernatant is purified using a protein A-column or a protein G-column, and IgG fractions are collected, thereby obtaining a purified monoclonal antibody. Further, 5% Daigo's GF21 can be added to the Hybridoma-SFM culture medium.

The subclass of the antibody is determined by an enzyme immunoassay method using a subclass typing kit. The amount of protein is calculated by a Lowry method or using absorbance at 280 nm.

(6) Selection of Monoclonal Antibody

A monoclonal antibody is selected by analyzing the reactivity against human CRTH2-expressing cells using flow cytometry as described below.

Examples of the human CRTH2-expressing cells include transgenic cells obtained by introducing an expression vector comprising cDNA encoding human CRTH2 obtained in (1) described above into animal cells or the like, human eosinophils, basophils, Th2, ILC2, nonclassical monocyte, and Th2/Th17 cells.

After the cells are dispensed to a plate such as a 96 well plate, the substance to be tested such as the serum, a culture supernatant of hybridomas, or a purified monoclonal antibody as a first antibody is dispensed for reaction. The cells after the reaction are washed with PBS including 1% to 10% of bovine serum albumin (BSA) (hereinafter, referred to as BSA-PBS) or the like, and then an anti-immunoglobulin antibody labeled with a fluorescent reagent as a second antibody is dispensed for reaction. After the cells are washed with BSA-PBS or the like, a monoclonal antibody specifically reacting against expressing cells is selected by measuring the amount of fluorescence of the labeled antibody using flow cytometer.

In addition, a monoclonal antibody that competes the monoclonal antibody of the present invention in the binding to human CRTH2 can be obtained by adding a test antibody to a binding reaction-detecting system using the above-described flow cytometry to cause a reaction.

That is, a monoclonal antibody that competes the monoclonal antibody obtained in the present invention in the binding to an amino acid sequence of human CRTH2 or the three-dimensional structure thereof, can be obtained by screening an antibody in which the binding of the monoclonal antibody of the present invention is inhibited at the time when the test antibody is added.

An antibody which binds to the same epitope as the epitope recognized by the monoclonal antibody of the present invention which binds to the amino acid sequence or the three-dimensional structure of human CRTH2 can be obtained by identifying the epitope of the antibody obtained by the binding reaction-detecting system using the above-described flow cytometry and preparing a partial synthetic peptide of the identified epitope or a synthetic peptide mimicking the three-dimensional structure of the epitope and immunize with the peptide.

2. Preparation of Recombinant Antibody

As an example of preparing a recombinant antibody, a method of preparing a human chimeric antibody and a humanized antibody will be described below.

(1) Construction of Recombinant Antibody Expression Vector

A recombinant antibody expression vector is an expression vector for animal cell in which DNA encoding CH and CL of a human antibody is incorporated and can be constructed by cloning DNA encoding the CH and the CL of the human antibody to the expression vector for animal cell.

As C region of a human antibody CH and CL of any human antibody may be used. For example, CH of a γ1 subclass and CL of a κ class of a human antibody are used. cDNA is used as DNA encoding CH and CL of a human antibody, but chromosome DNA formed of an exon and an intron can be used.

The expression vector for animal cell is not particularly limited as long as a vector in which genes encoding the C region of a human antibody are incorporated and expressed. For example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)] or the like is used.

As a promotor and an enhancer used for an expression vector for animal cell, an initial promo promotor of SV40 [J. Biochem., 101, 1307 (1987)], Moloney mouse leukemia virus LTR [Biochem. Biophys. Res. Commun., 149, 960 (1987)], a promotor of the immunoglobulin H chain [Cell, 41, 479 (1985)] or the like, and an enhancer [Cell, 33, 717 (1983)] are used.

From the viewpoint that a recombinant antibody expression vector is easily constructed and easily introduced into animal cells and the amount of expressing an antibody H chain and the amount of expressing an antibody L chain in animal cells are balanced, a tandem type recombinant antibody expression vector [J. Immunol. Methods, 167, 271 (1994)] in which the antibody H chain and the antibody L chain are present on the same vector is used as the recombinant antibody expression vector, but a separator vector in which the antibody H chain and the antibody L chain are present on vectors different from each other can be used. pKANTEX93 (Pamphlet of International Publication No. 97/10354) or pEE18 [Hybridoma, 17, 559 (1998)] is used as the tandem type recombinant antibody expression vector.

(2) Obtaining of cDNA Encoding V Region of Antibody Derived from Non-Human Animal and Analysis of Amino Acid Sequence Obtaining of cDNA encoding VH and VL of a non-human antibody and analysis of the amino acid sequence can be performed in the following manner.

mRNA is extracted from hybridoma cells producing a non-human antibody and cDNA is synthesized: The synthesized cDNA is cloned to a vector such as a phage or a plasmid, thereby preparing a cDNA library.

A recombinant phage or a recombinant plasmid comprising cDNA encoding VH or VL is isolated from the above described library using DNA encoding a C region portion or a V region portion of a mouse antibody as a probe. The entire base sequences of VH or VL of a mouse antibody of interest on the recombinant phage or recombinant plasmid are respectively determined and the entire amino acid sequences of VH or VL are respectively estimated by the base sequences.

The non-human animal for preparing hybridoma cells producing a non-human antibody, a mouse, a rat, a hamster, or a rabbit may be used, but the animal is not particularly limited as long as hybridoma cells can be prepared.

A guanidine thiocyanate-cesium trifluoroacetate method [Methods in Enzymol., 154, 3 (1987)] or a kit such as RNA easy kit (QIAGEN) is used for preparation of total RNA from hybridoma cells.

An oligo (dT) immobilized cellulose column method [Molecular Cloning, A Laboratory Manual, Second Edition, Cold Spring Harbor Laboratory Press (1989)] or a kit such as an Oligo-dT30<Super>mRNA Purification Kit (TAKARA BIO INC.) is used for preparation of mRNA from total RNA. Further, mRNA can be prepared from hybridoma cells using a kit such as a Fast Track mRNA Isolation Kit (Invitrogen) or a QuickPrep mRNA Purification Kit (Pharmacia).

A known method [Molecular Cloning, A Laboratory Manual, Second Edition, Cold Spring Harbor Laboratory Press (1989), Current Protocols in molecular Biology, Supplement 1, John Wiley & Sons (1987 to 1997)], a SuperScript Plasmid System for cDNA Synthesis and Plasmid Cloning (Invitrogen), or a kit such as a ZAP-cDNA Synthesis Kit (Stratagene) is used for synthesis of cDNA and preparation of cDNA library.

When cDNA library is prepared, the vector in which cDNA obtained by synthesis using mRNA extracted from hybridoma cells as a template is incorporated is not particularly limited as long as the cDNA can be incorporated in the vector.

For example, ZAP Express [Strategies, 5, 58 (1992)], pBluescript II SK (+) [Nucleic Acids Research, 17, 9494 (1989)], λZAPII (Stratagene), λgt10, λgt11 [DNA Cloning: A Practical Approach, I, 49 (1985)], Lambda BlueMid (Clontech Laboratories, Inc.), λEx Cell, pT7T3-18U (Pharmacia), pcD2 [Mol. Cell. Biol., 3, 280 (1983)], or pUC18 [Gene, 33, 103 (1985)] is used.

*E. coli* into which cDNA library to be constructed by a phage or a plasmid vector is introduced is not particularly limited as long as the cDNA library can be introduced, expressed, and maintained. For example, XL-1Blue MRF [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], or JM105 [Gene, 38, 275 (1985)] is used.

A colony hybridization method, a plaque hybridization method using an isotope or a fluorescence-labeled probe [Molecular Cloning, A Laboratory Manual, Second Edition, Cold Spring Harbor Laboratory Press (1989)] or the like is used for selection of a cDNA clone encoding VH or VL of a non-human antibody from the cDNA library.

Further, cDNA encoding VH or VL can be prepared by preparing a primer and performing a Polymerase Chain Reaction method [hereinafter, referred to as a PCR method, Molecular Cloning, A Laboratory Manual, Second Edition, Cold Spring Harbor Laboratory Press (1989), Current Protocols in molecular Biology, Supplement 1, John Wiley & Sons (1987 to 1997)] using cDNA or cDNA library synthesized from mRNA as a template.

After selected cDNA is cut by an appropriate restriction enzyme or the like, the fragment is cloned to a plasmid such as pBluescript SK(−) (Stratagene) and the base sequence of the cDNA is determined by a base sequence analysis method being typically used. The base sequence analysis method is carried out using a base sequence automatic analyzer such as ABI PRISM 3700 (PE Biosystems) or A. L. F. DNA sequencer (Pharmacia) after the reaction of a dideoxy method [Proc. Natl. Acad. Sci. USA, 74, 5463 (1977)] or the like.

The entire amino acid sequences of VH and VL are respectively deducted from the determined base sequence and it is confirmed whether the obtained cDNA encodes the complete amino acid sequences of VH and VL of an antibody comprising the secretory signal sequence by comparing with the entire amino acid sequences [A. L. F. DNA, US Dept. Health and Human Services (1991)] of VH and VL of a known antibody.

In regard to the complete amino acid sequences of VH and VL of an antibody including the secretory signal sequence, the length of the secretory signal sequence and the N terminal amino acid sequence can be estimated by comparing the complete amino acid sequences of VH and VL of a known antibody [A. L. F. DNA, US Dept. Health and Human Services (1991)] and the sub-group to which they belong can be known. Further, amino acid sequences of each CDR of VH and VL can be also found by comparing the amino acid sequences of VH and VL of a known antibody [A. L. F. DNA, US Dept. Health and Human Services (1991)].

It is possible to confirm whether the complete amino acid sequences of VH and VL are new by performing homology search such as a BLAST method [J. Mol. Biol., 215, 403 (1990)] in any database such as SWISS-PROT or PIR-Protein using the complete amino acid sequences of VH and VL to be obtained.

(3) Construction of Human Chimeric Antibody Expression Vector

A human chimeric antibody expression vector can be constructed by cloning cDNA encoding VH and VL of a non-human antibody to the upstream of each gene encoding CH or CL of a human antibody of the recombinant antibody expression vector obtained in (1) described above.

In order to connect the 5' terminal side of CH or CL of a human antibody to the 3' terminal side of cDNA encoding VH or VL of a non-human antibody, cDNA encoding VH and VL is prepared so as to encodes appropriate amino acids and have an appropriate recognition sequence of a restriction enzyme at a linkage position.

A human chimeric antibody expression vector is constructed by cloning the prepared cDNA of VH and VL to the upstream of each gene encoding CH and CL of a human antibody of a humanized antibody expression vector obtained in (1) described above so as to be expressed in an appropriate form.

Further, cDNA encoding VH or VL of a non-human antibody is amplified by a PCR method using synthetic DNA comprising recognition sequences of an appropriate restriction enzyme at both ends and can be cloned to the recombinant antibody expression vector obtained in (1) described above.

(4) Construction of cDNA Encoding V Region of Humanized Antibody cDNA encoding VH and VL of a humanized antibody can be constructed in the following manner.

Amino acid sequences of FR of VH or VL of a human antibody for transplanting amino acid sequences of CDR of VH or VL of a non-human antibody are respectively selected. The amino acid sequence of FR to be selected is not particularly limited as long as the amino acid sequence is derived from a human antibody.

For example, the amino acid sequences of FR of a human antibody registered in the database such as Protein Data Bank or common amino acid sequences in each sub-group of FR of a human antibody [A.L.F. DNA, US Dept. Health and Human Services (1991)] or the like are used. In order to suppress decrease of binding activity of an antibody, an amino acid sequence of FR having homology (at least 60%) as high as possible with the amino acid sequence of FR of VH or VL of an original antibody is selected.

Next, the amino acid sequences of CDR of the original antibody are transplanted to the amino acid sequences of selected FR of VH or VL of the human antibody, respectively to design the amino acid sequences of VH or VL of a humanized antibody. The designed amino acid sequences are converted to DNA sequences in consideration of the frequency of use of codon shown in the base sequences of genes of the antibody [A.L.F. DNA, US Dept. Health and Human Services (1991)] to design the DNA sequences encoding the amino acid sequences of VH or VL of the humanized antibody are respectively designed.

Based on the designed DNA sequences, several strands of synthetic DNA comprising the length of approximately 100 bases are synthesized and PCR reaction is carried out using this synthetic DNA. In this case, based on the reaction efficiency of the PCR reaction and the length of DNA which can be synthesized, six strands of synthetic DNA are respectively designed preferably for the H chain and the L chain. Further, cDNA encoding VH or VL of a humanized antibody can be easily cloned to the humanized antibody expression vector obtained in (1) described above by introducing the recognition sequence of an appropriate restriction enzyme into the 5' terminal of synthetic DNA positioned at both ends.

After the PCR reaction, each of the amplified product is cloned to plasmids such as pBluescript SK (−) (Stratagene), the base sequence is determined in the same manner as the method described in (2), and then plasmids comprising DNA sequences encoding the amino acid sequences of the entire H chain and the entire L chain of a desired humanized antibody are obtained.

Alternatively, based on the designed DNA sequences, the full-length VH and the full-length VL which are respectively synthesized as one strand of long-chain DNA can be used in place of the above described PCR amplified product. Further, cDNA encoding VH or VL of a humanized antibody can be easily cloned to the humanized antibody expression vector obtained in (1) described above by introducing the recognition sequence of an appropriate restriction enzyme into both ends of the synthetic long-chain DNA.

(5) Modification of Amino Acid Sequence in V Region of Humanized Antibody

When only CDR of VH and VL of a non-human antibody is transplanted to FR of VH and VL of a human antibody, the antigen-binding activity of the humanized antibody decreases compared to that of an original non-human antibody [BIO/TECHNOLOGY, 9, 266 (1991)]. In a humanized antibody, antigen-binding activity which has decreased can be improved by identifying amino acid residues involved in direct binding to an antigen, amino acid sequences interacting with the amino acid residues of CDR and amino acids which maintain the three-dimensional structure of the antibody and thereby involved in indirect binding to an antigen among the amino acid sequences of FR of VH and VL of a human antibody, and substituting these amino acid residues with amino acid residues of an original non-human antibody.

By using X-ray crystallographic analysis [J. Mol. Biol., 112, 535 (1977)] or computer modeling [Protein Engineering, 7, 1501 (1994)] or the like to identify amino acid residues of FR associated with the antigen-binding activity, construction and analysis of the three-dimensional structure of an antibody can be performed. Further, when multiple variants are prepared for respective antibodies and the correlation between the variants and the antigen-binding activities thereof is repeatedly examined, a humanized antibody having necessary antigen-binding activity can be obtained after trial and error.

The amino acid residue of FR of VH and VL of a human antibody can be substituted by carrying out the PCR reaction described in (4) using synthetic DNA for modification. Regarding the amplified product after the PCR reaction, the base sequence is determined by the method described in (2) and desired modification which has been carried out is confirmed.

(6) Construction of Humanized Antibody Expression Vector

A humanized antibody expression vector can be constructed by cloning cDNA encoding VH or VL of the constructed recombinant antibody to the upstream of gene encoding CH or CL of a human antibody in the gene recombinant expression vector obtained in (1) described above respectively.

For example, among the synthetic DNA used for constructing VH or VL of the humanized antibody obtained in (4) and (5) described above, a recognition sequence of an appropriate restriction enzyme is introduced into the 5' terminal of synthetic DNA positioned at both ends, whereby DNA is cloned to the upstream of each gene encoding CH or CL of a human antibody of the humanized antibody expression vector obtained in (1) described above so as to be expressed in an appropriate form.

(7) Transient Expression of Recombinant Antibody

The antigen-binding activity of plural kinds of prepared gene recombinant antibodies can be efficiently evaluated by performing transient expression of a recombinant antibody using the recombinant antibody expression vectors obtained in (3) and (6) described above or expression vectors obtained by modifying the recombinant antibody expression vectors.

The host cell into which an expression vector is introduced is not particularly limited as long as the host cell is capable of expressing a recombinant antibody, and for example COS-7 cells (ATCC No: CRL1651) are used [Methods in Nucleic Acids Res., CRC Press, 283 (1991)].

An expression vector is introduced into COS-7 cells using a DEAE-dextran method [Methods in Nucleic Acids Res., CRC Press (1991)], a lipofection method [Proc. Natl. Acad. Sci. USA, 84, 7413 (1987)] or the like.

After an expression vector is introduced, the expression amount and the antigen-binding activity of the recombinant antibody in the culture supernatant are measured using an enzyme immunoassay antibody method [Monoclonal Antibodies—Principles and practice, Third edition, Academic Press (1996); Antibodies—A Laboratory Manual, Cold Spring Harbor Laboratory (1988), monoclonal antibody laboratory manual, Kodansha Scientific (1987)] or the like.

(8) Acquisition of Transformant which Stably Expresses Recombinant Antibody and Preparation of Recombinant Antibody A transformant which stably expresses a recombinant antibody can be obtained by introducing the recombinant antibody expression vectors obtained in (3) and (6) described above into an appropriate host cell.

The expression vectors are introduced into a host cell using an electroporation method [JP-A-H02-257891; Cytotechnology, 3, 133(1990)] or the like.

The host cell into which a recombinant antibody expression vector is introduced is not particularly limited as long as the host cell is capable of expressing a recombinant antibody. For example, CHO-K1 (ATCC No: CCL-61), DUkXB11 (ATCC No: CCL-9096), Pro-5 (ATCC No: CCL-1781), CHO-S (Life Technologies, Cat #11619), rat myeloma cells YB2/3HL. P2. G11. 16Ag. 20 (also referred to as YB2/0), mouse myeloma cells NS0, mouse myeloma cells SP2/0-Ag14 (ATCC No: CRL1581), mouse P3-X63-Ag8653 cells (ATCC No: CRL1580), CHO cells [Proc. Natl. Acad. Sci. USA, 77, 4216 (1980)] in which dihydrofolate reductase (hereinafter, referred to as DHFR) genes are deficient, Lec13 obtaining lectin-resistance [Somatic Cell and Molecular Genetics, 12, 55 (1986)], CHO cells in which α1,6-fucose transferase genes are deficient (Pamphlet of International Publication No. 2005/035586 and Pamphlet of International Publication No. 02/31140), or rat YB2/3HL. P2. G11. 16Ag. 20 cells (ATCC No: CRL1662) are used.

After introduction of an expression vector, the transformant which stably expresses a recombinant antibody is selected by culturing in a culture medium for culturing animal cells including an agent such as G418 sulfate (JP-A-H02-257891)).

As the culture medium for culturing animal cells, RPMI1640 culture medium (Invitrogen), GIT culture medium (Nihon Pharmaceutical Co., Ltd.), EX-CELL301 culture medium (Jay Earl H., Inc.), IMDM culture medium (Invitrogen), Hybridoma-SFM culture medium (Invitrogen), or culture media obtained by adding various additives such as FBS to these culture media is used.

A recombinant antibody is produced and accumulated in the culture supernatant by culturing an obtained transformant in a culture medium. The expression amount and the antigen-binding activity of a recombinant antibody in the culture supernatant can be measured by an ELISA method. Further, the expression amount of a recombinant antibody produced by a transformant can be increased using a DHFR amplification system (JP-A-H02-257891) or the like.

The recombinant antibody is purified using a protein A-column from the culture supernatant of a transformant [Monoclonal Antibodies—Principles and Practice, Third edition, Academic Press (1996); Antibodies—A Laboratory Manual, Cold Spring Harbor Laboratory (1988)]. Moreover, methods used for protein purification such as gel filtration, ion exchange chromatography, and ultrafiltration may be used in combination.

The molecular weight of the H chain, the L chain, or the entire antibody molecules of the purified recombinant antibody can be measured using a polyacrylamide gel electrophoresis method [Nature, 227, 680 (1970)], a western blotting method [Monoclonal Antibodies—Principles and Practice, Third edition, Academic Press (1996); Antibodies—A Laboratory Manual, Cold Spring Harbor Laboratory (1988)] or the like.

3. Activity Evaluation of Purified Monoclonal Antibody or Antibody Fragment Thereof The activity of the purified monoclonal antibody or the antibody fragment thereof of the present invention can be evaluated in the following manner.

The binding activity against the human CRTH2-expressing cell line can be measured using a fluorescent antibody method [Cancer Immunol. Immunother., 36, 373 (1993)] such as a binding reaction-detecting system using the flow cytometry in 1. (6) described above.

The CDC activity or the ADCC activity against the human CRTH2-positive cultured cell line is measured by a known measurement method [Cancer Immunol. Immunother., 36, 373 (1993); Current protocols in Immunology, Chapter 7. Immunologic studies in humans, Editor, John E, Coligan et al., John Wiley & Sons, Inc., (1993)].

4. Method of Controlling Effector Activity of Antibody

As the method of controlling the effector activity of the monoclonal antibody of the present invention, a method of controlling the amount of fucose which is α1,6-bound (also referred to as core fucose) to N-acetyl glucosamine (GlcNAc) present in the reducing terminal of a complex type N-linked sugar chain bound to 297th asparagine (Asn) in the Fc region of an antibody (Pamphlet of International Publication No. 2005/035586, Pamphlet of International Publication No. 2002/31140, and Pamphlet of International Publication No. 00/61739) and a method of controlling the activity by modifying the amino acid residues in the Fc region of an antibody are known. The effector activity of the monoclonal antibody of the present invention can be controlled by any of the method.

The effector activity indicates antibody-dependent activity caused through the Fc region of an antibody, and ADCC activity, CDC activity, and antibody-dependent phagocytosis (ADP activity) by phagocytes such as microphages or dendritic cells are known.

As an example of the method of measuring effector activity, inflammatory cells as a target, human peripheral blood mononuclear cells (PBMC) as an effector, and inflammatory cell-specific antibody are mixed with each other and incubated for approximately 4 hours, and then lactate dehydrogenase (LDH) released as an index of cell injury can be measured. Alternatively, an antibody that recognizes a blood cell-specific antigen such as CD20 is mixed with human PBMC and incubated, then released LDH and a decrease in number of cells as effector activity can be measured using flow cytometry.

The effector activity of an antibody can increase or decrease by controlling the content of core fucose in the complex type N-linked sugar chain of Fc of the antibody. A method of expressing an antibody using CHO cells in which α1,6-fucose transferase genes are deficient may be exemplified as the method of decreasing the content of fucose bound to the complex type N-linked sugar chain which binds to Fc of the antibody, and an antibody to which fucose does not bind can be obtained. The antibody to which fucose does not bind has high ADCC activity.

On the other hand, method of expressing an antibody using a host cell into which α1,6-fucose transferase genes are introduced may be exemplified as the method of increasing the content of fucose bound to the complex type N-linked sugar chain which binds to Fc of the antibody, and an antibody to which fucose binds can be obtained. The antibody to which fucose binds has lower ADCC activity than the antibody to which fucose does not bind.

Moreover, the ADCC activity or the CDC activity can increase or decrease by modifying the amino acid residues in the Fc region of an antibody. For example, the CDC activity of an antibody can be increased using the amino acid sequences in the Fc region described in US-A-2007/0148165.

In addition, the ADCC activity or the CDC activity can be increased or decreased by performing amino acid modification described in U.S. Pat. No. 6,737,056, U.S. Pat. No. 7,297,775, or U.S. Pat. No. 7,317,091.

The antibodies of the present invention include an antibody whose half-life in blood is controlled by performing amino acid modification described in JP-A-2013-165716 or JP-A-2012-021004 or the like according to the amino acid modification or sugar chain modification in the antibody constant region described above to control the reactivity to an Fc receptor.

Further, an antibody whose effector activity or half-life in blood is controlled can be obtained by combining the above-described methods and using the combined method for one antibody.

5. Method of Treating Disease Using Monoclonal Antibody or Antibody Fragment Thereof of the Present Invention The antibody of the present invention may be used for treating a disease associated with human CRTH2. Examples of administration routes include oral administration and parenteral administration such as oral cavity administration, tracheobronchial administration, rectally administration, subcutaneous administration, intramuscular administration, intravenous administration, or intraperitoneal administration. Examples of administration forms include sprays, capsules, tablets, powders, granules, syrups, emulsions, suppositories, injections, ointments, and tapes.

Examples of the formulation suitable for oral administration include emulsions, syrups, capsules, tablets, powders, and granules.

Liquid preparations such as emulsions or syrups are produced using, as additives, water; saccharides such as sucrose, sorbitol, and fructose; glycols such as polyethylene glycol and propylene glycol; oils such as sesame oil, olive oil, and soybean oil; preservatives such as p-hydroxybenzoic acid esters; and flavors such as strawberry flavor and peppermint.

Capsules, tablets, powders, or granules are produced using, as additives, excipients such as lactose, glucose, sucrose, and mannitol; disintegrating agent such as starch and sodium alginate; lubricants such as magnesium stearate and talc; binders such as polyvinyl alcohol, hydroxy propyl cellulose, and gelatin; surfactants such as fatty acid ester; and plasticizers such as glycerin.

Examples of the formulation suitable for parenteral administration include injections, suppositories, and sprays.

An injection is produced using a carrier formed of a salt solution, a glucose solution, or a mixture of these.

A suppository is produced using a carrier such as cacao butter, hydrogenated fats, or carboxylic acid.

A spray is produced using a carrier which doesn't stimulate the oral cavity and the respiratory tract mucosa of a recipient, and enables the monoclonal antibody or the antibody fragment thereof of the present invention to disperse as fine particles to be easily absorbed. As the carrier, for example, lactose or glycerin is used. Further, a spray can be produced as an aerosol or dry powder.

Moreover, the components exemplified as additives for oral administration can be also added to the above-described parenteral agents.

6. Method of Diagnosing Disease Using Antibody or Antibody Fragment Thereof of the Present Invention A disease associated with human CRTH2 can be diagnosed by detecting or measuring human CRTH2 or human CRTH2-expressing cells using the antibody or the antibody fragment thereof of the present invention.

The allergic disease which is one of the diseases associated with human CRTH2 can be diagnosed, for example, by detecting human CRTH2 expressed on inflammatory cells present in peripheral blood, sputum, nasal discharge, or bronchioalveolar lavage derived from patients using an immunological technique such as flow cytometer.

The immunological technique is a method of detecting or measuring the amount of antibody or the amount of antigen using a labeled antigen or antibody. For example, a radioactive substance-labeled immunoantibody method, an enzyme immunoassay method, a fluorescent immunoassay method, a luminescent immunoassay method, a western blotting method, and a physico-chemical method are used.

The radioactive substance-labeled immunoantibody method is carried out, for example, by reacting the antibody or the antibody fragment thereof of the present invention with an antigen or cells expressing an antigen, reacting a radiation-labeled anti-immunoglobulin antibody or a binding fragment with the antigen or the cells, and then measurement is carried out using a scintillation counter or the like.

Examples of the enzyme immunoassay method include a method in which the antibody or the antibody fragment thereof of the present invention is allowed to react with an antigen or cells expressing an antigen or the like, then an anti-immunoglobulin antibody or a binding fragment which has been labeled thereof is allowed to react therewith, and then the coloring dye is measured using an spectrophotometer. For example, a sandwich ELISA method or the like is used.

As a marker used for the enzyme immunoassay method, known enzyme labeling [Enzyme Immunoassay method, Igaku-Shoin Ltd. (1987)] can be used. For example, alkaline phosphatase labeling, peroxidase labeling, luciferase labeling, or biotin labeling is used.

The sandwich ELISA method is a method of trapping an antigen which is a subject for detection or measurement after an antibody binds to a solid phase and reacting a second antibody with the trapped antigen. According to the ELISA method, two kinds of antibodies which are antibodies or the antibody fragments thereof recognizing an antibody intended to be detected or measured and have antigen recognition sites different from each other are prepared, the first antibody or the antibody fragment among these are adsorbed to a plate (for example, 96-well plate) in advance, and then the second antibody or the antibody fragment is labeled using a fluorescent substance such as FITC, an enzyme such as peroxidase, biotin, or the like.

Cells or a disrupted liquid thereof, tissues or a disrupted liquid thereof, a cell culture supernatant, serum, pleural effusion, ascites fluid, or intraocular fluid, which are separated from a living body are allowed to react with the plate to which the above-described antibody is adsorbed, then allowed to react the labeled monoclonal antibody or the antibody fragment thereof with the plate, and then a detection reaction is carried out corresponding to the labeling substance. The antigen concentration in a test sample is calculated using a calibration curve prepared by gradually diluting the antigen of a known concentration.

As the antibody used for the sandwich ELISA method, any of a polyclonal antibody or a monoclonal antibody may be used, and an antibody fragment such as Fab, Fab', or F(ab')$_2$ may be used. As the combination of two kinds of antibodies used for the sandwich ELISA method, a combination of monoclonal antibodies or antibody fragments thereof recognizing different epitopes may be used or a combination of a polyclonal antibody and a monoclonal antibody or an antibody fragment thereof may be used.

A fluorescence immunoassay method is carried out by a method described in literature [Monoclonal Antibodies—Principles and practice, Third edition, Academic Press (1996), monoclonal antibody experiment manual, Kodansha Scientific (1987)] or the like. As the label used for the fluorescence immunoassay method include known fluorescent labels [fluorescence antibody method, Soft Science Inc. (1983)] may be exemplified. Further, fluorescein isothiocyanate (FITC) or tetramethyl rhodamine isothiocyanate (RITC) may be exemplified.

A luminescent immunoassay method is carried out by a method described in literature [bioluminescence and chemiluminescence clinical examination 42, Hirokawa Shoten (1998)] or the like. As a marker used for the luminescent immunoassay method, known luminescent label may be exemplified. Examples thereof include acridinium ester and lophine.

Western blotting method is a method in which an antigen or cells expressing an antigen is fractionated by sodium dodecyl sulfate (SDS)-PAGE [Antibodies—A Laboratory Manual Cold Spring Harbor Laboratory (1988)], the gel is blotted onto a polyvinylidene fluoride (PVDF) membrane or a nitrocellulose membrane, the membrane is allowed to react with an antigen-recognizing antibody or the antibody fragment, further allowed to react with an anti-mouse IgG antibody or a binding fragment which is labeled with a fluorescent substance such as FITC, enzyme such as peroxidase or biotin, or the like, and the label is visualized to confirm the reaction. An example will be described below.

Cells or tissues that express a polypeptide comprising the amino acid sequence represented by SEQ ID NO: 2 are dissolved and 0.1 to 30 μg of protein per lane is electrophoresed under reducing conditions by an SDS-PAGE method. A blocking operation is performed by transferring the electrophoresed protein to a PVDF membrane and causing a reaction with 1% to 10% BSA-PBS at room temperature for 30 minutes.

Here, the antibody of the present invention is reacted and washed with PBS containing 0.05% to 0.1% of Tween-20 (hereinafter, referred to as Tween-PBS), and then a peroxidase-labeled goat anti-mouse IgG is reacted at room temperature for 2 hours. It is washed with Tween-PBS and a band to which a monoclonal antibody binds is detected using ECL Western Blotting Detection Reagents (manufactured by Amersham plc) or the like to detect a polypeptide comprising the amino acid sequence represented by SEQ ID NO: 2. As the antibody used for detection in western blotting, an antibody which can bind to a polypeptide that does not have a natural type three-dimensional structure is used.

The physico-chemical method is performed by binding the monoclonal antibody or the antibody fragment thereof of the present invention to human CRTH2 which is an antigen to form an aggregate and detecting the aggregate. Other examples of the physico-chemical method include a capillary tube method, a one-dimensional immunodiffusion method, an immunoturbidimetric method, and a latex immunoturbidimetory method [Kanai's Manual of Clinical Laboratory Medicine, Kanehara-Shuppan (1998)].

In a latex immunoturbidimetory method, when an antigen-antibody reaction is carried out by the corresponding antigen or antibody using a carrier such as polystyrene latex in which an antibody or an antigen is sensitized and which has a particle diameter of approximately 0.1 to 1 μm, scattered light in the reaction solution increases and transmitted light decreases. The antigen concentration in a test sample or the like is measured by detecting this change as the absorbance or integrate sphere turbidity.

The method of determining therapeutic efficacy, of the antibody before treatment is started, using the antibody or the antibody fragment thereof of the present invention is exemplified as follows.

First, before treatment is started, the peripheral blood, sputum, bronchioalveolar lavage, and nasal discharge or the like are collected from a patient, the antibody or the antibody fragment thereof of the present invention is added to the suspension, and anti-inflammatory cell activity including removal of inflammatory cells and inhibitory activity against biofunctional molecules such as Th2 type cytokine is measured after a certain period of time. In a case where anti-inflammatory cell activity is detected as the result of measurement, it is possible to determine, before treatment, that the antibody or the antibody fragment thereof of the present invention is effective for the treatment for patients having the peripheral blood, sputum, nasal discharge or the like.

EXAMPLES

Hereinafter, the present invention is described by examples, but the present invention is not limited thereto.

Example 1

Establishment of Human CRTH2-Expressing Cells (1) Preparation of Human CRTH2 Expression Vector cDNA of human CRTH2 (hereinafter, also referred to as CRTH2) was entirely synthesized and used for the following test. The cDNA sequence of human CRTH2 is represented by SEQ ID NO: 1 and the amino acid sequence thereof is represented by SEQ ID NO: 2.

(i) Construction of Human CRTH2 Gene Expression pKANTEX93 Vector

A human CRTH2 gene expression pKANTEX93 vector was constructed by connecting cDNA of human CRTH2 with a vector pKANTEX93 (Pamphlet of International Publication No. 97/10354) using restriction enzymes EcoRI and KpnI.

(ii) Construction of Human CRTH2 Gene Expression pAMoh Vector

A human CRTH2 gene expression pAMoh vector was constructed by incorporating human CRTH2 genes in pAMoh (Pamphlet of International Publication No. 03/087366) using restriction enzymes KpnI and HindIII.

(2) Establishment of Human CRTH2-Expressing CHO/DG44 Cells

DHFR gene-deficient CHO (Chinese hamster ovary) cell DG44 lines (CHO/DG44 cells) were obtained from Mitsubishi Chemical Corporation, Yokohama Research Institute. and used for establishment of human CRTH2-expressing cells. IMDM (GIBCO Inc.) to which 10% dialyzed fetal bovine serum (dFBS) (GIBCO Inc.), HT [hypoxanthine (H) and thymidine (T)] supplement (GIBCO Inc.) and 50 µg/mL of gentamicin (NACALAI TESQUE, Inc.) was added (hereinafter, abbreviated as IMDM culture medium) were used for culturing.

First, the human CRTH2 gene expression pKANTEX93 vector prepared in (1)-(i) was cleaved by restriction enzyme AatII treatment and then the obtained linear DNA was purified and dissolved in sterile water. This DNA was introduced to CHO/DG44 cells by an electroporation method and cultured in IMDM culture medium from which HT supplement was removed for approximately 3 days.

Thereafter, drug-resistant cells were selected using IMDM to which 10% dFBS, 0.5 mg/mL of G418 (NACALAI TESQUE, Inc.), and 50 µg/mL of gentamicin (NACALAI TESQUE, Inc.) were added (hereinafter, abbreviated as IMDM selection medium). The selected drug-resistant cells were seeded in a 96-well plate at 75 cells/plate and cultured in IMDM selection medium for approximately 2 weeks. The cells in each well were observed using a microscope and a single clone was sequentially expanded.

The obtained drug-resistant cells were peeled using a 0.02% EDTA solution (NACALAI TESQUE, Inc.), washed with phosphate buffered saline (PBS), and suspended with PBS containing 2% fetal bovine serum (FBS), 0.05% $NaN_3$, and 1 mM EDTA (staining medium, hereinafter, abbreviated as SM). Next, the cells were seeded in a 96-well plate such that each well had $2\times10^5$ cells and centrifuged at 1700 rpm for 2 minutes.

After the supernatant was removed, a PE-labeled anti-human CRTH2 antibody (Beckman Coulter Inc.) prepared using SM was added thereto to cause a reaction at 4° C. for 1 hour. The cells were washed and suspended with SM, and the fluorescent intensity was analyzed by flow cytometer (BD Biosciences, FACS CantoII). A clone which expressed human CRTH2 at a high level was selected and this cell was set to human CRTH2 expressing CHO/DG44 cell.

(3) Preparation of FLAG Fusion Human CRTH2 Expression Vector (i) Construction of FLAG Fusion Human CRTH2 Gene Expression pAMoh Vector Human CRTH2 (SEQ ID NO: 5) with a C terminal to which a FLAG tag was added was amplified by polymerase chain reaction (hereinafter, referred to as PCR) from the human CRTH2 gene expression pAMoh prepared in (1)-(ii) using primer human CRTH2FLAG-A (SEQ ID NO: 3) and human CRTH2 FLAG-B (SEQ ID NO: 4) and was connected to a vector pAMoH (Pamphlet of International Publication No. 03/087366) using restriction enzymes KpnI and HindIII, thereby constructing a FLAG fusion human CRTH2 gene expression pAMoh vector.

(ii) Construction of FLAG Fusion Human CRTH2 Expression Vector pKANTEX93 Vector

Human CRTH2 with a C terminal to which a FLAG tag was added was amplified by PCR from the FLAG fusion human CRTH2 gene expression pAMoh vector prepared in (3)-(i) using primer human CRTH2FLAG-C(SEQ ID NO: 6) and human CRTH2 FLAG-D (SEQ ID NO: 7) and was connected to a vector pKANTEX93 (Pamphlet of International Publication No. 97/10354) using restriction enzymes EcoRI and KpnI, thereby constructing a FLAG fusion human CRTH2 gene expression pKANTEX93 vector.

(4) Establishment of FLAG Fusion Human CRTH2 Expressing 3Y1-B Cells

Rat 3Y1-B cells were obtained from Riken BioResource Center and used for establishment of FLAG fusion human CRTH2-expressing cells. 10% FBS (GIBCO Inc.) and DMEM (GIBCO Inc.) to which 50 µg/mL of gentamicin (NACALAI TESQUE, Inc.) was added (hereinafter, abbreviated as DMEM culture medium) were used for culturing.

The FLAG fusion human CRTH2 gene expression pKANTEX93 vector prepared in (3)-(ii) was cleaved by restriction enzyme AatII treatment and then the obtained linear DNA was purified and dissolved in sterile water. This DNA was introduced to 3Y1-B cells according to a Lipofection method using Fugene6 (Promega Corporation) and cultured in DMEM culture medium for 3 days. Thereafter, drug-resistant cells were selected using the DMEM to which 10% FBS, 0.8 mg/mL of G418 (NACALAI TESQUE, Inc.), and 50 µg/mL of gentamicin (NACALAI TESQUE, Inc.) were added (hereinafter, abbreviated as DMEM selection medium).

The obtained drug-resistant cells were peeled using a 0.05% trypsin solution (Invitrogen), washed with PBS, and suspended with SM. Next, the cells were seeded in a 96-well plate at $2\times10^5$ cells/well and centrifuged at 1700 rpm for 2 minutes. After the supernatant was removed, a PE-labeled anti-human CRTH2 antibody (Beckman Coulter Inc.) prepared using SM was added thereto to cause a reaction at 4° C. for 1 hour. The cells were washed and suspended by SM, and the fluorescent intensity was analyzed by flow cytometer (BD Biosciences, FACS Aria). A fraction which expressed FLAG fusion human CRTH2 at a high level was sorted out and expansively cultured, and this cell was set to FLAG fusion human CRTH2 expressing 3Y1-B cell.

Example 2

Preparation of Monoclonal Antibody Against Human CRTH2

(1) Immunization to Rat

In order to obtain a monoclonal antibody against human CRTH2, a female WKY/NCrlCrlj rat (WKY rat) (Charles River Laboratories) who was 9 weeks old at the time of first administration was immunized.

At the time of first administration, $5 \times 10^6$ cells of FLAG fusion human CRTH2-expressing 3Y1-B cells were suspended in 100 µL of physiological saline (Otsuka Pharmaceutical factory Inc.) and combined with 100 µL of Sigma Adjuvant System (registered trademark) (Sigma-Aldrich Co. LLC) to prepare 200 µL of cell suspension, and then 100 µL of the cell suspension was administered intramuscularly to both right and left portions of the base of the tail of a WKY rat.

After 2 weeks from the first administration, $5 \times 10^6$ cells of FLAG fusion human CRTH2-expressing 3Y1-B cells were suspended in a 200 µL physiological saline and administered in the same manner as described above.

(2) Preparation of Hybridomas

After 3 days from the second immunization described in (1), iliac lymph nodes were surgically removed from the WKY rat for cell fusion.

First, the removed iliac lymph nodes were ground using slide glass so that the tissues were loosened. The iliac lymph node tissues were suspended by Minimum Essential Media (MEM) (Invitrogen) and unnecessary tissues were removed by passing through a cell strainer. The supernatant was removed by centrifugation at 1200 rpm for 5 minutes and resuspended with MEM to obtain iliac lymph node cells.

To the obtained iliac lymph node cells, ⅕ number of mouse myeloma cell lines P3-U1 (ATCC) were added. The supernatant was removed by centrifugation and warmed in a warm bath at 37° C., 500 µL of a PEG solution [solution obtained by mixing 1 mL of polyethylene glycol 1000 (Junsei Chemical Co., Ltd.) with 1 mL of MEM and adding 350 µL of DMSO (dimethyl sulfoxide) (Sigma-Aldrich Co. LLC) thereto] was gently added thereto, and 1 mL of MEM was added every minute for five times and then 45 mL of MEM was added thereto.

The supernatant was removed by centrifugation at 900 rpm for 5 minutes, and the cells were suspended with HAT culture medium [500 mL of RPMI-1640 (Wako Pure Chemical Industries) to which 10 mL of HAT (hypoxanthine (H), aminopterin (A), and thymidine (T)) solution (GIBCO Inc.), 0.5 mL of 55 mmol/L 2-mercaptoethanol (Invitrogen), 50 mL of fetal bovine serum (Moregate Biotech), and 0.5 mL of 10 mg/mL gentamicin solution (NACALAI TESQUE, Inc.) were added], seeded in a 96-well plate, and cultured.

(3) Hybridoma Screening

After hybridomas seeded in (2) were cultured for 7 days, the culture supernatant of each well was collected and the reactivity against human CRTH2 was analyzed. Human CRTH2 expressing CHO/DG44 cells and CHO/DG44 cells were respectively set to the positive control cells and the negative control cells. First, the positive control cells and the negative control cells were peeled using 0.02% EDTA solution (NACALAI TESQUE, Inc.) and seeded in a 96-well plate at $1 \times 10^5$ cells/50 µL for each well, and 50 µL of the culture supernatant was added thereto to cause a reaction at 4° C. for 30 minutes.

The cells were washed and suspended with 100 µL of Anti-rat IgG (Fc)-Dylight488 (Abcam plc.) diluted 300 times with SM to cause a reaction at 4° C. for 30 minutes. The cells were washed again and suspended with SM, and then the fluorescent intensity was analyzed by flow cytometry (BD Biosciences, FACS CantoII).

Single cell cloning was performed twice on hybridomas in wells specifically reacting with human CRTH2 expressing CHO/DG44 cells using a cloning culture medium [S Medium Cloning Medium CM-B (EIDIA Co., Ltd.) to which 0.5 mL of 10 mg/mL gentamicin (NACALAI TESQUE, Inc.) and 5 mL of HT supplement (GIBCO Inc.) was added] by a limiting dilution method. Finally, hybridoma Lym2 clone (hereinafter, referred to as hybridoma Lym2) showing strongest flow cytometry reactivity against human CRTH2 expressing CHO/DG44 cells was established.

(4) Identification of Subclass of Antibody Contained in Culture Supernatant of Hybridoma Lym2

The culture supernatant obtained by culturing hybridoma Lym2 for 3 days was diluted 10 times with PBS (NACALAI TESQUE, Inc.) and the subclass was analyzed by Rat Monoclonal Antibody Isotyping Test Kit (Abd Serotec Inc.) according to the attached instructions using 150 µL of the diluent.

As the result, the rat anti-human CRTH2 monoclonal antibody contained in the culture supernatant of hybridoma Lym2 (hereinafter, also simply abbreviated as Lym2 antibody) was found to be a rat IgG2b antibody.

(5) Purification of Lym2 Antibody

The hybridoma Lym2 was cultured for 1 week using a culture medium obtained by adding 5% Fetal Bovine Serum Ultra Low IgG (Invitrogen) to Hybridoma-SFM (Invitrogen). The culture supernatant was recovered for purification.

The Lym2 antibody was purified from the culture supernatant using Prosep-G (GE Healthcare). First, the culture supernatant was loaded onto a column, and the column was washed with PBS and eluted by elution buffers having pHs of 5.0, 3.5, and 3.0 (0.1 M citric acid monohydrate-NaOH/ pH 5.0, 3.5, and 3.0) in this order. The eluted fractions were immediately neutralized by a neutralization buffer (2 M Tris-HCl/pH 8.5).

The absorbance (280 nm) of each fraction was measured and a series of fractions having high measurement values were recovered as an antibody fraction. The antibody fraction was dialyzed with PBS and allowed to pass through a filter, 0.22 µm to obtain purified protein. The absorption coefficient at 280 nm was set to 1.4 and the concentration was calculated.

Example 3

Evaluation of Antigen-Binding Properties of Lym2 Antibody Using Flow Cytometry

FLAG fusion human CRTH2-expressing 3Y1-B cells were peeled using a 0.05% trypsin solution (Invitrogen), washed with PBS, and suspended with SM. Further, the cells were seeded in a 96-well plate such that one well has $2 \times 10^5$ cells and centrifuged at 1700 rpm for 2 minutes. After the supernatant was removed, 100 µL of Lym2 antibody prepared to have a concentration of 10 µg/mL using SM was added thereto to cause a reaction at 4° C. for 1 hour.

After the cells were washed, Anti-rat IgG-FITC (Beckman Coulter Inc.) diluted 100 times with SM was added to the cells to cause a reaction at 4° C. for 1 hour. The cells were washed again and suspended with SM, and the fluorescent intensity was analyzed by flow cytometry (BD Biosciences, FACS CantoII). As the result, binding of the Lym2 antibody to FLAG fusion human CRTH2-expressing 3Y1-B cells was observed.

Example 4

Cloning of Gene of Heavy Chain and Light Chain Variable Region of Lym2 Antibody

The hybridoma Lym2 washed with PBS was dissolved using RNA iso plus (TAKARA BIO INC.) according to attached instructions, thereby preparing total RNA. The obtained total RNA was dissolved in DEPC treated water (Invitrogen). Next, mRNA was purified from the obtained total RNA using Oligotex-dT30<Super>mRNA Purification Kit (From total RNA) (TAKARA BIO INC.) according to attached instructions. Then, cDNA was prepared from the purified mRNA using SMART RACE cDNA Amplification Kit (Clontech Laboratories, Inc.) according to attached instructions.

Using obtained cDNA as a template, genes of rat IgG2b heavy chain were amplified by PCR using primer Rat IgG2bH-A (SEQ ID NO: 8) and Rat IgG2bH-B (SEQ ID NO: 9) and genes of rat light chain (κ chain) were amplified by PCR using primer Ratk-A (SEQ ID NO: 10) and Ratk-B (SEQ ID NO: 11). Sub-cloning was performed on the amplified genes and the base sequences were analyzed.

As the result, the base sequences and amino acid sequences of VH and VL of Lym2 antibody including signal sequences were identified. The base sequences of VH and VL were represented by SEQ ID NOS: 12 and 14 respectively and the amino acid sequences thereof were represented by SEQ ID NOS: 13 and 15 respectively. Moreover, the sequences of VH and VL of Lym2 antibody which did not have signal sequences were identified based on the report of Kabat et al. [Sequences of Proteins of Immunological Interest, US Dept. Health and Human Services (1991)].

The base sequences of VH and VL from which signal sequences were removed were represented by SEQ ID NOS: 16 and 18 respectively and the amino acid sequences were represented by SEQ ID NOS: 17 and 19 respectively. The amino acid sequences of CDR1, CDR2, and CDR3 of VH of Lym2 antibody were represented by SEQ ID NOS: 20, 21, and 22 respectively and the amino acid sequences of CDR1, CDR2, and CDR3 of VL of Lym2 antibody were represented by SEQ ID NOS: 23, 24, and 25 respectively.

Example 5

Preparation of Rat/Human Chimeric Lym2 Antibody (1) Construction of Rat/Human Chimeric Lym2 Antibody Expression Vector A rat/human chimeric Lym2 antibody expression vector was prepared by respectively connecting gene of heavy chain and a light chain variable region of Lym2 antibody to gene of heavy chain and a κ chain constant region of IgG1 using the following method.

First, the sequence of SEQ ID NO: 26 as VH and the sequence of SEQ ID NO: 27 as VL were entirely synthesized. From the synthesized sequences, the VH was amplified by PCR using a primer chLym2VH-A (SEQ ID NO: 28) and a primer chLym2VH-B (SEQ ID NO: 29) and the VL was amplified by PCR using a primer chLym2VL-A (SEQ ID NO: 30) and a primer chLym2VL-B (SEQ ID NO: 31).

A gene fragment was subjected to agarose gel electrophoresis and purified by QIAquick Gel Extraction Kit (QIAGEN). Sub-cloning to vectors by In-Fusion HD Cloning Kit (Clontech Laboratories, Inc.) was performed using this fragment, a human κ constant region expression vector (BglII/BsiWI treatment), and a human heavy chain (IgG1) constant region expression vector (SalI/NheI treatment) according to the attached instructions.

A rat/human chimeric Lym2 antibody (hereinafter, referred to as chLym2) expression vector was prepared by performing transformation to $E. coli$ DH5α competent cells (TAKARA BIO INC.), plasmid extraction, and sequence confirmation.

(2) Preparation of chLym2 Transiently Expressing Cell Line

In order to prepare chLym2 transiently expressing cell line, the expression vector prepared in (1) was introduced into a host cell according to the following method using Freestyle (registered trademark) MAX CHO Expression System (Lifetechnologies Corporation) according to the attached instructions. FUT8 knockout CHO cells (Pamphlet of International Publication No. 2005/035586 and Pamphlet of International Publication No. 02/31140) which were acclimated to FreeStyle (registered trademark) CHO Expression Medium (Lifetechnologies Corporation) were used as the host cell.

312.5 μg of chLym2 antibody expression vector (vector obtained by mixing a light chain expression vector with a heavy chain expression vector at a mixing ratio of 1:2) prepared in (1) was dissolved in 20 mL of Opti-Pro SFM (Invitrogen) and 312.5 μL of Freestyle MAX Reagent (Invitrogen) was dissolved in 20 mL of Opti-Pro SFM and these two liquids were allowed to stand at room temperature for 5 minutes. The two liquids were mixed with each other and allowed to stand at room temperature for 15 minutes. All of the mixed solution was added to 250 mL of host cell culture solution ($1 \times 10^6$ cells/mL), thereby obtaining a chLym2 transiently expressing cell line.

(3) Purification of chLym2

ChLym2 transiently expressing cell line obtained in (2) was suspended with Free style CHO expression medium (Invitrogen) to which 8 mM of L-glutamine (Invitrogen) was added and cultured using an Erlenmeyer flask for 5 days, and the culture supernatant was recovered. The recovered culture supernatant was centrifuged and filtered using a filter, 0.22 μm, thereby preparing a culture supernatant containing chLym2.

ChLym2 was purified from the prepared culture supernatant using MabSelect SuRe (GE Healthcare). First, the culture supernatant was loaded onto a column, and the column was washed with PBS and eluted by elution buffers having pHs of 5.0, 3.5, and 3.0 (0.1 M citric acid monohydrate-NaOH/pH 5.0, 3.5, and 3.0) in this order. The eluted fractions were immediately neutralized with a neutralization buffer (2 M Tris-HCl/pH 8.5).

The absorbance at 280 nm ($A_{280}$) of each fraction was measured and a series of fractions having high measurement values were recovered as an antibody fraction. The antibody fraction was dialyzed with PBS and allowed to pass through a filter, 0.22 μm to obtain purified protein. The absorption coefficient at 280 nm was set to 1.37 and the concentration was calculated.

Example 6

Preparation of Humanized Antibody (1) Design of Heavy Chain and Light Chain Variable Region of Humanized Lym2 Antibody (i) Design of Amino Acid Sequences of VL and VH of Humanized Lym2 Antibody The amino acid sequences of VL of humanized Lym2 antibodies were designed in the following manner.

First, an amino acid sequence of FR of VL of a human antibody suitable for transplantation of the amino acid sequences of CDRs 1 to 3 of VL of the Lym2 antibody (SEQ ID NOS: 23, 24, and 25) was selected in the following manner.

In a case of known human antibody heavy chain variable region sequences, a human antibody sequence having high homology with the FR sequence of VL of Lym2 antibody was searched using BLASTP database provided by The National Center for Biotechnology Information. As the result, the human antibody sequence of GeneBank ID: ABA71374.1 exhibited the highest homology, so the FR of this antibody was selected. LV0 (SEQ ID NO: 33) was designed by transplanting the amino acid sequences of CDRs 1 to 3 of VL of Lym2 antibody represented by SEQ ID NOS: 23, 24, and 25 into suitable positions in the human antibody FR sequences determined in the above-described manner.

Next, the amino acid sequences of VH of the humanized Lym2 antibody were designed in the following manner. An amino acid sequence of FR of VH of a human antibody suitable for transplantation of the amino acid sequences of CDRs 1 to 3 of VH of the Lym2 antibody (SEQ ID NOS: 20, 21, and 22) was selected in the following manner. Similar to VL, a human antibody sequence having high homology with the FR sequence of VH of Lym2 antibody was searched based on the BLASTP database.

As the result, the human antibody sequence of GeneBank ID: AAY33331.1 exhibited the highest homology, so the FR of this antibody was selected. HV0 (SEQ ID NO: 49) was designed by transplanting the amino acid sequences of CDRs 1 to 3 of VH of Lym2 antibody represented by SEQ ID NOS: 20, 21, and 22 into suitable positions in the human antibody FR sequences determined in the above-described manner.

LV0 which is the amino acid sequence of VL of the humanized Lym2 antibody and HV0 which is the amino acid sequence of VH of the humanized Lym2 antibody designed in the above-described manner are sequences obtained by transplanting only the amino acid sequences of CDRs derived from Lym2 which is a rat monoclonal antibody to the amino acid sequence of FR of the selected human antibody. However, typically, in a case of preparing a humanized antibody, the binding activity frequently decreases when the amino acid sequences of CDRs of a rodent-derived antibody are simply transplanted into the FR of a human antibody.

In order to avoid the decrease of binding activity, amino acid residues which are considered to affect the binding activity, among the amino acid residues of FR which are different between the human antibody and the rodent-derived antibody, are substituted along with the transplantation of the amino acid sequences of CDRs. In the present example, amino acid residues of FR which are considered to affect the binding activity were identified and substituted in the following manner.

First, a three-dimensional structure of an antibody variable region formed by LV0 which is the amino acid sequence of VL of the humanized Lym2 antibody and HV0 which is the amino acid sequence of VH of the humanized Lym2 antibody designed in the above-described manner (hereinafter, referred to as LV0HV0) was constructed using a computer modeling technique.

Discovery Studio (Accelrys) was used for preparing a three-dimensional structure coordinate and displaying a three-dimensional structure. In addition, a computer model of a three-dimensional structure of the variable region of Lym2 antibody was constructed in the same manner. Further, amino acid residues which were different from those of Lym2 antibody were selected from the amino acid sequences of FR of VL and VH of LV0HV0, amino acid sequences modified to amino acid residues of the Lym2 antibody were prepared, and then a three-dimensional structure model was constructed in the same manner as described above. Amino acid residues which are expected to affect the binding activity of the antibodies were identified by comparing the prepared three-dimensional structures of each variable region of Lym2 antibody, LV0HV0, and variant.

As the result, as the amino acid residues among the amino acid residues of FR of LV0HV0 which are considered to change the three-dimensional structures of antigen-binding sites and affect the binding activity of the antibodies, 2nd Ile, 4th Met, 15th Pro, and 85th Ala in the amino acid sequences of SEQ ID NO: 33 were selected in a case of LV0 and 18th Leu, 77th Asn, 93rd Val, and 117th Thr in the amino acid sequence of SEQ ID NO: 49 were selected in a case of HV0.

The VL and VH of a humanized antibody comprising various modifications were designed by performing amino acid modification, that is, substitution of at least one amino acid sequence among the selected amino acid residues with amino acid residues present in the same site of Lym2 antibody. Specifically, in a case of the VL, at least one modification among amino acid modifications of substituting 2nd Ile with Val, 4th Met with Leu, 15th Pro with Leu, or 85th Ala with Pro in the amino acid sequence of SEQ ID NO: 33 was introduced. In a case of the VH, at least one modification among amino acid modifications of substituting 18th Leu with Met, 77th Asn with Ser, 93rd Val with Thr, or 117th Thr with Val in the amino acid sequence of SEQ ID NO: 49 was introduced.

LV0HV0, LV1HV0, LV2aHV0, LV2bHV0, LV2cHV0, LV3aHV0, LV3bHV0, LV4HV0, LV0HV4, LV1HV4, LV2aHV4, LV2bHV4, LV2cHV4, LV3aHV4, LV3bHV4, LV4HV4, LV0HV1, LV0HV2a, LV0HV2b, and LV0HV3 were respectively designed as antibody variable regions of LV0HV0, or the humanized Lym2 antibody in which at least one amino acid residue present in FR of LV0HV0 is modified.

In the description below, humanized Lym2 antibodies comprising the above-described variable regions are respectively abbreviated as LV0HV0, LV1HV0, LV2aHV0, LV2bHV0, LV2cHV0, LV3aHV0, LV3bHV0, LV4HV0, LV0HV4, LV1HV4, LV2aHV4, LV2bHV4, LV2cHV4, LV3aHV4, LV3bHV4, LV4HV4, LV0HV1, LV0HV2a, LV0HV2b, and LV0HV3.

The amino acid sequences of the light chain variable region LV0 (SEQ ID NO: 33), LV1 (SEQ ID NO: 35), LV2a (SEQ ID NO: 37), LV2b (SEQ ID NO: 39), LV2c (SEQ ID NO: 41), LV3a (SEQ ID NO: 43), LV3b (SEQ ID NO: 45), LV4 (SEQ ID NO: 47), and the heavy chain variable region HV0 (SEQ ID NO: 49), HV1 (SEQ ID NO: 51), HV2a (SEQ ID NO: 53), HV2b (SEQ ID NO: 55), HV3 (SEQ ID NO: 57), and HV4 (SEQ ID NO: 59) are respectively shown in FIGS. 1 and 2.

(ii) Design of Gene of Variable Region of Humanized Lym2 Antibody

The base sequences which encode amino acid sequences of variable regions of a humanized antibody were designed using codons highly frequently used in animal cells. With these base sequences, construction of a humanized Lym2 antibody expression vector described below and expression of the corresponding antibody were carried out.

(2) Construction of Humanized Lym2 Antibody Expression Vector

Humanized Lym2 antibody expression vectors were constructed in the same manner as described in Example 5-(1). That is, DNA with the base sequences represented by SEQ ID NOS: 32, 34, 36, 38, 40, 42, 44, 46, 48, 50, 52, 54, 56, and 58, encoding the amino acid sequences represented by SEQ ID NOS: 33, 35, 37, 39, 41, 43, 45, 47, 49, 51, 53, 55, 57, and 59 is entirely synthesized and the corresponding VL and VH gene fragments were amplified by PCR using the primers represented by SEQ ID NOS: 28 to 31. The gene fragments were subjected to agarose gel electrophoresis and purified by QIAquick Gel Extraction Kit (QIAGEN).

The VL and VH fragments were respectively sub-cloned to a human κ constant region expression vector (BglII/BsiWI treatment) and a human heavy chain (IgG1) constant region expression vector (SalI/NheI treatment) using In-Fusion HD Cloning Kit (Clontech Laboratories, Inc.) according to the attached instructions. *E. coli* DH5α competent cells (TAKARA BIO INC.) were transformed using the prepared vector, plasmid extraction and sequence confirmation were performed to select a colony into which a correct sequence was inserted, and then a large amount of plasmids were prepared for transient expression.

(3) Transient Expression of Humanized Lym2 Antibody

Transient expression of the prepared humanized Lym2 antibody was performed using Freestyle (registered trademark) MAX CHO Expression System (Lifetechnologies Corporation) with CHO cells which are acclimated to FreeStyle (registered trademark) CHO Expression Medium (Lifetechnologies Corporation) described in Example 5-(2) as a host cell. The method of plasmid introduction was performed according to the attached instructions. The light chain expression vector and the heavy chain expression vector were used after being mixed with each other at a mixing ratio of 1:2.

The amount of culture solution was 200 mL and the cells were cultured for 5 days under set condition of 37° C. at 125 rpm in the presence of 8% $CO_2$. After culture, the cell suspension was centrifuged and allowed to pass through a filter, 0.2 μm (Thermo Scientific) to recover the culture supernatant including a humanized Lym2 antibody was recovered.

(4) Purification of Humanized Lym2 Antibody

The humanized Lym2 antibody was purified by affinity purification using MabSelect SuRe (GE Healthcare) as follows. After the resin was equilibrated with PBS, the culture supernatant obtained in (3) was loaded and washed twice with PBS.

After the washing, an antibody was eluted using an elution buffer (20 mM citric acid, 50 mM NaCl, pH 3.4) and one-tenth the total amount of a neutralization buffer (1 M phosphoric acid-NaOH, pH 7.0) was added thereto for neutralization. Next, buffer-substitution with PBS using NAP25 (GE Healthcare) was performed. The resultant was concentrated by ultrafiltration using Amicon Ultra-4 Centrifugal Filter Units (Millipore) and the absorbance at 280 nm ($A_{280}$) was measured using Nanodrop8000 (Thermo Scientific) for concentration measurement and preparation of the antibody solution.

Example 7

Antigen-Binding Activity of chLym2 and Humanized Lym2 Antibody

FLAG fusion human CRTH2-expressing 3Y1-B cells were peeled using a 0.25% trypsin-EDTA (NACALAI TESQUE, Inc.), washed with PBS, and suspended with SM. Next, the cells were seeded in a 96-well plate such that one well has $1 \times 10^5$ cells. Further, chLym2 or each of the humanized Lym2 antibodies was added at each final concentrations of 50000, 12500, 3125, 781, 195, 49, 12, and 3 ng/mL to cause a reaction at 4° C. for 60 minutes.

After the cells were washed with SM, Goat F(ab')$_2$ Anti-Human IgG PE (γchain specific) (Southern Biotech Inc.) diluted 500 times with SM was added to cause a reaction at 4° C. for 60 minutes. The cells were washed with SM and resuspended with 50 μL of SM, and the fluorescent intensity was measured by flow cytometry (BD Biosciences, FACS CantoII).

The data was analyzed by FLowJo 7.65 (Tomy Digital Biology Co., Ltd.), curve fitting of the Geomean value in each concentration was performed using a Logistic curve, and the 50% effective concentration ($EC_{50}$) value of the binding of chLym2 and each humanized Lym2 antibody and the standard error (SE) value thereof were calculated using R language (Ver. 3.02) which is a language for statistical analysis. The results are listed in Table 1.

TABLE 1

| No. | mAb | $EC_{50}$ value (μg/mL) |
|---|---|---|
| 1 | chLym2 | 0.54 ± 0.072 |
| 2 | LV0HV0 | 0.87 ± 0.052 |
| 3 | LV1HV0 | 0.69 ± 0.057 |
| 4 | LV2aHV0 | 0.66 ± 0.053 |
| 5 | LV2bHV0 | 0.67 ± 0.061 |
| 6 | LV2cHV0 | 0.68 ± 0.071 |
| 7 | LV3aHV0 | 0.70 ± 0.078 |
| 8 | LV3bHV0 | 0.81 ± 0.050 |
| 9 | LV4HV0 | 0.74 ± 0.076 |
| 10 | LV0HV4 | 0.58 ± 0.052 |
| 11 | LV1HV4 | 0.58 ± 0.045 |
| 12 | LV2aHV4 | 0.51 ± 0.068 |
| 13 | chLym2 | 0.50 ± 0.077 |
| 14 | LV2bHV4 | 0.59 ± 0.038 |
| 15 | LV2cHV4 | 0.54 ± 0.070 |
| 16 | LV3aHV4 | 0.76 ± 0.135 |
| 17 | LV3bHV4 | 0.53 ± 0.095 |
| 18 | LV4HV4 | 0.68 ± 0.116 |
| 19 | LV0HV0 | 0.55 ± 0.052 |
| 20 | LV0HV1 | 0.78 ± 0.088 |
| 21 | LV0HV2a | 0.65 ± 0.077 |
| 22 | LV0HV2b | 0.72 ± 0.064 |
| 23 | LV0HV3 | 0.69 ± 0.032 |
| 24 | LV0HV4 | 0.67 ± 0.023 |

As the result, it was suggested that various humanized antibodies have comparable human CRTH2 reactivity to the chimeric antibody as listed in Table 1.

Example 8

Eosinophils and Basophils Depletion Activity of chLym2 and Humanized Lym2 Antibody Human peripheral blood collected by adding a heparin sodium injection liquid was centrifuged at 4° C. and 1500 rpm for 30 minutes, and the plasma was recovered.

After the plasma was recovered, PBS (NACALAI TESQUE, Inc.) was added to the pellet containing the red blood up to the original volume of blood and the pellet was suspended. Next, to 1 mL of the suspension, 10 mL of hemolyzing solution [solution obtained by diluting 10×RBC Lysis buffer (eBioscience) 10 times with sterile water] was added to be mixed by inversion. The resultant was allowed to stand at room temperature for 10 minutes and centrifuged at room temperature and 1500 rpm for 5 minutes and washed twice with PBS after the supernatant was removed therefrom.

Thereafter, the cell pellet was suspended with the recovered plasma and the cells were seeded in a 48-well plate at 300 µL/well, each of chLym2, humanized Lym2 antibodies LV0HV0, LV0HV1, and LV0HV2a, or an isotype control antibody [IgG1 antibody prepared according to the method described in Example 5 using a vector encoding an anti-2, 4-dinitrophenol (DNP) IgG1 antibody described in Clin Cancer Res 2005, 11(8), 3126 to 3135 (hereinafter, referred to as anti-DNP IgG1 antibody)] were added at each final concentrations of 1000, 100, 33, 11, 3.7, 1.2, 0.4, and 0.01 ng/mL to cause a reaction in a 5% $CO_2$ incubator at 37° C. for 20 hours.

After the reaction, the cell fluid in each well was recovered, 10 mL of SM was added thereto, 200 µL per sample of CountBright Absolute Counting Beads, for flow cytometry (Molecular Probes) was added as control beads, and the fluid was centrifuged at 4° C. and 2000 rpm for 10 minutes, and then the supernatant was removed. The resultant was washed twice with SM, 10000 µg/mL of IgG from human serum (Sigma-Aldrich Co. LLC) diluted with SM was added at 300 µL/sample and suspended to cause a reaction at 4° C. for 30 minutes.

Thereafter, the cells were seeded in a 96-well plate such that each well has 40 µL of suspension and PE anti-human Siglec-8 Antibody (Biolegend Inc.), for detecting eosinophils, and PE-Cy7 Mouse Anti-Human CD123 (BD Biosciences) and Anti-Human Fc epsilon Receptor I alpha (FcεR1) APC (eBioscience), for detecting basophils, were respectively added thereto at 5 µL/well to cause a reaction at 4° C. for 40 minutes.

The cells were washed twice with SM, suspended by SM containing 1% of 7-AAD Staining Solution (BD Biosciences), allowed to stand at 4° C. for 10 minutes, and the fluorescent intensity was analyzed by flow cytometry (BD Biosciences, FACS CantoII).

Human eosinophils were detected as 7-AAD negative siglec8-PE positive fractions in granulocyte fractions of FSC-SSC deployment. Human basophils were detected as 7-AAD negative fractions, CD123-PC-Cy7 positive fractions, FcεRI-APC positive fractions in lymphocyte fractions of FSC-SSC deployment. The cell depletion activity was evaluated by analyzing the count number of each cell per a certain number of CountBright.

As the result, it was found that all evaluated humanized Lym2 antibodies LV0HV0, LV0HV1, and LV0HV2a show cytotoxic activity against eosinophils and basophils comparable to the chimeric Lym2 antibody chLym2 as shown in FIGS. 3(A) to 3(C).

Example 9

Preparation of Anti-Human CRTH2 Antibody for Control
(1) Preparation of Anti-Human CRTH2 Antibody Expression Vector for Control
The base sequences encoding the amino acid sequences of VH and VL of anti-human CRTH2 monoclonal antibodies hu19A2 v52, hu8B1 v1, mu8B1, mu3C12, and mu31A5 described in Pamphlet of International Publication No. 2014/144865 (respectively represented by SEQ ID NOS: 57 and 40, 64 and 52, 62 and 50, 63 and 51, and 65 and 53 in Pamphlet of International Publication No. 2014/144865) were entirely synthesized.

The above described base sequences were incorporated in the antibody expression vectors so that each vector have the combinations of VH and VL of each antibody according to the method described in Example 5-(1) to prepare 5 types of humanized or chimeric anti-human CRTH2 antibody (respectively, hu19A2 v52, hu8B1 v1, ch8B1, ch3C12, and ch31A5) expression vectors for control were prepared.

(2) Preparation of Anti-Human CRTH2 Antibody Transiently Expressing Cells for Control and Purification of Antibody According to the method described in Examples 5-(2) and (3), a host cell was allowed to transiently express antibody expression vectors of hu19A2 v52, hu8B1 v1, ch8B1, ch3C12, or ch31A5, and then each antibody was purified from the culture supernatant.

Example 10

Epitope Analysis of Anti-Human CRTH2 Monoclonal Antibody Using Cells which Express Mutated Human CRTH2 with Amino Acid Substitution
(1) Preparation of Mutated Human CRTH2 with Amino Acid Substitution Expression Vector A mutant with amino acid substitution expression vector obtained by partially substituting amino acid residues in an extracellular region with other amino acid residues among the amino acid sequences of human CRTH2 was prepared. Specifically, mutant with amino acid substitution expression vectors obtained by substitution of S2A; N4A; T6A and L7A; K8A, P9A, and L10A; P12A, L14A, and EI5A; Q16E, R19H, and Q21R; H23A, S24A, and N25A; T26A, S27A, and I28A; D171A, T172A, and I173A; S174A, R175A, and L176A; D177A, G178A, and R179A; I180A and M181A; Y183A, Y184A, and N185A; L187A, L188A, and L189A; N190A; P191A; G192A; P193A; D194A; R195A; D196A, and T198A; N275A, G277A, and L278A; P276A; P279A and L281A; P280A; or V282A, R283A, and R284A in the amino acid sequences represented by SEQ ID NO: 2 were respectively prepared. It should be noted that the above symbols in the amino acid substitution indicate [single letter code of an amino acid residue before substitution] [substitution position counting from the N terminal] [single letter code of the amino acid reside after substitution].

Azami-Green tag was added to the intercellular C terminal region by inserting genes encoding various mutants with amino acid substitution obtained by deleting termination codons to the restriction enzyme sites of BamHI and HindIII using phmAG1-MNLinker (MBL) as expression vectors.

The above-described vectors expressing mutants with amino acid substitution were prepared using 1) a method of entirely synthesizing gene sequences encoding mutants with amino acid substitution and inserting the gene sequences into a vector or 2) a method of performing site-specific mutation from a vector into which DNA which encodes the amino acid sequences of wild-type human CRTH2 represented by SEQ ID NO: 1 was inserted.

(2) Establishment of Mutated Human CRTH2 with Amino Acid Substitution Transiently Expressing Cells
CHO-S cells (Lifetechnologies) were used for preparing mutated human CRTH2 with amino acid substitution expressing cell lines. Free style CHO expression medium (Invitrogen) containing 8 mM L-Glutamine (Invitrogen) was used for subculturing cells and the cells were cultured by shaking under the conditions of 37° C. in the presence of 5% $CO_2$.

25 µg of the mutated human CRTH2 with amino acid substitution expression vector prepared in (1) described above was dissolved in 400 µL of Opti-Pro SFM (Invitrogen) and 25 µL of a Freestyle MAX Reagent (Invitrogen) was dissolved in 400 µL of Opti-Pro SFM and each of them were allowed to stand at room temperature for 5 minutes. The two liquids were mixed with each other and allowed to stand at room temperature for 15 minutes. The mixed solution was added to the CHO-S culture solution and the cells were cultured for 24 hours, thereby obtaining cell lines which express mutated human CRTH2 with amino acid substitution.

(3) Analysis of Reactivity of Obtained Antibody Using Cells which Express Mutated Human CRTH2 with Amino Acid Substitution The CHO-S cells which express mutated human CRTH2 with amino acid substitution established in (2) were washed with SM, seeded in a 96-well plate such that one well has $2 \times 10^5$ cells, and centrifuged at 1700 rpm for 2 minutes. After the supernatant was removed, chLym2, LV0HV1, the anti-human CRTH2 antibody hu19A2 v52, hu8B1 v1, ch3C12, or ch31A5 prepared in Example 9, or a commercially available anti-human CRTH2 antibody BM16 (Santa Cruz) prepared to have a concentration of 10 µg/mL using SM was added thereto to cause a reaction at 4° C. for 1 hour.

After the cells were washed, goat anti-Human IgG Alexa 647 (Molecular Probes) diluted with SM was added to wells to which chLym2, LV0HV1, hu19A2 v52, hu8B1 v1, ch3C12, or ch31A5 was added and goat anti-Rat IgG Alexa 647 (Molecular Probes) diluted with SM was added to wells to which BM16 was added at a final concentration of 10 µg/mL to cause a reaction at 4° C. for 1 hour.

After the reaction, the cells were washed and suspended with SM, and the fluorescent intensity was analyzed by flow cytometry (BD Biosciences, FACS CantoII). At the time of analysis, positive cells of Azami-Green were subjected to gating from the whole cells and the reactivity of each antibody to this population was analyzed.

Moreover, in order to correct the expression level between mutants, the relative fluorescent intensity was calculated by dividing the fluorescent intensity of Alexa647 resulting from the binding of each antibody by the fluorescent intensity of Azami-Green added to the C terminal region and set as the reactivity of each antibody. Then, the relative fluorescent intensity regarding the cells which express mutated human CRTH2 with amino acid substitution were analyzed for each antibody when the fluorescent intensity of each antibody with respect to the wild-type human CRTH2-expressing cells was set to 100%.

As the result, it was found that the reactivity of humanized Lym2 antibody LV0HV1 against the cells which express mutated human CRTH2 with amino acid substitution of P12A, L14A, and E15A; D177A, G178A, and R179A; I180A and M181A; Y183A, Y184A, and N185A; L187A, L188A, and L189A; G192A; D194A; R195A; or D196A and T198A was lost as shown in FIGS. 4 to 7.

In addition, it was found that the reactivity of the chimeric Lym2 antibody chLym2 against cells which express mutated human CRTH2 with amino acid substitution of D171A, T172A, and I173A was additionally lost. Since the reactivity of the humanized Lym2 antibody LV0HV1 against the cells which express mutated human CRTH2 with amino acid substitution containing D171A, T172A, and I173A was greatly decreased, it was suggested that both of LV1HV0 and chLym2 bind to the same epitope.

On the other hand, since the reactivity of other anti-human CRTH2 antibodies compared this time against cells which express mutated human CRTH2 with amino acid substitution at different site from the site in regard to the anti-human CRTH2 antibody of the present invention was significantly decreased, it was found that other existing anti-human CRTH2 antibodies recognize epitopes different from the antibodies of the present invention.

In addition, as a result of evaluating the reactivity against each cells which express mutated human CRTH2 with amino acid substitution, since the reactivity of the existing anti-human CRTH2 antibodies against cells which express mutated human CRTH2 with amino acid substitution containing G192A or D194A was not decreased and only the reactivity of the antibodies of the present invention against the cells was decreased, the anti-human CRTH2 antibody of the present invention was found to bind to an epitope comprising at least one amino acid residue of Gly192 and Asp194 of human CRTH2.

Example 11

Evaluation of Reactivity Against Human Eosinophils

To human peripheral blood collected by adding a heparin sodium injection liquid, the same amount of physiological saline for injection as the human peripheral blood was added thereto and mixed with each other. 15 mL of Ficoll-Paque PREMIUM 1.084 (GE Healthcare) was added to a 50 mL centrifuge tube, 30 mL of the above described human peripheral blood diluted with physiological saline was overlaid thereon, and centrifugation was performed at room temperature and 1500 rpm for 30 minutes.

After the centrifugation, half the amount of the plasma layer, the mononuclear cell layer, and the Ficoll layer was removed by an aspirator and the platelet adhering to a wall of the centrifuge tube was removed using sterilized swab. Thereafter, 27 mL of sterilized ice water was dispensed to each tube for hematolysis for 30 seconds.

Next, 3 mL of an ice-cold 10×PIPES buffer solution [a solution obtained by dissolving 32.15 g of sodium chloride (Wako Pure Chemical Industries), 1.85 g of potassium chloride (NACALAI TESQUE, Inc.), 38 g of PIPES (piperazine-1,4-bis(2-ethanesulfonic acid, NACALAI TESQUE, Inc.), and 8.4 g of sodium hydroxide (NACALAI TESQUE, Inc.) in 500 mL of distilled water] was added thereto to bring back to isotonicity and the resultant was centrifuged at 4° C. and 1200 rpm for 5 minutes. After the centrifugation, the supernatant was aspirated, 2 mL of 1×PIPES buffer solution [a solution obtained by diluting the 10×PIPES buffer solution 10 times with distilled water] was added, and then the cell pellet was loosened.

The hematolysis operation was repeated again and the obtained cell pellet was washed twice with a solution obtained by adding a MACS BSA Stock Solution (Miltenyi Biotec) to an autoMACS Rinsing Solution (Miltenyi Biotec) (hereinafter, abbreviated as a MACS buffer).

After the number of cells was counted, eosinophils were isolated by a negative selection method using CD16 MicroBeads, human (Miltenyi Biotec) according to the attached instructions.

The isolated cells were washed with SM, seeded in a 96-well plate such that one well has $1 \times 10^5$ cells, and centrifuged at 2000 rpm for 2 minutes. After the supernatant was removed, Lym2 antibody and commercially available CRTH2 antibody BM16 (Santa Cruz), or 301108 (R&D)

which were diluted with SM, were added at each final concentrations of 10, 3.3, 1.1, 0.37, and 0.12 μg/mL to cause a reaction at 4° C. for 1 hour.

After the cells were washed, CELL LAB Mouse Anti-Rat Kappa (kappa light chain specific) FITC (Beckman Coulter Inc.) diluted with SM was added to wells to which Lym2 antibody or BM16 was added and CELL LAB Goat Anti-Mouse IgG (γ chain specific) Fluorescein (FITC) Conjugate (Beckman Coulter Inc.) diluted with SM was added to wells to which 301108 was added at a final concentration of 10 μg/mL respectively to cause a reaction at 4° C. for 1 hour. The cells were washed again and suspended with SM, and the fluorescent intensity was analyzed by flow cytometry (BD Biosciences, FACS CantoII).

As the result, it was found that the rat anti-human CRTH2 antibody Lym2 exhibits stronger reactivity against human eosinophils than commercially available rat anti-human CRTH2 antibody BM16 and mouse anti-human CRTH2 antibody 301108 (FIG. 8).

Example 12

Reactivity of chLym2 Against Human Basophils

To human peripheral blood collected by adding a heparin sodium injection liquid, the same amount of physiological saline for injection as the human peripheral blood was added and mixed with each other. 15 mL of Ficoll-Paque PREMIUM 1.084 (GE Healthcare) was added to a 50 mL centrifuge tube, 30 mL of the human peripheral blood diluted with physiological saline was overlaid thereon, and centrifugation was performed at room temperature and 1500 rpm for 30 minutes.

After the centrifugation, the mononuclear cell layer was recovered using a pipette and washed twice with an MACS buffer. After the number of cells was counted, basophils were isolated by a negative selection method using Basophil Isolation Kit II, human (Miltenyi Biotec) according to the attached instructions.

After the isolated cells were washed with SM, the isolated cells were seeded in a 96-well plate such that one well has $5 \times 10^4$ cells, and centrifuged at 2000 rpm for 2 minutes. After the supernatant was removed, the cells were suspended with 100 μL of SM, and chLym2 or the isotype control antibody described in Example 8 labeled using Zenon Alexa Fluor 647 Human IgG Labeling Kit (Molecular Probes) according to the attached instructions were added at a final concentration of 10 μg/mL to cause a reaction at 4° C. for 1 hour. After the cells were washed, the cells were suspended with SM, and the fluorescent intensity was analyzed by flow cytometry (BD Biosciences, FACS CantoII).

As the result, it was found that chLym2 has reactivity against human basophils (FIG. 9). Accordingly, it was found that the chimeric anti-human CRTH2 antibody chLym2 of the present invention binds to basophils.

Example 13

Reactivity of Humanized Lym2 Antibody Against Human CD4-Positive T-Cells

In the same manner as in Example 12, a cell suspension of a mononuclear cell layer prepared using Ficoll-Paque PREMIUM (GE Healthcare) in place of Ficoll-Paque PREMIUM 1.084 was seeded in a 96-well plate at 100 μL/well, and humanized Lym2 antibody LV0HV1 which was biotin-labeled using EZ-Link Sulfo-NHS-LC-Biotin according to the attached instructions was added, No-Weigh Format (PIERCE) at a final concentration of 10 μg/mL to cause a reaction at 4° C. for 1 hour.

After the cells were washed, streptavidin Alexa Fluor 647 conjugate (Molecular Probes) diluted with SM at a final concentration of 10 μg/mL and FITC anti-human CD3 Antibody (Biolegend Inc.) and CD4 Antibody, Clone SK3, PE-Conjugated (stem cell technology) in the amount described in the attached instructions were added thereto to cause a reaction at 4° C. for 1 hour.

After the cells were washed again, the cells were suspended by SM, and the fluorescent intensity was analyzed by flow cytometry (BD Biosciences, FACS CantoII). Analysis was carried out by showing the fluorescent intensity of fluorescent staining resulting from humanized Lym2 antibody LV0HV1 on the vertical axis and the fluorescent intensity of fluorescent staining resulting from the CD4 antibody on the horizontal axis with respect to a cell group fractionated lymphocytes using FSC-SSC deployment and fractionated by CD3 positive cells and CD4 positive cells. In this manner, the percentage of fractions in the CD3-positive CD4-positive cells to which the humanized Lym2 antibody LV0HV1 reacted was calculated. As the result, humanized Lym2 antibody LV0HV1 reacted to approximately 2% to 3% of T cell fractions of the CD3-positive CD4-positive cells (FIG. 10).

Example 14

Cytotoxic Activity Against Eosinophils and Basophils

A cell suspension prepared in the same manner as in Example 8 was seeded in a 96-well plate at 95 μL/well, test antibodies were added thereto at each of final concentrations of 1000, 10, 3, 1, 0.3, and 0.1 ng/mL to cause a reaction in a 5% $CO_2$ incubator at 37° C. for 20 hours. As the test antibodies, humanized Lym2 antibody LV0HV1, and the anti-human CRTH2 antibody hu19A2 v52, hu8B1 v1, ch3C12, and ch31A5 prepared in Example 9 were used. The anti-DNP IgG1 antibody was used as an isotype control antibody.

100 μL of SM was respectively added to each well after the reaction, 20 μL of CountBright Absolute Counting Beads, for flow cytometry (Molecular Probes) was added to each well as control beads, and the resultant was centrifuged at 4° C. and 2000 rpm for 2 minutes, and then the supernatant was removed. The resultant was washed twice with SM, 10000 μg/mL of IgG from human serum (Sigma-Aldrich Co. LLC) diluted with SM was added at 100 μL/well to cause a reaction at 4° C. for 30 minutes. The rest was carried out in the same manner as in Example 8.

As the result, both eosinophils and basophils were removed by the humanized anti-human CRTH2 antibody LV0HV1 in an antibody concentration-dependent manner. In a case of existing anti-human CRTH2 antibody ch3C12, the activity of removing the cells was weaker than the activity of humanized anti-human CRTH2 antibody LV0HV1 [FIGS. 11(A) and 11(B)]. Therefore, it is suggested that the anti-human CRTH2 antibody of the present invention can exhibit therapeutic effects targeting eosinophils or basophils which express CRTH2.

Example 15

Cytotoxic Activity Against Th2 Cells

The mononuclear cell layer prepared in the same manner as in Example 13 was washed twice with RPMI-1640 (Wako Pure Chemical Industries) to which 1/10 volume FBS (GIBCO Inc.), 200 mM-L-Glutamine Stock Solution (NACALAI TESQUE, Inc.), 10 mM MEM Non-Essential Amino Acids Solution (GIBCO Inc.), 100 mM Sodium Pyruvate (GIBCO Inc.), 1 M HEPES Buffer Solution (GIBCO Inc.), and 1/100 volume Penicillin-Streptomycin, Liquid (GIBCO Inc.) were added [hereinafter, referred to as peripheral blood mononuclear cell (PBMC) culture medium], thereby preparing a $1 \times 10^7$ cells/mL cell suspension.

The prepared cell suspension was seeded in a 96-well plate at 100 μL/well, chLym2 antibody, the humanized anti-human CRTH2 antibody LV0HV1 or the isotype control antibody described in Example 8 was added thereto at a final concentration of 10 μg/mL to cause a reaction in a 5% $CO_2$ incubator at 37° C. for 20 hours.

The cells after the reaction were washed 7 times with a PBMC culture medium to remove the test antibodies thoroughly. Thereafter, the cells were suspended with 100 μL of PBMC culture medium and seeded in a plate in which anti-CD3 antibody OKT3 (Abcam plc.) was immobilized at a concentration of 1 μg/mL. Next, an anti-CD28 antibody (BD Biosciences) prepared to have a concentration of 2 μg/mL was added thereto at 100 μL/well to cause a reaction in a 5% $CO_2$ incubator at 37° C. for 3 days.

The supernatant after the reaction was recovered, and cytokine in the supernatant was quantified using Human IFN-γ Flex Set (BD Biosciences), Human IL-5 Flex Set (BD Biosciences), and Human IL-13 Flex Set (BD Biosciences) according to the attached instructions.

As the result, production of IL-5 and IL-13 which are Th2 cytokine was reduced by the chimeric anti-human CRTH2 antibody chLym2 and the humanized anti-human CRTH2 antibody LV0HV1, but production of IFN-γ which is Th1 cytokine was not changed. In other words, it was suggested that the antibodies of the present invention selectively remove Th2 cells [FIGS. 12(A) and 12(B)]. Therefore, it was suggested that the anti-human CRTH2 antibody of the present invention was able to exhibit therapeutic effects targeting the Th2 cells.

Example 16

Evaluation of Reactivity in Presence of Ligand (293 EBNA)

Human CRTH2-expressing 293 EBNA cells were established by introducing the human CRTH2 gene expression pAMoh vector prepared in Example 1-(1)-(ii) into 293 EBNA cells (Invitrogen) using Fugene 6 (Promega Corporation) and selecting drug-resistant cells by culture medium formed of 10% FBS, 0.25 mg/mL of G418 (NACALAI TESQUE, Inc.), 100 μg/mL of penicillin, 100 U/mL of streptomycin (NACALAI TESQUE, Inc.), and 300 μg/mL of hygromycin B (Wako Pure Chemical Industries) in DMEM.

The human CRTH2-expressing 293 EBNA cells were peeled using 0.02% EDTA solution (NACALAI TESQUE, Inc.), washed with PBS, and suspended with the above-described culture medium. Next, the cells were seeded in a 96-well plate at $1 \times 10^5$ cells/90 μL/well and DKPGD2 (Cayman Chemical) was added thereto at a final concentration of 10 μM.

After the plate was allowed to stand in a 5% $CO_2$ incubator at 37° C. for 15 minutes, the humanized Lym2 antibody LV0HV1, the known anti-human CRTH2 antibody hu19A2 v52, hu8B1 v1, ch3C12, ch31A5, BM16 (Santa Cruz), or 301108 (R&D) at each of final concentrations of 0.3, 1, and 3 μg/mL were added thereto to cause a reaction at room temperature for 30 minutes.

After the cells were washed 5 times with SM, 10 μg/mL of goat anti-Human IgG Alexa 647 (Molecular Probes) diluted with SM was added to wells to which LV0HV1, hu19A2 v52, hu8B1 v1, ch3C12, or ch31A5 was added, 10 μg/mL of goat anti-Rat IgG Alexa 647 (Molecular Probes) diluted with SM was added to wells to which BM16 was added, and 10 μg/mL of goat anti-Mouse IgG Alexa 647 (Molecular Probes) diluted with SM was added to wells to which 301108 was added at a final concentration of 10 μg/mL to cause a reaction at 4° C. for 40 minutes. After the cells were washed again, the cells were suspended with SM, and the fluorescent intensity was analyzed by flow cytometry (BD Biosciences, FACS CantoII).

As the result, in a case of existing anti-human CRTH2 antibodies, binding to human CRTH2-expressing cells decreased in the presence of DKPGD2 which is a human CRTH2 ligand as shown in FIGS. 13(A) to (C). On the other hand, in a case of the humanized Lym2 antibody LV0HV1, binding to the human CRTH2-expressing cells was almost not decreased even at any of the antibody concentrations examined.

That is, it was found that the antibodies of the present invention exhibit high reactivity even in the presence of high concentration of the ligand. Therefore, the anti-human CRTH2 antibody of the present invention can bind to the human CRTH2-expressing cells even in the presence of a ligand with the reactivity comparable to the reactivity in the absence of a ligand and this suggests that the anti-human CRTH2 antibody of the present invention is a useful antibody which can act on the human CRTH2-expressing cells.

Example 17

Analysis of Reactivity Against Differentiation-Induced Human Mast Cells

Mast cells were prepared according to the method described in Nature Protocols 2006, 1(4), 2178 to 2183. The mast cells after 11 weeks from the start of differentiation induction were washed with SM and seeded in a 96-well plate such that each well had $5 \times 10^4$ cells, and PE anti-human CD203c (E-NPP3) Antibody (Biolegend Inc.), Brilliant Violet 421 (trademark) anti-human CD117 (c-kit) Antibody (Biolegend Inc.), and Anti-Human Fc epsilon Receptor I alpha (FcεR1) PE (eBioscience) were added thereto to cause a reaction at 4° C. for 1 hour. After the cells were washed again, the cells were suspended with SM, and the fluorescent intensity was analyzed by flow cytometry (BD Biosciences, FACS CantoII).

As the result, it was confirmed that the differentiation-induced mast cells expressed all of CD203c, CD117, and FcεRI which are mast cell surface markers.

Human IgE obtained by recombining a constant region of the anti-DNP IgG1 antibody with IgE type was added to the mast cell culture solution after 15 weeks from the start of differentiation induction at a final concentration of 10 μg/mL to cause a reaction in a 5% $CO_2$ incubator at 37° C. for 3 days.

The mast cells after the reaction were washed twice with IMDM (GIBCO Inc.) to which 100 μg/mL of penicillin, 100 U/mL of streptomycin (NACALAI TESQUE, Inc.), and 55 μM β-ME (GIBCO Inc.) were added (hereinafter, abbreviated as a basic culture medium) and suspended with 4 mL of basic culture medium, and rabbit polyclonal anti human IgE antibody (Dako) at a final concentration of 10 μg/mL was added thereto, and then the suspension was allowed to rotate using MACS mix tube rotator (Miltenyi Biotec) to cause a reaction in a 5% $CO_2$ incubator at 37° C. for 1 hour.

The cells after the reaction were washed twice with SM, seeded in a 96-well plate such that each well had $5\times10^4$ cells, and centrifuged at 2000 rpm for 2 minutes. The supernatant was removed, 10000 μg/mL of IgG from human serum (Sigma-Aldrich Co. LLC) diluted with SM was added at 100 μL/well to cause a reaction at 4° C. for 30 minutes, and humanized anti-human CRTH2 antibody LV0HV1, anti-human CRTH2 antibody hu19A2 v52, ch8B1, ch3C12, or ch31A5, each of which was biotin-labeled using EZ-Link Sulfo-NHS-LC-Biotin, No-Weigh Format (PIERCE) according to the attached instructions, or non-labeled commercially available anti-human CRTH2 antibody BM16 (Santa Cruz Biotechnology), or 301108 (R&D) was added thereto at a final concentration of 10 μg/mL to cause a reaction at 4° C. for 1 hour.

It should be noted that Purified Rat IgG2a, κ Isotype Ctrl Antibody (BioLegend Inc.) was used for BM16, Negative Control Mouse IgG2a (Dako) was used for 301108, and the anti-DNP IgG1 antibody was used for other antibodies, as isotype control antibodies.

After the cells were washed, streptavidin, Alexa Fluor 647 conjugate (Molecular Probes) diluted with SM was added to wells to which biotin-labeled LV0HV1, hu19A2 v52, ch8B1 v1, ch3C12, or ch31A5 was added, goat anti-Rat IgG Alexa 647 (Molecular Probes) diluted with SM was added to wells to which BM16 was added, and goat anti-Mouse IgG Alexa 647 (Molecular Probes) diluted with SM was added to wells to which 301108 was added at a final concentration of 10 μg/mL to cause a reaction at 4° C. for 40 minutes. After the cells were washed again, the cells were suspended with SM, and the fluorescent intensity was analyzed by flow cytometry (BD Biosciences, FACS CantoII).

As the result, as shown in FIG. 14, hu19A2 v52 exhibited reactivity against mast cells, but antibodies other than hu19A2 v52 (including LV0HV1) did not exhibit reactivity.

Example 18

Analysis of Reactivity Against Differentiation-Induced Th1

(1) Separation of Naive T Cells from PBMC

Healthy person-derived frozen PBMC (Allcells, LLC.) was washed once with 20 mL of PBMC culture medium containing 50 μL of DNase I recombinant, RNase-free (Roche Diagnostics K.K.), suspended with 20 mL of PBMC culture medium containing 50 μL of DNase I recombinant, RNase-free, and allowed to stand in a 5% $CO_2$ incubator at 37° C. for 2 hours.

Thereafter, the cells were washed twice with the MACS buffer described in Example 11 and naive CD4-positive T-cells were isolated by a negative selection method using Naive CD4+ T Cell Isolation Kit II human (Miltenyi Biotec) according to the attached instructions. The negative selection was performed twice in order to improve purity of the naive CD4-positive T-cells.

(2) Differentiation of Th1 Cells from Naive CD4-Positive T-Cells

According to the method described in J Immunol, 2002. 169(5): p. 2498 to 2506, the naive CD4-positive T-cells separated were suspended with RPMI1640 (GIBCO Inc.) to which 10% FBS (GIBCO Inc.) and 2 mM glutamic acid (NACALAI TESQUE, Inc.) were added (hereinafter, abbreviated as a culture medium) at $1\times10^6$ cells/mL and seeded in a plate in which anti-CD3 antibody OKT3 (Abeam plc.) was immobilized at a concentration of 1 μg/mL, and anti-CD28 antibody (BD Biosciences) at a final concentration of 2 μg/mL, recombinant human IL-12 (PeproTech Inc.) at a final concentration of 100 ng/mL, recombinant human IL-2 (PeproTech Inc.) at a final concentration of 10 ng/mL, and anti-IL-4 antibody (BD Biosciences) at a final concentration of 5 μg/mL were added thereto to cause a reaction in a 5% $CO_2$ incubator at 37° C. for 4 days as a stimulation process.

Thereafter, the cells were recovered, the supernatant was removed by centrifugation, and as a growth process, the cells were suspended with of culture medium up to $1\times10^6$ cells/mL, and then recombinant human IL-12 (PeproTech Inc.) at a final concentration of 100 ng/mL, recombinant human IL-2 (PeproTech Inc.) at a final concentration of 10 ng/mL, and an anti-IL-4 antibody (BD Biosciences) at a final concentration of 5 μg/mL were added thereto to cause a reaction in a 5% $CO_2$ incubator at 37° C. for 3 days.

The differentiation-induced Th1 cells were established by repeating the stimulation process and the growth process three times.

(3) Analysis of Cytokine Production from Differentiation-Induced Th1 Cells

Phorbol 12-myristate 13-acetate (Sigma-Aldrich Co. LLC) at a final concentration of 20 ng/mL, Ionomycin calcium salt from *Streptomyces* (Sigma-Aldrich Co. LLC) at a final concentration of 1 μg/mL, and Brefeldin A from *Penicillium brefeldianum* (Sigma-Aldrich Co. LLC) at a final concentration of 10 μg/mL were added to the culture solution containing differentiation-induced Th1 cell prepared in (2) to cause a reaction in a 5% $CO_2$ incubator at 37° C. for 6 hours. Thereafter, the cells were seeded in a 96-well plate at $2\times10^5$ cells/well and washed with PBS (NACALAI TESQUE, Inc.).

Next, the dead cells were stained using LIVE/DEAD Fixable Aqua Dead Cell Stain Kit, for 405 nm excitation (Molecular Probes) according to the attached instructions and washed twice with PBS, the supernatant was removed and a reaction using a Fixation Buffer (BD Biosciences) was performed at 4° C. for 45 minutes.

After the reaction, the cells were washed once with PBS and twice with 1× Perm/Wash buffer (BD Biosciences), and 2.5 μL of a PEanti-human IFN-γ Antibody (Biolegend Inc.), 5 μL of an APC anti-human IL-4 Antibody (Biolegend Inc.), 10 μL of anti-IL-5 antibodies APC (Miltenyi Biotec), and 20 μL of an APC anti-human IL-13 Antibody (Biolegend Inc.) were added thereto to cause a reaction at 4° C. for 30 minutes.

Thereafter, the cells were washed twice with 1× Perm/Wash buffer and suspended with SM, and the fluorescent intensity was analyzed by flow cytometry (BD Biosciences, FACS CantoII).

As the result, it was confirmed that the differentiation-induced Th1 was a cell population in which IL-4/5/13 was negative and 90% thereof was IFNγ positive and it produced Th1 cytokine selectively.

(4) Analysis of Reactivity of Anti-Human CRTH2 Antibody Against Differentiation-Induced Th1 Cells The differentiation-induced Th1 cells established in (2) were washed with SM, seeded in a 96-well plate such that one well has $5\times10^4$ cells, and centrifuged at 2000 rpm for 2 minutes. After the supernatant was removed, the rat anti-human CRTH2 antibody Lym2, a known anti-human CRTH2 antibody BM16 (Santa Cruz Biotechnology), or 301108 (R&D), each of which were diluted with SM, was added thereto at 10 μg/mL to cause a reaction at 4° C. for 1 hour.

Rat IgG2b, kappa monoclonal [RTK4530]-BSA/Azide free (Abcam plc.) was used for Lym2, Purified Rat IgG2a, κ Isotype Ctrl Antibody (BioLegend Inc.) was used for BM16, and Negative Control Mouse IgG2a (Dako) was used for 301108, as isotype control antibodies.

After the cells were washed, 10 µg/mL of CELL LAB Mouse Anti-Rat Kappa (kappa light chain specific) FITC (Beckman Coulter Inc.) diluted with SM was added to wells to which Lym2 antibody or BM16 was added, 10 µg/mL of CELL LAB Goat Anti-Mouse IgG (γ chain specific) Fluorescein (FITC) Conjugate (Beckman Coulter Inc.) diluted with SM was added to wells to which 301108 was added at a final concentration of 10 µg/mL to cause a reaction at 4° C. for 1 hour. After the cells were washed again, the cells were suspended with SM, and the fluorescent intensity was analyzed by flow cytometry (BD Biosciences, FACS CantoII).

As the result, the rat anti-human CRTH2 antibody Lym2 and the commercially available rat anti-human CRTH2 antibody BM16 did not exhibit reactivity against the differentiation-induced Th1 as shown in FIG. 15. On the other hand, the commercially available mouse anti-human CRTH2 antibody 301108 exhibited reactivity against the differentiation-induced Th1.

Therefore, it was found that the anti-human CRTH2 antibody of the present invention reacts against eosinophils, basophils, and Th2 cells, but it doesn't react against Th1 cells. Further, it was found that 301108 non-specifically exhibited reactivity against cells other than the CRTH2-expressing cells.

Example 19

Evaluation of Antagonist Activity of Lym2 Antibody Using Shape Change of Human Eosinophils as Index Eosinophils were separated from human peripheral blood in the same manner as in Example 11. The isolated human eosinophils were suspended with Dulbecco's phosphate buffered saline (hereinafter, referred to as D-PBS (−)) (NACALAI TESQUE, Inc.) and performed a reaction in a 5% $CO_2$ incubator at 37° C. for 1 hour and 30 minutes. Thereafter, the cells were seeded in a 96-well plate at $2\times10^5$ cells/well using 10% FBS-containing RPMI1640. Next, an isotype control antibody [CELL LAB Rat IgG2b Isotype Control (Beckman Coulter Inc.)] at a final concentration of 10 µg/mL or Lym2 antibody; or small molecular CRTH2 antagonist 00000459 (Cayman Chemical) at a final concentration of 10 µM as a positive control, was added thereto to cause a reaction in a 5% $CO_2$ incubator at 37° C. for 30 minutes.

Next, DKPGD2 (Cayman Chemical) at each of final concentrations of 0.1, 1, 10, 100, and 1000 nM was added thereto to cause a reaction in a 5% $CO_2$ incubator at 37° C. for 60 minutes. After the reaction, the cells were washed twice with ice-cold PBS, Fixation Buffer (BD Biosciences) was added at 200 µL/well, and the resultant was suspended well and allowed to stand at 4° C. for 30 minutes. After that, the cells were washed twice with SM, and shape change of eosinophils was analyzed by flow cytometry (BD Biosciences, FACS CantoII).

The shape change of eosinophils was analyzed based on an increase in Forward Scatter Light (FSC) plot which is an index of the cell size, the cell surface area, or the cell diameter in the analysis using flow cytometry and the percentage (%) of eosinophils detected in the gate of high FSC was calculated based on the FSC of DKPGD2-untreated eosinophils.

As the result, human CRTH2 ligand DKPGD2 induced shape change of eosinophils in a concentration-dependent manner as shown in FIG. 16, but small molecular CRTH2 antagonist OC000459 inhibited DKPG2-dependent shape change of eosinophils. On the other hand, both of the anti-human CRTH2 antibody Lym2 of the present invention and the isotype control antibody didn't inhibit DKPGD2-dependent shape change of eosinophils. That is, it was suggested that the anti-human CRTH2 antibody of the present invention does not have antagonist activity.

Example 20

Evaluation of Agonist Activity of Lym2 Antibody Using Shape Change of Human Eosinophils as Index In the same experimental system as in Example 19 described above, rat anti-human CRTH2 antibody Lym2 at each final concentration of 0, 0.01, 0.1, 1, and 10 µg/mL was added and a reaction was performed for 1 hour and shape change of eosinophils was analyzed.

As the result, it was shown that Lym2 antibody doesn't cause the shape change of eosinophils at a concentration of 0 to 10 µg/mL as shown in FIG. 17. That is, it was suggested that the anti-human CRTH2 antibody of the present invention does not have agonist activity.

Example 21

Evaluation of Agonist Activity and Antagonist Activity, and Ligand-Induced Signal Enhancing Activity of Anti-Human CRTH2 Antibody Using Shape Change of Human Eosinophils as Index Eosinophils were separated from human peripheral blood in the same manner as in Example 11. In this case, the step of adding the same amount of physiological saline for injection as the blood to the blood was omitted and the eosinophils were directly overlaid on Ficoll-Paque PREMIUM 1.084 (GE Healthcare). The isolated human eosinophils were suspended with D-PBS (−) (NACALAI TESQUE, Inc.) and a reaction was performed in a 5% $CO_2$ incubator at 37° C. for 1 hour and 30 minutes.

Thereafter, the cells were seeded in a 96-well plate at $0.7\times10^5$ cells/well using 10% FBS-containing RPMI1640. Next, an isotype control antibody, the humanized Lym2 antibody LV0HV1, the anti-human CRTH2 antibody hu19A2 v52, ch8B1, ch3C12, or ch31A5 prepared in Example 9, or the commercially available anti-human CRTH2 antibody BM16 (Santa Cruz Biotechnology), or 301108 (R&D) was added thereto at a final concentration of 10 µg/mL to cause a reaction in a 5% $CO_2$ incubator at 37° C. for 30 minutes.

It should be noted that Purified Rat IgG2a, κ Isotype Ctrl Antibody (BioLegend Inc.) was used for BM16, Negative Control Mouse IgG2a (Dako) was used for 301108, and the anti-DNP IgG1 antibody was used for other antibodies, as isotype control antibodies.

Next, RPMI1640 containing either DKPGD2 (Cayman Chemical) or 10% FBS—was added thereto at a final concentration of 100 nM to cause a reaction in a 5% $CO_2$ incubator at 37° C. for 60 minutes. After the reaction, the cells were washed twice with ice-cold PBS, Fixation Buffer (BD Biosciences) was added at 100 µL/well, and the resultant was suspended well and allowed to stand at 4° C. for 30 minutes. The cells were washed twice with SM, and the shape change of eosinophils was analyzed in the same manner as in Example 19.

As the result, a tendency of slight shape change was observed in the case of hu19A2 v52 in regard to shape change caused by the treatment of the anti-human CRTH2 antibody in the absence of a ligand as shown in FIGS. 18(A)

to 18(C). However, there were no antibody which caused strong shape change and it is suggested that all antibodies do not have agonist activity.

Further, in regard to shape change caused by the treatment of anti-human CRTH2 antibody under the conditions of DKPGD2 treatment, since shape change induced by DKPGD2 was suppressed by the treatment of ch8B1, ch3C12, and ch31A5, it was suggested that these antibodies have antagonist activity. These results are consistent with the findings of the prior patent document (Pamphlet of International Publication No. 2014/144865).

On the other hand, hu19A2 v52 and BM16 enhanced the shape change induced by DKPGD2. Particularly, it was found that hu19A2 v52 enhanced the shape change induced by 100 nM of DKPGD2 up to approximately twice.

As described above, since shape change is not induced by hu19A2 v52 and BM16 antibody in the absence of the ligand, it was suggested that these antibodies have signal-enhancing activity wherein the signal is caused by DKPGD2 which is a CRTH2 ligand.

On the other hand, since LV0HV1 and 301108 do not affect shape change under the both conditions of presence and absence of DKPGD2 as similar to the isotype control antibody, it was suggested that LV0HV1 and 301108 do not have signal enhancing activity wherein the signal is caused by DKPGD2.

The anti-human CRTH2 antibody of the present invention is preferable in that it does not block or enhance a physiological signal.

Example 22

Evaluation of Reactivity of CRTH2 Monoclonal Antibody with Respect to Conformation Change Accompanied by Transition of CRTH2 Activation State (1) Preparation of Horseradish Peroxidase (HRP)-Labeled Antibody Humanized Lym2 antibody LV0HV1 and hu19A2 v52 were directly labeled with HRP using Peroxidase Labeling Kit-NH2 (Dojindo Molecular Technologies, Inc.) according to the attached document and diluted to 1 mg/mL with D-PBS (−) (NACALAI TESQUE, Inc.).

(2) Preparation of Membrane Fractions of Human CRTH2-Expressing Cells

The human CRTH2-expressing CHO/DG44 cells established in Example 1 were peeled using 0.02% EDTA solution (NACALAI TESQUE, Inc.) and the cells were washed with D-PBS (−) cooled to 4° C. The membrane fractions were prepared using Minute Plasma Membrane Protein Isolation Kit (Invent Biotechnologies) according to the attached document.

(3) Evaluation of Reactivity of Anti-Human CRTH2 Antibody Against Membrane Fractions of Human CRTH2-Expressing Cells 50 mM Tris-HCl buffer pH 7.4 (NACALAI TESQUE, Inc.) to which 50 mM HEPES (GIBCO Inc.), 5 mM $MgCl_2$ (NACALAI TESQUE, Inc.), 100 mM NaCl (NACALAI TESQUE, Inc.), and 1 mM EDTA (Invitrogen) were added (hereinafter, referred to as an ELISA reaction solution) was added to the membrane fractions prepared in (2) to have a concentration of 1 mg/mL, and the mixture was added to PROTEOSAVE 1.5 mL Microtubes (Sumitomo Bakelite Co., Ltd.) at 50 μL/tube.

Next, an ELISA reaction solution to which 500 μM GTPγS (Roche Diagnostics K.K.) or 500 μM GDP (Sigma-Aldrich Co. LLC) was added was added to the microtubes at 50 μL/tube for incubation at 30° C. for 1 hour.

Subsequently, IgG from human serum (Sigma-Aldrich Co. LLC) diluted to 10 mg/mL with D-PBS (−) and 30% w/v BSA-PBS fatty acid free (Wako) were respectively added to the microtubes at 50 μL/tube for incubation at 30° C. for 30 minutes.

Next, HRP-labeled LV0HV1 or hu19A2 v52 prepared in (1) described above was diluted to 5 μg/mL with the ELISA reaction solution and added to the microtubes at 50 μL/tube for incubation at 30° C. for 1 hour. In this manner, the antibody reaction against membrane fractions was carried out. The supernatant was removed after centrifugation at 4° C. for 30 minutes at 16000 g.

Thereafter, an ELISA reaction solution to which 100 μM GTPγS was added was added to tubes to which GTPγS was originally added and an ELISA reaction solution to which 100 μM GDP was added was added to tubes to which GDP was originally added respectively by 1 mL/tube. The supernatant was removed after centrifugation at 4° C. for 30 minutes at 16000 g again. After the same procedure was repeated four times, D-PBS (−) was added at 100 μL/tube and membrane fractions were sufficiently suspended.

The suspension was added to a 96-well plate at 30 μL/well, and 1-Step Ultra TMB-ELISA reagent (Thermo Scientific) was added to 96-well plate at 100 μL/well. After the reaction at room temperature for 10 minutes, 0.5 mol/L of sulfuric acid (Wako) was added by 100 μL/well to stop the reaction.

The absorbance at 480 nm was measured by SPECTRA max 340PC and the obtained result was analyzed using Graphpad Prism (ver. 6.05). Further, Turkey's multiple comparisons test was adapted and performed together with a significance difference test.

As the result, the reactivity of hu19A2 v52 with respect to membrane fractions at the time of GDP treatment was significantly decreased compared to when GTPγS treatment was carried out (P<0.0001) as shown in FIG. 19. On the other hand, the reactivity of LV0HV1 was not changed at the time of GTPγS treatment or GDP treatment (p>0.1).

It is known that CRTH2 is a GPCR and in general, GTP binds to GPCR in the activated conformation and GDP binds to GPCR in the inactivated conformation. As shown from the results described above, since the reactivity of the anti-human CRTH2 antibody of the present invention against CRTH2 was not changed regardless of the presence or absence of the treatment of GTPγS which is GTP analog or GDP, the possibility was suggested that the anti-human CRTH2 antibody is not affected by the conformation change accompanied by activation of CRTH2 and exhibits constant reactivity.

Example 23

Preparation of Azami-Green Fusion Human and Cynomolgus Monkey CRTH2 Expression phmAG1-MNLinker Vectors (1) Preparation of Azami-Green Fusion Human CRTH2 Expression phmAG1-MNLinker Vector The target fragment was amplified by PCR using primer human CRTH2 azami-A (SEQ ID NO: 60) and human CRTH2 azami-B (SEQ ID NO: 61) from the human CRTH2 gene expression pAMoh prepared in (1)-(ii) of Example 1 and was connected to a vector phmAG1-MNLinker (MBL) using restriction enzymes BamHI and HindIII, thereby constructing an Azami-Green fusion human CRTH2 expression phmAG1-MNLinker vector.

(2) Preparation of Azami-Green Fusion Cynomolgus Monkey CRTH2 Expression phmAG1-MNLinker Vector An azami-Green fusion cynomolgus monkey CRTH2 expression phmAG1-MNLinker vector was constructed in the same manner as in (1) using primer cyno CRTH2 azami-A (SEQ ID NO: 64) and cyno CRTH2 azami-B (SEQ ID NO: 65) from the cynomolgus monkey CRTH2 expression pMoh vector constructed in the same manner as in (1)-(ii) of Example 1 using cDNA of cynomolgus monkey CRTH2 which was entirely synthesized (cDNA sequence: SEQ ID NO: 62 and amino acid sequence: SEQ ID NO: 63).

Example 24

Establishment of Azami-Green Fusion Human CRTH2-Expressing CHO/DG44 Cells and Cynomolgus Monkey CRTH2-Expressing CHO/DG44 Cells The human and cynomolgus monkey CRTH2 expression phmAG1-MNLinker vectors prepared in Example 23 was cleaved by restriction enzyme BsaI treatment and then the obtained linear DNA was purified and dissolved in sterile water. This DNA was introduced to CHO/DG44 cells by an electroporation method and cultured in IMDM culture medium for 3 days.

Thereafter, drug-resistant cells were selected by the IMDM selected medium to which 0.5 mg/mL G418 (NACALAI TESQUE, Inc.) was added. The selected drug-resistant cells were peeled using a 0.25% Trypsin-EDTA (NACALAI TESQUE, Inc.), washed with PBS, and suspended by the IMDM selected medium. Subsequently, cell populations showing Azami-Green fluorescent intensities similar to each other were gated from the human CRTH2-expressing cells and cynomolgus monkey CRTH2-expressing cells using Cell Sorter SH800 (Sony), sorted out by 1 cell/well, and expansively cultured, to establish Azami-Green fusion human CRTH2-expressing CHO/DG44 cells and cynomolgus monkey CRTH2-expressing CHO/DG44 cells.

In regard to Azami-Green fusion human CRTH2-expressing CHO/DG44 cells and cynomolgus monkey CRTH2-expressing CHO/DG44 cells, cells were prepared in the same manner as described above and Azami-Green expression was confirmed using flow cytometry (BD Biosciences, FACS CantoII). As the result, it was confirmed that the level of Azami-Green expression was the same in each cells as shown in FIG. 20.

Example 25

Evaluation of Binding Activity of Humanized Lym2 Antibody LV0HV1 Against Human or Cynomolgus Monkey CRTH2

The Azami-Green fusion human CRTH2-expressing CHO/DG44 cells and the cynomolgus monkey CRTH2-expressing CHO/DG44 cells established in Example 24 were peeled using 0.02% EDTA solution (NACALAI TESQUE, Inc.), washed with PBS, and suspended with SM. Next, the cells were seeded in a 96-well plate such that each well had $2 \times 10^5$ cells, and humanized Lym2 antibody LV0HV1 or the anti-DNP IgG1 antibody at each of final concentrations 30000, 7500, 1875, 469, 117, 29, 7, and 2 ng/mL were added thereto to cause a reaction at 4° C. for 40 minutes.

After the cells were washed three times with SM, goat anti-Human IgG alexa 647 (Molecular Probes) diluted to a concentration of 10 μg/mL with SM was added thereto at 100 μL/well to perform a reaction at 4° C. for 40 minutes. The cells were washed with SM and resuspended with 100 μL of SM, and the fluorescent intensity was measured by flow cytometry (BD Biosciences, FACS CantoII).

The data was analyzed by FLowJo 7.65 (Tomy Digital Biology Co., Ltd.). As the result, it was found that the binding activity of LV0HV1 against human CRTH2 and monkey CRTH2 were substantially the same as each other as shown in FIG. 21.

INDUSTRIAL APPLICABILITY

According to the present invention, it is possible to provide an anti-human CRTH2 antibody which has desired activity by recognizing and binding to a specific epitope of human CRTH2; the antibody fragment thereof; DNA which encodes the amino acid sequence of the antibody; a vector which includes the DNA; hybridomas and antibody producing cells which produce the antibody; a method of producing the antibody; a composition which includes the antibody or the antibody fragment; a treatment method and a diagnostic method of an allergic disease, an autoimmune disease, a disease accompanied by at least one of increase and hyperergasia of eosinophils; a disease accompanied by at least one of increase and hyperergasia of Th2 cells using the antibody or the antibody fragment; and a medicine and a diagnostic agent which include the antibody or the antibody fragment.

The present invention has been described with reference to particular embodiments, but various changes and modifications can be made without departing from the spirit and scope of the present invention, and this is apparent to those skilled in the art. Further, the present application is based on Japanese Patent Application No. 2015-141633 filed on Jul. 15, 2015, the entire contents of which are incorporated herein by reference.

Sequence Listing Free Text

SEQ ID NO: 3: description of artificial sequence: base sequence of human CRTH2 FLAG-A SEQ ID NO: 4: description of artificial sequence: base sequence of human CRTH2 FLAG-B SEQ ID NO: 5: description of artificial sequence: base sequence of FLAG-tagged human CRTH2 cDNA SEQ ID NO: 6: description of artificial sequence: base sequence of human CRTH2 FLAG-C SEQ ID NO: 7: description of artificial sequence: base sequence of human CRTH2 FLAG-D SEQ ID NO: 8: description of artificial sequence: base sequence of Rat IgG 2bH-A SEQ ID NO: 9: description of artificial sequence: base sequence of Rat IgG 2bH-B SEQ ID NO: 10: description of artificial sequence: base sequence of Ratk-A SEQ ID NO: 11: description of artificial sequence: base sequence of Ratk-B SEQ ID NO: 20: description of artificial sequence: amino acid sequence of Lym2 antibody VH CDR1

SEQ ID NO: 21: description of artificial sequence: amino acid sequence of Lym2 antibody VH CDR2

SEQ ID NO: 22: description of artificial sequence: amino acid sequence of Lym2 antibody VH CDR3

SEQ ID NO: 23: description of artificial sequence: amino acid sequence of Lym2 antibody VL CDR1

SEQ ID NO: 24: description of artificial sequence: amino acid sequence of Lym2 antibody VL CDR2

SEQ ID NO: 25: description of artificial sequence: amino acid sequence of Lym2 antibody VL CDR3

SEQ ID NO: 26: description of artificial sequence: synthetic DNA of VH for chLym2 expression vector SEQ ID NO: 27: description of artificial sequence: synthetic DNA of VL for chLym2 expression vector SEQ ID NO: 28: description of artificial sequence: base sequence of chLym2 VH-A SEQ ID NO: 29: description of artificial sequence: base sequence of chLym2 VH-B SEQ ID NO: 30: description of artificial sequence: base sequence of chLym2 VH-C SEQ ID NO: 31: description of artificial sequence: base sequence of chLym2 VH-D SEQ ID NO: 32: description of artificial sequence: base sequence of LV0

SEQ ID NO: 33: description of artificial sequence: amino acid sequence of synthetic construct SEQ ID NO: 34: description of artificial sequence: base sequence of LV1

SEQ ID NO: 35: description of artificial sequence: amino acid sequence of synthetic construct SEQ ID NO: 36: description of artificial sequence: base sequence of LV2a SEQ ID NO: 37: description of artificial sequence: amino acid sequence of synthetic construct SEQ ID NO: 38: description of artificial sequence: base sequence of LV2b SEQ ID NO: 39: description of artificial sequence: amino acid sequence of synthetic construct SEQ ID NO: 40: description of artificial sequence: base sequence of LV2c SEQ ID NO: 41: description of artificial sequence: amino acid sequence of synthetic construct SEQ ID NO: 42: description of artificial sequence: base sequence of LV3a SEQ ID NO: 43: description of artificial sequence: amino acid sequence of synthetic construct SEQ ID NO: 44: description of artificial sequence: base sequence of LV3b SEQ ID NO: 45: description of artificial sequence: amino acid sequence of synthetic construct SEQ ID NO: 46: description of artificial sequence: base sequence of LV4

SEQ ID NO: 47: description of artificial sequence: amino acid sequence of synthetic construct SEQ ID NO: 48: description of artificial sequence: base sequence of HV0

SEQ ID NO: 49: description of artificial sequence: amino acid sequence of synthetic construct SEQ ID NO: 50: description of artificial sequence: base sequence of HV1

SEQ ID NO: 51: description of artificial sequence: amino acid sequence of synthetic construct SEQ ID NO: 52: description of artificial sequence: base sequence of HV2a SEQ ID NO: 53: description of artificial sequence: amino acid sequence of synthetic construct SEQ ID NO: 54: description of artificial sequence: base sequence of HV2b SEQ ID NO: 55: description of artificial sequence: amino acid sequence of synthetic construct SEQ ID NO: 56: description of artificial sequence: base sequence of HV3

SEQ ID NO: 57: description of artificial sequence: amino acid sequence of synthetic construct SEQ ID NO: 58: description of artificial sequence: base sequence of HV4

SEQ ID NO: 59: description of artificial sequence: amino acid sequence of synthetic construct SEQ ID NO: 60: description of artificial sequence: base sequence of human CRTH2 azami-A SEQ ID NO: 61: description of artificial sequence: base sequence of human CRTH2 azami-B SEQ ID NO: 64: description of artificial sequence: base sequence of cyno CRTH2 azami-A SEQ ID NO: 65: description of artificial sequence: base sequence of cyno CRTH2 azami-B

---

The invention claimed is:

1. A nucleic acid molecule encoding an antibody or an antibody fragment thereof, said antibody or said antibody fragment recognizing at least one of 192th glycine and 194th aspartic acid in the amino acid sequence of human CRTH2 of SEQ ID NO: 2 and binding thereto, wherein the antibody comprises complementarity determining regions (CDR) 1 to 3 of an antibody heavy chain variable region (VH) which comprise amino acid sequences represented by SEQ ID NOS: 20 to 22, respectively, and CDRs 1 to 3 of an antibody light chain variable regions (VL) which comprise amino acid sequences represented by SEQ ID NOS: 23 to 25, respectively.

2. The nucleic acid molecule according to claim 1, wherein the antibody comprises VH comprising the amino acid sequence represented by SEQ ID NO: 49 or the amino acid sequence obtained by introducing at least one modification selected from modifications of substituting 18th leucine with methionine, 77th asparagine with serine, 93th valine with threonine, and 117th threonine with valine in the amino acid sequence represented by SEQ ID NO: 49 and VL comprising the amino acid sequence represented by SEQ ID NO: 33 or the amino acid sequence obtained by at least one modification selected from modifications of substituting 2nd isoleucine with valine, 4th methionine with leucine, 15th proline with leucine, and 85th alanine with proline in the amino acid sequence represented by SEQ ID NO: 33.

3. The nucleic acid molecule according to claim 1, wherein the antibody comprises VH comprising any one of the amino acid sequences represented by SEQ ID NOS: 49, 51, 53, 55, 57, and 59 and VL comprising any one of the amino acid sequences represented by SEQ ID NOS: 33, 35, 37, 39, 41, 43, 45, and 47.

4. The nucleic acid molecule according to claim 1, wherein the antibody comprises a human Fc region.

5. The nucleic acid molecule according to claim 1, wherein the antibody is an antibody which binds to monkey CRTH2.

6. The nucleic acid molecule according to claim 1, wherein the antibody fragment is any one selected from Fab, Fab', F(ab')$_2$, scFv, diabody, and dsFv.

7. A recombinant vector which comprises the nucleic acid molecule according to claim 1.

8. A recombinant vector which comprises the nucleic acid molecule according to claim 2.

9. A recombinant vector which comprises the nucleic acid molecule according to claim 3.

10. A recombinant vector which comprises the nucleic acid molecule according to claim 4.

11. A recombinant vector which comprises the nucleic acid molecule according to claim 5.

12. A recombinant vector which comprises the nucleic acid molecule according to claim 6.

13. A transformant host which comprises the recombinant vector according to claim 7.

14. A transformant host which comprises the recombinant vector according to claim 8.

15. A transformant host which comprises the recombinant vector according to claim 9.

16. A transformant host which comprises the recombinant vector according to claim 10.

17. A transformant host which comprises the recombinant vector according to claim 11.

18. A transformant host which comprises the recombinant vector according to claim 12.

19. A method of producing an antibody or the antibody fragment thereof, comprising:
culturing the transformant host according to claim 13 to produce the antibody or the antibody fragment thereof; and
recovering the antibody or the antibody fragment.

20. A hybridoma which produces an antibody or an antibody fragment thereof, said antibody or said antibody fragment recognizing at least one of 192th glycine and 194th aspartic acid in the amino acid sequence of human CRTH2 of SEQ ID NO: 2 and binds thereto, wherein the antibody comprises complementarity determining regions (CDR) 1 to 3 of an antibody heavy chain variable region (VH) which comprise amino acid sequences represented by SEQ ID NOS: 20 to 22, respectively, and CDRs 1 to 3 of an antibody light chain variable regions (VL) which comprise amino acid sequences represented by SEQ ID NOS: 23 to 25, respectively.

21. A method of producing an antibody or the antibody fragment thereof, comprising:
culturing the hybridoma according to claim 20 to produce the antibody or the antibody fragment thereof; and
recovering the antibody or the antibody fragment.

* * * * *

UNITED STATES PATENT AND TRADEMARK OFFICE
CERTIFICATE OF CORRECTION

PATENT NO.            : 10,100,120 B2
APPLICATION NO.   : 15/932185
DATED                    : October 16, 2018
INVENTOR(S)          : Naoya Kameyama et al.

Page 1 of 1

It is certified that error appears in the above-identified patent and that said Letters Patent is hereby corrected as shown below:

In the Claims

Column 1, Line 20, Claim 1; "regions" has been replaced with -- region --

Signed and Sealed this
Twenty-eighth Day of May, 2019

Andrei Iancu
*Director of the United States Patent and Trademark Office*